(12) United States Patent
Harrison et al.

(10) Patent No.: US 12,122,824 B2
(45) Date of Patent: *Oct. 22, 2024

(54) ANTI-TNF ANTIBODIES, COMPOSITIONS, AND METHODS FOR THE TREATMENT OF ACTIVE ANKYLOSING SPONDYLITIS

(71) Applicant: Janssen Biotech, Inc., Horsham, PA (US)

(72) Inventors: Diane D. Harrison, Philadelphia, PA (US); Elizabeth C. Hsia, Kenneth Square, PA (US); Lee-Lian Kim, North Wales, PA (US); Kim Hung Lo, Exton, PA (US)

(73) Assignee: Janssen Biotech, Inc., Horsham, PA (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/320,490

(22) Filed: May 14, 2021

(65) Prior Publication Data

US 2021/0277104 A1    Sep. 9, 2021

Related U.S. Application Data

(63) Continuation of application No. 16/517,594, filed on Jul. 20, 2019, now Pat. No. 11,041,020, which is a continuation of application No. 15/818,063, filed on Nov. 20, 2017, now abandoned.

(60) Provisional application No. 62/452,079, filed on Jan. 30, 2017.

(51) Int. Cl.
| | |
|---|---|
| *A61K 39/395* | (2006.01) |
| *A61K 9/00* | (2006.01) |
| *A61K 31/519* | (2006.01) |
| *A61P 19/02* | (2006.01) |
| *C07K 16/24* | (2006.01) |
| *A61K 39/00* | (2006.01) |

(52) U.S. Cl.
CPC .......... *C07K 16/241* (2013.01); *A61K 9/0019* (2013.01); *A61K 31/519* (2013.01); *A61K 39/3955* (2013.01); *A61P 19/02* (2018.01); *A61K 2039/505* (2013.01); *A61K 2039/54* (2013.01); *A61K 2039/545* (2013.01); *C07K 2317/21* (2013.01); *C07K 2317/76* (2013.01)

(58) Field of Classification Search
CPC ............ C07K 16/241; A61K 2039/505; A61K 9/0019
See application file for complete search history.

(56) References Cited

U.S. PATENT DOCUMENTS

| | | |
|---|---|---|
| 3,773,919 A | 11/1973 | Boswell |
| 4,239,754 A | 12/1980 | Bertrand |
| 4,309,989 A | 1/1982 | Fahim |
| 4,399,216 A | 8/1983 | Axel |
| 4,603,106 A | 7/1986 | Cerami |
| 4,634,665 A | 1/1987 | Axel |
| 4,656,134 A | 4/1987 | Ringold |
| 4,668,218 A | 5/1987 | Virtanen |
| 4,676,980 A | 6/1987 | Segal |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,822,776 A | 4/1989 | Cerami |
| 4,873,316 A | 10/1989 | Meade |
| 4,889,818 A | 12/1989 | Gelfand |
| 4,921,794 A | 5/1990 | Tabor |
| 4,925,673 A | 5/1990 | Steiner |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,116,964 A | 5/1992 | Capon |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,538 A | 7/1993 | Capon |

(Continued)

FOREIGN PATENT DOCUMENTS

| | | | |
|---|---|---|---|
| AU | 1764992 A | 10/1992 | |
| EP | 0218868 A2 | 4/1987 | |

(Continued)

OTHER PUBLICATIONS

US 5,733,746 A, 03/1998, Treco (withdrawn)

(Continued)

*Primary Examiner* — Gyan Chandra

(74) *Attorney, Agent, or Firm* — Riverside Law LLP

(57) ABSTRACT

The present invention relates to compositions and methods utilizing anti-TNF antibodies having a heavy chain (HC) comprising SEQ ID NO:36 and a light chain (LC) comprising SEQ ID NO:37 for use in the safe and effective treatment of active Psoriatic Arthritis (PsA).

7 Claims, 19 Drawing Sheets

Specification includes a Sequence Listing.

(56) References Cited

U.S. PATENT DOCUMENTS

| | | |
|---|---|---|
| 5,225,539 A | 7/1993 | Winter |
| 5,231,024 A | 7/1993 | Moeller |
| 5,260,203 A | 11/1993 | Ladner |
| 5,266,491 A | 11/1993 | Nagata |
| 5,304,489 A | 4/1994 | Rosen |
| 5,342,613 A | 8/1994 | Creaven |
| 5,385,839 A | 1/1995 | Stinski |
| 5,403,484 A | 4/1995 | Ladner |
| 5,404,871 A | 4/1995 | Goodman |
| 5,427,908 A | 6/1995 | Dower |
| 5,447,851 A | 9/1995 | Beutler |
| 5,455,030 A | 10/1995 | Ladner |
| 5,458,135 A | 10/1995 | Patton |
| 5,496,549 A | 3/1996 | Yamazaki |
| 5,514,670 A | 5/1996 | Friedman |
| 5,518,889 A | 5/1996 | Ladner |
| 5,530,101 A | 6/1996 | Queen |
| 5,534,621 A | 7/1996 | Ladner |
| 5,545,806 A | 8/1996 | Lonberg |
| 5,545,807 A | 8/1996 | Surani |
| 5,565,362 A | 10/1996 | Rosen |
| 5,569,825 A | 10/1996 | Lonberg |
| 5,571,698 A | 11/1996 | Ladner |
| 5,576,195 A | 11/1996 | Robinson |
| 5,580,717 A | 12/1996 | Dower |
| 5,580,734 A | 12/1996 | Treco |
| 5,582,996 A | 12/1996 | Curtis |
| 5,585,089 A | 12/1996 | Queen |
| 5,595,898 A | 1/1997 | Robinson |
| 5,601,819 A | 2/1997 | Wong |
| 5,618,920 A | 4/1997 | Robinson |
| 5,625,126 A | 4/1997 | Lonberg |
| 5,625,825 A | 4/1997 | Rostoker |
| 5,633,425 A | 5/1997 | Lonberg |
| 5,637,052 A | 6/1997 | Hirota |
| 5,641,670 A | 6/1997 | Treco |
| 5,643,759 A | 7/1997 | Pfreundschuh |
| 5,643,768 A | 7/1997 | Kawasaki |
| 5,654,407 A | 8/1997 | Boyle |
| 5,656,272 A | 8/1997 | Le |
| 5,656,730 A | 8/1997 | Lee |
| 5,658,570 A | 8/1997 | Newman |
| 5,658,754 A | 8/1997 | Kawasaki |
| 5,661,016 A | 8/1997 | Lonberg |
| 5,693,493 A | 12/1997 | Robinson |
| 5,693,762 A | 12/1997 | Queen |
| 5,698,195 A | 12/1997 | Le |
| 5,698,417 A | 12/1997 | Robinson |
| 5,698,419 A | 12/1997 | Wolpe |
| 5,698,435 A | 12/1997 | Robinson |
| 5,714,352 A | 2/1998 | Jakobobits |
| 5,723,323 A | 3/1998 | Kauffman |
| 5,733,761 A | 3/1998 | Treco |
| 5,750,105 A | 5/1998 | Newman |
| 5,750,373 A | 5/1998 | Garrard |
| 5,763,192 A | 6/1998 | Kauffman |
| 5,763,733 A | 6/1998 | Whitlow |
| 5,766,886 A | 6/1998 | Studnicka |
| 5,767,260 A | 6/1998 | Whitlow |
| 5,770,198 A | 6/1998 | Coller |
| 5,770,222 A | 6/1998 | Unger |
| 5,770,359 A | 6/1998 | Wilson |
| 5,770,428 A | 6/1998 | Boris-Lawrie |
| 5,789,650 A | 8/1998 | Lonberg |
| 5,807,706 A | 9/1998 | Carter |
| 5,814,476 A | 9/1998 | Kauffman |
| 5,814,599 A | 9/1998 | Mitragotri |
| 5,817,483 A | 10/1998 | Kauffman |
| 5,821,333 A | 10/1998 | Carter |
| 5,824,514 A | 10/1998 | Kauffman |
| 5,827,690 A | 10/1998 | Meade |
| 5,827,739 A | 10/1998 | Wilson |
| 5,833,985 A | 11/1998 | Ball |
| 5,837,500 A | 11/1998 | Ladner |
| 5,839,446 A | 11/1998 | Waner |
| 5,849,695 A | 12/1998 | Cohen |
| 5,849,992 A | 12/1998 | Meade |
| 5,851,198 A | 12/1998 | Castellano |
| 5,856,456 A | 1/1999 | Whitlow |
| 5,871,753 A | 2/1999 | Crabtree |
| 5,879,681 A | 3/1999 | Leone-Bay |
| 5,885,793 A | 3/1999 | Griffiths |
| 5,888,511 A | 3/1999 | Skurkovich |
| 5,919,452 A | 7/1999 | Le |
| 5,932,448 A | 8/1999 | Tso |
| 5,958,413 A | 9/1999 | Anagnostopulos |
| 5,959,083 A | 9/1999 | Bosslet |
| 5,959,084 A | 9/1999 | Ring |
| 5,976,862 A | 11/1999 | Kauffman |
| 5,989,530 A | 11/1999 | Lorenz |
| 5,993,833 A | 11/1999 | De Lacharriere |
| 5,994,616 A | 11/1999 | Rosen |
| 6,010,902 A | 1/2000 | Ledbetter |
| 6,017,732 A | 1/2000 | Jespers |
| 6,037,453 A | 3/2000 | Jardieu |
| 6,060,285 A | 5/2000 | Lenz |
| 6,106,833 A | 8/2000 | Ring |
| 6,132,992 A | 10/2000 | Ledbetter |
| 6,180,370 B1 | 1/2001 | Queen |
| 6,190,691 B1 | 2/2001 | Mak |
| 6,193,967 B1 | 2/2001 | Morganelli |
| 6,204,023 B1 | 3/2001 | Robinson |
| 6,210,668 B1 | 4/2001 | Lindhofer |
| 6,277,969 B1 | 8/2001 | Le |
| 6,284,471 B1 | 9/2001 | Le |
| 7,521,206 B2 | 4/2009 | Heavner |
| 7,691,378 B2 | 4/2010 | Heavner |
| 8,241,899 B2 | 8/2012 | Heavner |
| 9,512,065 B2 | 12/2016 | Northen |
| 2002/0168360 A1 | 11/2002 | Dingivan |
| 2003/0049725 A1 | 3/2003 | Heavner |
| 2007/0071747 A1 | 3/2007 | Hoffman |
| 2008/0311043 A1* | 12/2008 | Hoffman ............... C07K 16/241 424/9.2 |
| 2009/0028794 A1 | 1/2009 | Medich |
| 2009/0214528 A1 | 8/2009 | Dorai |
| 2010/0266590 A1 | 10/2010 | Demetri |
| 2011/0251099 A1 | 10/2011 | Visvanathan |
| 2016/0130340 A1 | 5/2016 | Smith |

FOREIGN PATENT DOCUMENTS

| | | |
|---|---|---|
| EP | 0350690 A2 | 1/1990 |
| EP | 0380068 A1 | 8/1990 |
| EP | 0393438 A2 | 10/1990 |
| EP | 0433900 A1 | 6/1991 |
| EP | 0237507 B1 | 12/1991 |
| EP | 0525570 A2 | 2/1993 |
| EP | 0526905 A3 | 5/1993 |
| EP | 0229246 B1 | 8/1993 |
| EP | 0260610 B1 | 9/1993 |
| EP | 0288088 B1 | 3/1994 |
| EP | 0368684 B1 | 3/1994 |
| EP | 0371998 B1 | 3/1994 |
| EP | 0590689 A2 | 4/1994 |
| EP | 0229046 B1 | 5/1994 |
| EP | 614989 A1 | 9/1994 |
| EP | 0212489 B1 | 11/1994 |
| EP | 0308378 B1 | 11/1994 |
| EP | 0412486 B1 | 11/1994 |
| EP | 0398327 B1 | 3/1995 |
| EP | 0438474 B1 | 5/1996 |
| EP | 0463151 B1 | 6/1996 |
| EP | 0550400 B1 | 7/1996 |
| EP | 0351789 B1 | 11/1998 |
| EP | 0486526 B2 | 3/2001 |
| EP | 0610201 B1 | 5/2001 |
| EP | 0710719 B1 | 3/2007 |
| EP | 2870137 B1 | 5/2018 |
| GB | 2272440 A | 5/1994 |
| JP | 11127855 A | 5/1999 |
| WO | 8605803 A1 | 10/1986 |
| WO | 8806630 A1 | 9/1988 |
| WO | 8906283 A1 | 7/1989 |

(56) References Cited

FOREIGN PATENT DOCUMENTS

| | | |
|---|---|---|
| WO | 9000902 A1 | 2/1990 |
| WO | 9003809 A1 | 4/1990 |
| WO | 9004036 A1 | 4/1990 |
| WO | 9005370 A1 | 5/1990 |
| WO | 9014424 A1 | 11/1990 |
| WO | 9014430 A1 | 11/1990 |
| WO | 9014443 A1 | 11/1990 |
| WO | 9100360 A1 | 1/1991 |
| WO | 9102078 A1 | 2/1991 |
| WO | 9109967 A1 | 7/1991 |
| WO | 9117271 A1 | 11/1991 |
| WO | 9118980 A1 | 12/1991 |
| WO | 9119818 A1 | 12/1991 |
| WO | 9200373 A1 | 1/1992 |
| WO | 1992001047 A1 | 1/1992 |
| WO | 9203461 A1 | 3/1992 |
| WO | 9205258 A1 | 4/1992 |
| WO | 9206204 A1 | 4/1992 |
| WO | 9207076 A1 | 4/1992 |
| WO | 9211272 A1 | 7/1992 |
| WO | 9211383 A1 | 7/1992 |
| WO | 9213095 A1 | 8/1992 |
| WO | 9214843 A1 | 9/1992 |
| WO | 9216221 A1 | 10/1992 |
| WO | 9216553 A1 | 10/1992 |
| WO | 9218619 A1 | 10/1992 |
| WO | 1992020791 A1 | 11/1992 |
| WO | 9302108 A1 | 2/1993 |
| WO | 9308278 A1 | 4/1993 |
| WO | 1993006213 A1 | 4/1993 |
| WO | 9308829 A1 | 5/1993 |
| WO | 9311383 A1 | 6/1993 |
| WO | 1993011236 A1 | 6/1993 |
| WO | 1993019172 A1 | 9/1993 |
| WO | 9406498 A1 | 3/1994 |
| WO | 9408552 A2 | 4/1994 |
| WO | 9416970 A1 | 8/1994 |
| WO | 9418219 A1 | 8/1994 |
| WO | 9425585 A1 | 11/1994 |
| WO | 9501538 A1 | 1/1995 |
| WO | 9516027 A1 | 6/1995 |
| WO | 9607754 A1 | 3/1996 |
| WO | 9619256 A1 | 6/1996 |
| WO | 9633735 | 10/1996 |
| WO | 9634096 A1 | 10/1996 |
| WO | 9713852 A1 | 4/1997 |
| WO | 9720032 A1 | 6/1997 |
| WO | 9722376 A1 | 6/1997 |
| WO | 9725086 | 7/1997 |
| WO | 9729131 A1 | 8/1997 |
| WO | 9801757 A1 | 1/1998 |
| WO | 9824884 A1 | 6/1998 |
| WO | 9824893 A1 | 6/1998 |
| WO | 9835888 A1 | 8/1998 |
| WO | 9850433 A2 | 11/1998 |
| WO | 9853847 A1 | 12/1998 |
| WO | 9906834 A2 | 2/1999 |
| WO | 0212500 A2 | 2/2001 |
| WO | 0212502 A2 | 2/2002 |
| WO | 2008016633 | 2/2008 |
| WO | 2010056399 A1 | 5/2010 |
| WO | 2014006414 A1 | 1/2014 |
| WO | 2014140509 A1 | 9/2014 |

OTHER PUBLICATIONS

Doyle et al., Rheumatology 52: 1214-1219, (2013).*
Deodhar, A. A. et al, "Safety and Efficacy of Intravenous Golimumab in Adult Patients with Active Ankylosing Spondylitis: Results through Week 28", Arthritis Rheumatol, 68, Suppl. 10, abstract No. 1043, Sep. 28, 2016, 3 pages.
Acosta Felquer et al., "Drug therapies for peripheral joint disease in psoriatic arthritis: a systematic review", Journal of Rheumatology, (Nov. 30, 2014), vol. 41, No. 11, doi:10.3899/jrheum.140876, ISSN 0315-162X, pp. 2277-2285, XP055622320.
Aderka, Dan et al., "IL-6 Inhibits Lipopolysaccharide-Induced tumor Necrosis Factor Production in Cultured Human Monocytes, U937 Cells, and in Mice," J Immunol, 143:3517-3523(1989).
Aderka, Dan et al., "The Possible Role of Tumor Necrosis Factor (TNF) and Its Natural Inhibitors, The Soluble-TNF Receptors, In Autoimmune Diseases," Israel J. Med. Scl., 28(2):126-130 (1992).
Aderka, Dan, "Role of Tumor Necrosis Factor in the Pathogenesis of Intravascular Coagulopathy of Sepsis: Potential New Therapeutic Implications," IsrJ Med Scl, 27:52-60 (1991).
Aggarwal, Bharat B. et al., "Human Tumor Necrosis Factor Production, Purification and Characterization," J. of Biol. Chem., 260(4):2345-2354 (1985).
Akama, Hideto et al., "Mononuclear Cells Enhance Prostaglandin E2 Production of Polymorphonuclear Leukocytes via Tumor Necrosis Factor a," Biochemical and Biophysical Research Comm., 168(2):857-862 (1990).
Alt, et al., "Selective Multiplication of Dihydrofolate Reductase Genes in Methotrexate-resistant Variants of Cultured Murine Cells", J. Biol. Chem. 253:1357-1370 (1978).
Anonymous, "History of Changes for Study NCT02181673", submitted Jan. 23, 2017,https://clinicaltrials.gov/ct2/history/NCT02181673?V _30=View#StudyPage Top.
Ashkenazi et al., "Protection against endotoxic shock by a tumor necrosis factor receptor immunoadhesin", Proc. Natl. Acad. Sci. USA 88:10535-10539 (1991).
Babcook et al., "A novel strategy for generating monoclonal antibodies from single, isolated lymphocytes producing antibodies of defined specificities", Proc. Natl. Acad. Sci. USA 93:7843-7848(1996)).
Baker et al., "Control of established experimental allergic encephalomyelitis by inhibition of tumor necrosis factor (TNF) activity within the central nervous system using monoclonal antibodies and TNF receptor-immunoglobulin fusion proteins", Eur. J. Immunol. 24:2040-2048 (1994).
Basra MKA, Fenech R, Gatt RM, Salek MS, Finlay AY. The Dermatology Life Quality Index 1994-2007: a comprehensive review of validation data and clinical results. Br J Rheumatol. 2008;159:997-1035.
Bebbington, et al., "High-Level Expression of a Recombinant Antibody from Myeloma Cells Using a Glutamine Systhetase Gene as an Amplifiable Selectable Marker", Bio/Technology 10:169-175(1992)).
Berkow et al., Eds, The Merck Manual of Diagnosis and Therapy, Sixteenth Edition, Merck Research Laboratories, Rahway, NJ 1992 p. 1263-1287.
Beutler, B. et al., "Identity of tumour necrosis factor and the macrophage-secreted factor cachectin," Nature, 316:552-554 (1985).
Beutler, B. et al., "Passive Immunization Against Cachectin/Tumor Necrosis Factor Protects Mice from Lethal Effect of Endotoxin," Science, 229:869-871 (1985).
Beutler, B. et al., "Purification of Cachectin, a Lipoprotein Lipase-Suppressing Hormone Secreted by Endotoxin-induced RAW 264.7 Cells," J. Exp. Med., 161:984-995 (1985).
Bodmer, Mark, "Humanized Antibodies for Anti-TNF Therapy," Abstract, Endotoxemia & Sepsis Conference (1991).
Boshart, et al., "A Very Strong Enhancer Is Located Upstream of an Immediate Early Gene of Human Cytomegalovirus", Cell 41:521-530 (1985)).
Bringman, Timothy S. and Aggarwal, Bharat B., "Monoclonal Antibodies to Human Tumor Necrosis Factors Alpha and Beta: Applications for Affinity Purification, Immunoassays, and as Structural Probes," Hybridoma, 6(5):489-507 (1987).
Butler et al., "TNF Receptor Fusion Proteins Are Effective Inhibitors of TNF-Mediated Cytotoxicity on Human KYM-1D4 Rhabdomyosarcoma Cells", Cytokine 6(6):616-623 (1994).
Capellas, et al., "Enzymatic Condensation of Cholecystokinin CCK-8 (4-6) and CCK-8 (7-8) Peptide Fragments in Organic Media," Biotechnology and Bioengineering, 56(4): 456-463 (1997).
Capon et al., "Designing CD4 immunoadhesins for AIDS therapy", Nature 337:525-531 (1989).

(56) References Cited

OTHER PUBLICATIONS

Carter et al., "Humanization of an anti-p185HER2 antibody for human cancer therapy", Proc. Natl. Acad. Sci. U.S.A. 89:4285 (1992).
Cassell SE, Bieber JD, Rich P, Tutuncu ZN, Lee SJ, Kalunian KC, Wu CW, Kavanaugh A. The modified Nail Psoriasis Severity Index: validation of an instrument to assess psoriatic nail involvement in patients with psoriatic arthritis. J Rheumatol. 2007;34(1):123-129.
Cella D, Yount S, Sorensen M, Chartash E, Sengupta N, Grober J. Validation of the Functional Assessment of Chronic Illness Therapy Fatigue Scale relative to other instrumentation in patients with rheumatoid arthritis. J Rheumatol. 2005;32(5):811-819.
Chandran V, Bhella S, Schentag C, Gladman D. Functional Assessment of Chronic Illness Therapy-Fatigue Scale is valid in patients with psoriatic arthritis. Ann Rheum Dis. 2007;66:936-939.
Chothia, et al., "Canonical Structures for the Hypervariable Regions of Immunoglobulins," Journal of Molecular Biology, 196: 901-917 (1987).
Coates LC, Helliwell PS. Validation of minimal disease activity criteria for psoriatic arthritis using interventional trial data. Arthritis Care Res (Hoboken). 2010; 62(7):965-969.
Cohen et al., "Intravenous golimumab in rheumatoid arthritis", Expert Review of Clinical Immunology, (May 15, 2014), vol. 10, No. 7, doi:10.1586/1744666X.2014.918847, pp. 823-830, XP009516813.
Collins, M.S. et al., "Immunoprophylaxis of Polymicrobic Cellulitis with a Human Monoclonal Antibody Against Lipopolysaccharide Antigen of Pseudomonas aeruginosa," Abstract E-63, Abstracts of Annual Meeting 1989.
Conrad et al., "Compartment-specific accumulation of recombinant immunoglobulins in plant cells: an essential tool for antibody production and immunomodulation of physiological functions and pathogen activity", Plant Mol. Biol. 38:101-109 (1998).
Canadian Examination Report for CA2878319 dated Dec. 11, 2019.
Corcoran et al., "Characterization of ligand binding by the human p55 tumour-necrosis-factor receptor", Eur. J. Biochem. 223:831-840 (1994)).
Costello P, FitzGerald O. Disease mechanisms in psoriasis and psoriatic arthritis. Curr Rheumatol Rep. 2001 ;3(5):419-427.
Cramer et al., "Transgenic Plants for Therapeutic Proteins: Linking Upstream and Downstream Strategies", Curr. Top. Microbol. Immunol. 240:95-118 (1999).
Cross, A.S. et al., "Pretreatment with Recombinant Murine Tumor Necrosis Factor a Cachectin and Murine Interleukin 1 a Protects Mice from Lethal Bacterial Infection," J of Exp Med., 169:2021-2027 (1989).
Cullen, et al., "Functional Analysis of the Transcription Control Region Located Within the Avian Retroviral Long Terminal Repeat", Molec. Cell. Biol. 5:438-447 (1985)).
Cunningham and Wells, "High-Resolution Epitope Mapping of hGH-Receptor Interations by Alanine-Scanning Mutagenesis", Science Ausubel, supra, Chapters 8, 15; 244:1081-1085 (1989)).
D. Shealy et al., "Characterization of golimumab, a human monoclonal antibody specific for human tumor necrosis factor alpha", MABS, vol. 2, No. 4, pp. 428-439 (2010).
De Vos, et al., "Human Growth Hormone and Extracellular Domain of Its Receptor: Crystal Structure of the Complex", Science 255:306-312 (1992)).
Di Giovine, Francesco, S. et al., "Tumour necrosis factor in synovial exudates," Annals of the Rheumatic Diseases, 47:768-772 (1988).
Duncombe, Andrew S. et al., "Tumor Necrosis Factor Mediates Autocrine Growth Inhibition in a Chronic Leukemia," J Immunol, 143:3828-3834 (1989).
Dupont et al., "*Escherichia coli* Diarrhea" Bacterial Infections of Humans: Epidemioloqv and Control, A.S. Evans et al., 2nd Edition, Spring Science & Business Media, New York, pp. 239-254(1991).
E. Rankin et al., "The therapeutic effects of an engineered human anti-tumour necrosis factor alpha antibody (CDP571) in rheumatoid arthritis", British Journal of Rheumatology, vol. 34, No. 4, pp. 334-342, XP000674590 (Apr. 1995).

Echtenacher, Bernd et al., "Requirement of Endogenous Tumor Necrosis Factor/Cachectin for Recovery from Experimental Peritonitis," J. of Immunology, 145(11):3762-3766 (1990).
Eck, Michael J. and Sprang, Stephen R., "The Structure of Tumor Necrosis Factor-L at 2.6 L Resolution," J Biol Chem, 264:17595-17605 (1989).
Elliott, M.J. et al., "A Repeated Therapy with Monoclonal Antibody to Tumour Necrosis Factor a (cA2) in Patients with Rheumatoid Arthritis", The Lancet, 344:1125-1127, 1994.
Engelmann, Hartmut et al., "A Tumor Necrosis Factor-binding Protein Purified to Homogeneity from Human Urine Protects Cells from Tumor Necrosis Factor Toxicity," J. of Bio. Chem., 264(20): 1974-11980 (1989).
Engelmann, Hartmut et al., "Two Tumor Necrosis Factor-binding Proteins Purified from Human Urine," J. of Bio. Chem., 265(3):1531-1536 (1990).
Eren et al. "Human monoclonal antibodies specific to hepatitis B virus generated in a human/mouse radiation chimera: the Trimera system", Immunol. 93: 154-161 (1998).
Euroqol Group. Euroqol—a new facility for the measurement of health-related quality of life. Health Policy. 1990;16:199-208.
Exley, A.R. et al., "Monoclonal Antibody (Mab) to Recombinant Human Tumour Necrosis Factor (rhTNF) in the Prophylaxis and Treatment of Endotoxic Shock in Cynomolgus Monkeys," Medical Research Society, Abstract 184, p. 50 (1989).
Exley, A.R. et al., "Monoclonal antibody to TNF in severe septic shock," The Lancet, 335:1275-1277(1990).
Faraawi et al., 2016, "Comparison of Baseline Characteristics of Rheumatoid Arthritis Patients Initating Therapy with Subcutaneous Golimumab and Infliximab and Intravenous Golimumab: An Analysis from the Prospective, Observational Registry, BioTRAC." The Journal of Rheumatology, 43(6), No. 87, p. 1186.
Feldman SR, Gordon KB, Bala M, et al. Infliximab treatment results in significant improvement in the quality of life of patients with severe psoriasis: a double-blind placebo-controlled trial. British Journal of Dermatology. 2005;152:954-960.
Felson, et al., "American College of Rheumatology Preliminary Definition of Improvement in Rheumatoid Arthritis," Arthritis & Rheumatism, 38 (6): 727-735 (1995).
Fendly, Brian M. et al., "Murine Monoclonal Antibodies Defining Neutralizing Epitopes on Tumor Necrosis Factor," Hybridoma, 6(4):359-370 (1987).
Finlay AY, Khan GK. Dermatology Life Quality Index (DLQI)—a simple practical measure for routine clinical use. Clin Exp Dermatol. 1994;19(3):210-216.
Fisch et al., "Site-Specific Modification of a Fragment of a Chimeric Monoclonal Antibody Using Reverse Proteolysis", Bioconjugate Chem., 3:147-153 (1992).
Fischer et al., "Towards molecular farming in the future: moving from diagnostic protein and antibody production in microbes to plants", Biotechnol. Appl. Biochem. 30:101-108 (Oct. 1999).
Fishwald et al., "High-avidity human IgGk monoclonal antibodies from a novel strain of minilocus transgenic mice", Nat Biotechnol 14(7):845-851 (1996).
Fong, Yuman and Lowry, Stephen F., "Tumor Necrosis Factor in the Pathophysiology of Infection and Sepsis," Clin Immunol Immunopathol, 55:157-170 (1990).
Fong, Yuman et al., "Antibodies to Cachectin/Tumor Necrosis Factor Reduce Interleukin 1ß and Interleukin 6 Appearance During Lethal Bacteremia," J. Exp. Med., 170:1627-1633 (1989).
Foote et al., "Antibody Framework Residues Affecting the Conformation of the Hypervariable Loops", Journal of Molecular Biology, 224(2), pp. 487-499 (1992).
Fredriksson T, Pettersson U. Severe psoriasis—oral therapy with a new retinoid. Dermatologica. 1978;157(4):238-244.
Fries JF, Spitz P, Kraines RG, Holman HR. Measurement of patient outcomes in arthritis. Arthritis Rheum. 1980;23(2):137-145.
Galloway, Cynthia J. et al., "Monoclonal anti-tumor necrosis factor (TNF) antibodies protect mouse and human cells from TNF cytotoxicity," J. of Immunological Methods, 140:37-43 (1991).
Garrett S, Jenkinson T, Kennedy LG, Whitelock H, Gaisford P, Calin A. A new approach to defining disease status in ankylosing

(56) References Cited

OTHER PUBLICATIONS spondylitis: the Bath Ankylosing Spondylitis Disease Activity Index. J Rheumatol. 1994;21(12):2286-2291.
Genebank Accession, No. M32046 (Jun. 15, 1990).
Genebank Accession, No. N90300 (Nov. 1, 1989).
Gillies, Stephen D. et al., "High-level expression of chimeric antibodies using adapted cDNA variable region cassettes," J Immunol Methods, 125:191-202 (1989).
Gladman DD, Inman RD, Cook RJ, et al. International spondylarthrites interobserver reliability exercise-the INSPIRE study: II. Assessment of peripheral joints, enthesitis, and dactylitis. J Rheumatol. 2007;34(8):1740-1745.
Gladman DD, Ziouzina O, Thavaneswaran A, Chandran V. Dactylitis in psoriatic arthritis: prevalence and response to therapy in the biologic era. J Rheumatol. 2013;40(8):1357-1359.
Goedkoop AY, Kraan MC, Teunissen MB, et al. Early effects of tumour necrosis factor alpha blockade on skin and synovial tissue in patients with active psoriasis and psoriatic arthritis. Ann Rheum Dis. 2004;63(7):769-773.
Gorman, S.D. and Clark, M.R., "Humanisation of monoclonal antibodies for therapy," Sem Immunol, 2:457-466 (1990).
Gossen, and H. Bujard, "Tight control of gene expression in mammalian cells by tetracycline-responsive promotoers", Proc. Natl. Acad. Sci. USA 89: 5547-5551 (1992).
Gray et al., "Secretion capture and report web: use of affinity derivatized agarose microdroplets for the selection of hybridoma cells", J. Imm. Meth. 182:155-163 (1995).
Green et al, "Antigen-specific human monoclonal antibodies from mice engineered with human Ig heavy and light chain YACs", Nature Genetics 7:13-21 (1994).
Green, L. "Antibody Engineered via Genetic Engineering of the Mouse: Xenomouse Strains Are a Vehicle for the Facile Generation of Therapeutic Human Monoclonal Antibodies", Journal of Immunological Methods, 231, pp. 11-23 (1999).
H. Hoogenboom et al., "By-passing immunization. Human antibodies from synthetic repertoires of germline VH gene segments rearranged in vitro", Journal of Molecular Biology, vol. 227, No. 2, XP024020530; p. 386 (Sep. 10, 1992).
Hanes et al. "Ribosome display efficiently selects and evolves high-affinity antibodies in vitro from immune libraries", Proc Natl. Aca. Sci USA 95 14130-14135 (Nov. 1998).
Hanes et al., "In vitro selection and evolution of functional proteins by using ribosome display", Proc. Natl. Acad. Sci. USA 94:4937-4942 (May 1997).
Harris, "Ankvlosing Spondylitis", Chapter 6, Spondyloarthropathies, Kellev's Textbook of Rheumatology, 6th Edition, Sledqe CB, pas. 1039-1053 (2001).
Hayashi, H et al., "An Enzyme-linked Immunosorbent Assay for Recombinant Human Tumor Necrosis Factor Using Monoclonal Antibody," Recent Adv. Chemother, 820-821 (1985).
Healy PJ, Helliwell PS. Measuring clinical enthesitis in psoriatic arthritis: assessment of existing measures and development of an instrument specific to psoriatic arthritis. Arthritis Rheum. 2008;59(5):686-691.
Herve, P. et al., "Monoclonal Anti TNF a Antibody for the Treatment of Severe Acute GvHD in Humans," Abstract 3.25, Lymphoma Res. 9:591 (1990).
Hinshaw, L.B. et al., "Survival of Primates in LD100 Septic Shock Following Therapy with Antibody to Tumor Necrosis Factor (TNFa)," Circulatory Shock, 30:279-292 (1990).
Hirai, Makoto et al., "Production and characterization of monoclonal antibodies to human tumor necrosis factor," J. ofImmun. Methods, 96:57-62 (1987).
Hood et al., "Molecular Farming of Industrial Proteins from Transgenic Maize", Adv. Exp. Med. Biol. 464:127-147(1999).
Husted JA, Gladman DD, Cook RJ, Farewell VT. Responsiveness of health status instruments to changes in articular status and perceived health in patients with psoriatic arthritis. J Rheumatol. 1998;25(11):2146-2155.

Itoh et al., "Application of Inverse Substrates to Trypsin-Catalyzed Peptide Synthesis", Bioorg. Chem., 24(1): 59-68 (1996).
J. L. Hamlin and C. Ma, "The mammalian dihydrofolate reductase locus", Biochem. et Biophys. Acta 1097:107-143 (1990).
Jones, et al., "Replacing the complementarity-determining regions in a human antibody with those from a mouse," Nature, 321: 522-525 (1986).
Junginger, et al. "Visualization of Drug Transport Across Human Skin and the Influence of Penetration Enhancers", In Drug Permeation Enhancement, Hsieh, D. S., Eds., pp. 59-90 (Marcel Dekker, Inc. New York 1994.
Kameyama, Koh-zoh, et al., "Convenient plasmid vectors for construction of chimeric mouse/human antibodies," FEBS Lett, 244:301-306 (1989).
Katsube, Y., et al., "Analysis of k light chain contribution to anti-DNA antibody activity of a human VH4-21-encoded monoclonal antibody (NE-1) by antibody-phage display technique", Int J Mol. Med, 1(5):863-868 (1998)).
Kavanaugh et al., 2014, "Clinical efficacy, radiographic and safety findings through 5 years of subcutaneous golimumab treatment in patients with active psoriatic arthritis: results from a long-term extension of a randomised, placebo-controlled trial (the GO-REVEAL study)", Ann Rheum Dis, 73(9): 1689-1694.
Kawasaki, Hajime et al., "Analysis of Endotoxin Fever in Rabbits by Using a Monoclonal Antibody to Tumor Necrosis Factor (Cachectin)," Infection and Immunity, 57(10):3131-3135 (1989).
Kenny et al., "Production of Monoclonal Antiboodies Using a Secretion Capture Report Web", Bio/ Technol. 13:787-790 (1995).
Khilji FA, Gonzalez M, Finlay AY. Clinical meaning of change in dermatology life quality index scores. Br J Dermatol. 2002;147(suppl 62): 25-54. Simponi IV (golimumab) Clinical Protocol CNTO148PSA3001 Amendment 2 98 Approved, Jun. 29, 2016.
Knight, D. M. et al., "A Construction and Initial Characterization of a Mouse-Human Chimeric Anti-TNF Antibody", Mol. Immunol. 30 (16): 1443-1453, 1993.
Kolls et al., "Prolonged and effective blockade of tumor necrosis factor activity through adeno virus-mediated gene transfer", Proc. Natl. Acad. Sci. USA 91:215-219 (1994).
Kozbor et al., "The production of monoclonal antibodies from human lymphocytes", Immunol. Today, 4:72-79(1983).
Kumaran et al., "Conformationally driven protease-catalyzed splicing of peptide segments: V8 protease-mediated synthesis of fragments derived from thermolysin and ribonuclease A", Protein Sci. 6(10):2233-2241 (1997).
Larmonier et al., "The inhibition of TNF-alpha anti-tumoral properties by blocking antibodies promotes tumor growth in rat model" Exp. Cell Res. Mar. 30, 2007; Epub ahead of print; Abstract only.
Lassalle, Ph., et al., "Potential Implicaton of Endothelial Cells in Bronchial Asthma," Int Arch Allergy Appl Immunol, 94:233-238 (1991).
Lesslauer et al., "Recombinant soluble tumor necrosis factor receptor proteins protect mice from lipopolysaccharide-induced lethality", Eur. J. Immunol. 21:2883-2886 (1991).
Liang, Chi-Ming et al., "Production and Characterization of Monoclonal Antibodies Against Recombinant Human Tumor Necrosis Factor/Cachectin," Biochem. & Biophy. Res. Comm., 137(2):847-854(1986).
Loetscher et al., "Molecular Cloning and Expression of the Human 55 kd Tumor Necrosis Factor Receptor", Cell 61: pp. 351-359 (1990).
Lonberg et al. "Antigen-specific human antibodies from mice comprising four distinct genetic modifications", Nature 368:856-859 (1994).
Lonberg et al., "Human Antibodies from Transgenic Mice", Int Rev Immunol 13(1):65-93 (1995).
Lucas, R. et al., "Generation and characterization of a neutralizing rat anti-rm TNF-a monoclonal antibody," Immunology, 71:218-223 (1990).
M. J. Page and M. A. Sydenham, "High Level Expression of the Humanized Monoclonal Antibody Campath-1H in Chinese Hamster Ovary Cells", Biotechnology 9:64-68 (1991)).
Ma et al., "Immunotherapeutic potential of antibodies produced in plants", Trends Biotechnol. 13:522-7(1995).

(56) References Cited

OTHER PUBLICATIONS

Ma et al., "Plant Antibodies for Immunotherapy", Plant Physiol. 109:341-6 (1995).
Marrack et al, "The Staphylococcal Enterotoxins and Their Relatives", Science, 248:705-711 (1990).
Meager, Anthony et al., "Preparation and Characterization of Monoclonal Antibodies Directed Against Antigenic Determinants of Recombinant Human Tumour Necrosis Factor (rTNF)," Hybridoma, 6(3):305-311 (1987).
Mease PJ, Antoni CE, Gladman DD, Taylor WJ. Psoriatic arthritis assessment tools in clinical trials. Ann Rheum Dis. 2005;64(Suppl II):ii49-ii54.
Mease PJ, Kivitz AJ, Burch FX, et al. Etanercept treatment of psoriatic arthritis: safety, efficacy, and effect on disease progression. Arthritis Rheum. 2004;50(7):2264-2272.
Mease PJ. Measures of psoriatic arthritis: Tender and Swollen Joint Assessment, Psoriasis Area and Severity Index (PASI), Nail Psoriasis Severity Index (NAPSI), Modified Nail Psoriasis Severity Index (mNAPSI), Mander/Newcastle Enthesitis Index (MEI), Leeds Enthesitis Index (LEI), Spondylarthrites Research Consortium of Canada (SPARCC), Maastricht Ankylosing Spondylitis Enthesis Score (MASES), Leeds Dactylitis Index (LDI), Patient Global for Psoriatic Arthritis, Dermatology Life Quality Index (DLQI), Psoriatic Arthritis Quality of Life (PsAQOL), Functional Assessment of Chronic Illness Therapy—Fatigue (FACIT-F), Psoriatic Arthritis Response Criteria (PsARC), Psoriatic Arthritis Joint Activity Index (PsAJAI), Disease Activity in Psoriatic Arthritis (DAPSA), and Composite Psoriatic Disease Activity Index (CPDAI). Arthritis Care Res (Hoboken). 2011;63 Suppl 11:S64-S85.
Mendez, et al., "Functional transplant of megabase human immunoglobulin loci recapitulates human antibody response in mice," Nature Genetics, 15(2): 146-156 (1997).
Milstein, et al., "Hybrid hybridomas and their Use in Immunohistochemistry," Nature, 305: 537-540 (1983).
Mocellin et al., "Tumor necrosis factor, cancer and anticancer therapy", Cytokine Growth Factor Rev. Feb. 2005; 16(1) 35-53, Epub Dec. 19, 2004.
Moller, Achim et al., "Monoclonal Antibodies to Human Tumor Necrosis Factor a: In Vitro and In Vivo Application," Cytokine, 2(3):162-169 (1990).
Morrison, Sherie L., "Transfectomas Provide Novel Chimeric Antibodies," Science, 229:1202-1207(1985).
Muller, "Determination of Affinity and Specificity of Anti-Hapten Antibodies by Competitive Radioimmunoassay", Meth. Enzymol., 92:589-601 (1983).
Murphy, et al., "Matrix metalloproteinase degradation of elastin, type IV collagen and proteoglycan", Biochem. J. 227:277-279 (1991).
Nagai, M. et al., "Antibody to tumor necrosis factor (TNF) reduces endotoxin fever," Experientia, 44:606-607 (1988).
Neuberger, M., "Generating high-avidity human Mabs in mince", Nature Biotech. 14:826 (1996).
Nguyen et al., "Production of Human Monoclonal Antibodies in SCID Mouse", Microbiol. Immunol. 41:901-907(1997).
Nophar, Yaron et al., "Soluble forms of tumor necrosis factor receptors (TNF-Rs). The cDNA for the type 1 TNF-R, cloned using amino acid sequence data of its soluble form, encodes both the cell surface and a soluble form of the receptor," The EMBO Journal, 9(10):3269-3278(1990).
Opal, Steven M et al., "Efficacy of a Monoclonal Antibody Directed Against Tumor Necrosis Factor in Protecting Neutropenic Rats from Lethal Infection with Pseudomonas aeruginosa," J. of Infectious Diseases, 161:1148-1152 (1990).
Parrillo, Joseph E., "Pathogenetic Mechanisms of Septic Shock," N.E. Journal of Medicine, 328(20):1471-1477 (1993).
Partsch G, Steiner G, Leeb BF, Dunky A, Broil H, Smolen JS. Highly increased levels of tumor necrosis factor-alpha and other proinflammatory cytokines in psoriatic arthritis synovial fluid. J Rheumatol. 1997;24(3):518-523.
Paulus, H., A Preparation and Biomedical Applications of Bispecific Antibodies®, Behring Inst. Mitt, No. 78:118-132 (1985).
Pennington, James, "TNF: Therapeutic Target in Patients with Sepsis," ASM News, 58(9):479-482(1992).
Peppel et al., "A Tumor Necrosis Factor (TNF) Receptor-IgG Heavy ChainChimeric Protein as a Bivalent Antagonist of TNF Activity", J. Exp. Med. 174:1483-1489 (1991).
Pham et al., 2006, "TNFa antagonist therapy in ankylosing spondylitis and psoriatic arthritis: recommendations of the French Society for Rheumatology." Joint Bone Spine, Elsevier, Amsterdam, NL , 73(5), pp. 547-553.
Pham T, Guillemin F, Claudepierre P, et al. TNFa antagonist therapy in ankylosing spondylitis and psoriatic arthritis: recommendations of the French Society for Rheumatology. Joint Bone Spine. 2006;73:547-553.
Piguet, Pierre-Francois et al., "Tumor Necrosis Factor/Cachectin is an Effector of Skin and Gut Lesions of the Acute Phase of Graft-vs.-Host Disease," J. Exp. Med., 166:1280-1289 (1987).
Powell et al., "Gel Microdroplets and Flow Cytometry: Rapid Determination of Antibody Secretion by Individual Cells Within a Cell Population", Biotechnol. 8:333-337 (1990).
Presta et al., "Humanization of an Antibody Directed Against IgE", J. Immunol. 151:2623 (1993).
Reichmann, et al., "Reshaping human antibodies for therapy," Nature, 332: 323-327 (1988).
Ritchlin C, Haas-Smith SA, Hicks D, Cappuccio J, Osterland CK, Looney RJ. Patterns of cytokine production in psoriatic synovium. J Rheumatol. 1998;25(8):1544-1552.
Ruddle, Nancy H et al., "An Antibody to Lymphotoxin and Tumor Necrosis Factor Prevents Transfer of Experimental Allergic Encephalomyelitis," J. Exp. Med., 172:1193-1200 (1990).
Rudikoff et al., Single amino acid substitution altering antigen-binding specificity, PNAS, Mar. 1982, vol. 79, p. 1979-83.
S. Siegal et al., "The mouse/human chimeric momoclonia antibody cA2 neutralizes TNF in vitro and protects transgenic mice from cachexia and TNF lethality in vivo", Cytokine, vol. 7, No. 1 pp. 15-25 XP000990566 (Jan. 1995).
S. Stephens et al., "Comprehensive pharmacokinestic of a humanized antibody and analysis of residual anti-idiotypic responses", Immunology, vol. 85, No. 4, pp. 668-674 XP000881488 (Aug. 1995).
Sandhu et al., "The Use of SCID Mice in Biotechnology and as a Model for Human Disease", Crit. Rev. Biotechnol. 16:95-118 (1996).
Scallon, et al., Functional Comparisons of Different Tumour Necrosis Factor Receptor/IgG Fusion Proteins, Cytokine 7:759-770 (1995).
Schall, Thomas J. et al., "Molecular Cloning and Expression of a Receptor for Human Tumor Necrosis Factor," Cell, 61:361-370 (1990).
Scott et al., "An Anti-Tumor Necrosis Factor-a Antibody Inhibits the Development of Experimental Skin Tumors", Mol. Can Therapy, May 2003, 2:445-451.
Shimamoto, Yoshinori et al., "Monoclonal antibodies against human recombinant tumor necrosis factor: prevention of endotoxic shock," Immunology Letters, 77:311-318 (1988).
Silva, Ayona T. et al., "Prophylactic and Therapeutic Effects of a Monoclonal Antibody to Tumor Necrosis Factor-a in Experimental Gram-Negative Shock," J. of Infectious Diseases, 162:421-427(1990).
Sims et al., "A Humanized CD18 Antibody Can Block Function without Cell Destruction", J. Immunol. 151:2296(1993).
Smith, Craig R., "Human and Chimeric Antibodies to LPS and TNF," 4Abstract, Endotoxemia & Sepsis Conference (1991).
Smith, et al., "Human Interleukin 4: The Solution Structure of a Four-helix Bundle Protein", J. Mol. Biol. 224:899-904 (1992).
Sprague, et al., "Expression of a Recombinant DNA Gene Coding for the Vesiclar Stomatitis Virus Nucleocapsid Protein", J. Virol. 45:773-781 (1983)).
Starnes, H. Fletcher, Jr., et al., "ANTI-IL-6 Monoclonal Antibodies Protect Against Lethal *Escherichia coll* Infection and Lethal Tumor Necrosis FactorL Challenge in Mice," J Immunol, 145:4185-4191 (1990).

(56) References Cited

OTHER PUBLICATIONS

Steadman Medical Dictionary, 27th Ed. 2000 Lippincott Williams & Wilkins—"Carcinoma".
Steenbakkers et al., "Efficient generation of monoclonal antibodies from preselected antigen-specific B", Molec. Biol. Reports 19:125-134 (1994).
Stein et al., "Diseases of the Hearth and Blood Vessels", Internal Medicine, 3rd 3d., p. 1-13, Little Brown and Co. Boston (1990).
Stone et al., "Solid malignancies among patients in the Wegener's Granulomatosis Etanercept Trial", Arthritis Rheum. May 2006; 54(5) 1608-18 abstract only.
Sunahara, N et al., "Simple enzyme immunoassay methods for recombinant human tumor necrosis factor L and its antibodies using a bacterial cell wall carrier," J Immunol Methods, 109:203-214(1988).
Suresh et al., "Bispecific Monoclonal Antibodies from Hybrid Hybridomas", Methods in Enzymology 121:210 (1986).
Tavernier et al., "Analysis of the Structure-Function Relationship of Tumour Necrosis Factor. Human/Mouse Chimeric TNF Proteins: General Properties and Epitope Analysis", Journal Molecular Biology, 211, p. 493-501 (1990).
Taylor et al., "A transgenic mouse that expresses a diversity of human sequence heavy and light chain immunoglobulins", Nucleic Acids Research 20(23):6287-6295 (1992).
Taylor W, Gladman D, Helliwell P, Marchesoni A, Mease P, Mielants H; CASPAR Study Group. Classification criteria for psoriatic arthritis: development of new criteria from a large international study. Arthritis Rheum. 2006;54(8):2665-2673.
Taylor, et al., "Human immunoglobulin transgenes undergo rearrangement, somatic mutation and class switching in mice that lack endogenous IgM," International Immunology, 6(4): 579-591 (1994).
Tracey, Kevin J. et al., "Anti-cachectin/TNF monoclonal antibodies prevent septic shock during lethal bacteraemia," Nature, 330:662-664 (1987).
Traunecker, et al., "Bispecific Single chain molecules (Janusins) target cytotoxic lymphocytes on HIV infected cells," EMBO Journal, 10(12): 3655-3659 (1991).
Tuaillon et al., "Human immunoglobulin heavy-chain minilocus recombination in transgenic mice: Gene-segment use in u and y transcripts", Proc Natl Acad Sci USA 90(8)3720-3724 (1993).
Van der Heijde DM, van Leeuwen MA, van Riel PL, et al. Biannual radiographic assessments of hands and feet in a three-year prospective followup of patients with early rheumatoid arthritis. Arthritis Rheum. 1992;35(1):26-34.
Van der Linden MA. Disease Activity Scores using C-reactive protein. Apr. 5, 2004. Available at: www.umcn.nl/scientist/afdelingen/reumatologie/the das/the_das_crp. Accessed Aug. 19, 2005.
Van Riel P, Fransen J, Scott DL. EULAR handbook of clinical assessments in rheumatoid arthritis. Third ed. Alphen Aan Den Rijn, The Netherlands: Van Zuiden Communications B.V. 2004.
Van Riel PL, van Gestel AM, Scott DL, for the EULAR Standing Committee for International Clinical Studies Including Therapeutic Trials—ESCISIT. EULAR Handbook of Clinical Assessments in Rheumatoid Arthritis. Alphen Aan Den Rijn, The Netherlands: Van Zuiden Communications B.V.; 2000:40.
Veale DJ, Markham T, Fearon U, et al. St Vincents University Hospital, Dublin, Ireland. Therapy in psoriasis and psoriatic arthritis: anti-TNF-alpha clinical and angiogenic responses. Arthritis Rheum. 2003;48(suppl):S168-S169.
Verhoef, J. and Torensma, R., "Prospects for Monoclonal Antibodies in the Diagnosis and Treatment of Bacterial Infections," Eur. J. Clin. Microbiol. Dis., 9(4):247-250 (1990).
Verhoeyen et al., "Reshaping Human Antibodies:Grafting an Antilysozyme Activity", Science 239:1534(1988).
Von Asmuth, E.J.U. et al., "Tumour Necrosis Factor Alpha (TNF-a) and Interleukin 6 in a Zymosan-Induced Shock Model," Scand. J. Immunol., 32:313-319 (1990).
Waldmann, Thomas A., "Monoclonal Antibodies in Diagnosis and Therapy," Science, 252:1657-1662(1991).
Ware JE JR, Sherbourne CD. The MOS 36 item short form health survey (SF 36), I. Conceptual framework and item selection. Med Care. 1992;30(6):473 483.
Ware JE, Kosinski M, Keller SD. Interpretation: NormBased. In: SF-36 Physical and Mental Health Summary Scales: A User's Manual. Boston, MA: The Health Institute; 1994:8:1-8:42.
Wen et al., "Limiting diluation assay for human B cells based on their activation by mutant EL4 thymoma cells:total and antimalaria responder B cell frequencies" J. Immunol. 17:887-892 (1987).
Werlen et al., "Site-Specific Conjugation of an Enzyme and an Antibody Fragment", Bioconjugate Chem., 5:411-417 (1994).
Whitelam, et al., "Antibody production in transgenic plants," Biochemical Society Transactions, Transgenic Plants and Plan Biochemistry, 22: 940-944 (1994).
Whittle, Nigel, et al., "Construction and Expression of a CDR-Grafted Anti-TNF Antibody," J. Cell Blochem, Supl. 13A:96 (1989).
Winter et al., "Antibody-based Therapy", Immunology Today, 14(6), pp. 243-246 (1993).
Wood et al, "Staphylococcal enterotoxins and the immune system", FEMS Microbiology Immunology, 76:121-134 (1991).
Zhuang et al., 2010, Pharmacokinetics of Golimumab, an Anti-TNFalpha Human Monoclonal Antibody After Multiple Subcutaneous or Intravenous Injections in Subjects with Rheumatoid Arthritis Clinical Pharmacology & Therapeutics, vol. 87, Supplement 1, PI-80, p. S34-S35.
Zochling J, van der Heijde D, Burgos-Vargas R, et al. ASAS/EULAR recommendations for the management of ankylosing spondylitis. Ann Rheum Dis. 2006;65(4):442-452.
Kavanaugh A, McInnes I, Mease P, Krueger GG, Gladman D, Gomez-Reino J, Papp K, Zrubek J, Mudivarthy S, Mack M, Visvanathan S, Beutler A. Golimumab, a new human tumor necrosis factor alpha antibody, administered every four weeks as a subcutaneous injection in psoriatic arthritis: Twenty-four-week efficacy and safety results of a randomized, placebo-controlled study. Arthritis Rheum. Apr. 2009;60(4):976-86.
Marichal-Gallardo PA, Alvarez MM. State-of-the-art in downstream processing of monoclonal antibodies: process trends in design and validation. Biotechnol Prog. Jul. 2012;28(4):899-916.
Shu Rong et al., Golimumab: A New Drug Against Rheumatoid ArthritisChinese Journal of Pharmacoepidemiology, vol. 20, No. 01 (an English translation of the abstrast is appended) 2011.
Van der Heijde D, Deodhar A, Braun J, Mack M, Hsu B, Gathany TA, Inman RD, Han C; Go-Raise investigators. The effect of golimumab therapy on disease activity and health-related quality of life in patients with ankylosing spondylitis: 2-year results of the GO-RAISE trial. J Rheumatol. Jun. 2014;41(6):1095-103.
Zhuang Y, Xu Z, Frederick B, de Vries DE, Ford JA, Keen M, Doyle MK, Petty KJ, Davis HM, Zhou H. Golimumab pharmacokinetics after repeated subcutaneous and intravenous administrations in patients with rheumatoid arthritis and the effect of concomitant methotrexate: an open-label, randomized study. Clin Ther. Jan. 2012;34(1):77-90.
Zidi I, Bouaziz A, Mnif W, Bartegi A, Al-Hizab FA, Amor NB. Golimumab therapy of rheumatoid arthritis: an overview. Scand J Immunol. Aug. 2010;72(2):75-85.

\* cited by examiner

FIGURE 2A

```
TNVs        ATGGGGTTTGGGCTGAGCTGGGTTTTCCTCGTTGCTCTTTTAAGA

Q   V   Q   L   V   E   S   G   G   G   V
germline                CAGGTGCAGCTGGTGGAGTCTGGGGGAGGCGTG
TNVs        GGTGTCCAGTGT................................
TNV148(B)   GGTGTCCAGTGT.....A..........................

V   Q   P   G   R   S   L   R   L   S   C   A   A   S   G
germline    GTCCAGCCTGGGAGGTCCCTGAGACTCTCCTGTGCAGCCTCTGGA
TNVs        .............................................

F   T   F   S   S   Y   A   M   H   W   V   R   Q   A   P
germline    TTCACCTTCAGTAGCTATGCTATGCACTGGGTCCGCCAGGCTCCA
TNV14,15    .............................................
TNV148(B)   ....T........................................
TNV196      ....................C........................

G   K   G   L   E   W   V   A   V   I   S   Y   D   G   S
germline    GGCAAGGGGCTGGAGTGGGTGGCAGTTATATCATATGATGGAAGC
TNV14       ...........................A....C.T..........T
TNV15       ...........................T......T..........T
TNV148(B)   .....C.....................T.....G...........
TNV196      ...........................T..................

N   K   Y   Y   A   D   S   V   K   G   R   F   T   I   S   SEQ ID NO:7 cont'd→
germline    AATAAATACTACGCAGACTCCGTGAAGGGCCGATTCACCATCTCC  SEQ ID NO:34 cont'd→
TNV14       .GC...A.G.....G.............A.................
TNV15       ..C...A.G...................C.................
TNV148(B)   ......A.G......................................
TNV196      ......A.G.C..............................G.....
```

FIGURE 2B

```
              R   D   N   S   K   N   T   L   Y   L   Q   M   N   S   L
germline   AGAGACAATTCCAAGAACACGCTGTATCTGCAAATGAACAGCCTG
TNV14      .............................................
TNV15      ....................G........................
TNV148     ........C.....................................
TNV148B    .............................................
TNV196     ..............................T..............

R   A   E   D   T   A   V   Y   Y   C   A   R
germline   AGAGCTGAGGACACGGCTGTGTATTACTGTGCAGAGA
TNV14,15   ....................................GATCGAGGT
TNV148(B)  .....................................A
TNV196     ................T....................

Y   Y   Y   Y   Y   G   M   D   V   W
germline                     TACTACTACTACTACGGTATGGACGTCTGG
TNV14      ATATCAGCAGGTGGAA................................
TNV15      G.C..............A.T..T.........................
TNV148(B)  ...G.............A..............................
TNV196     ..TGG............A..............................

G   Q   G   T   T   V   T   V   S   S
germline   GGGCAAGGGACCACGGTCACCGTCTCCTCAG        SEQ ID NO:7
TNV14      ..C............................        SEQ ID NO:34
TNV15      ..C............................
TNV148(B)  ..C............................
TNV196     ..C..G.........................
```

FIGURE 3

```
TNVs        ATGGAAGCCCCAGCTCAGCTTCTCTTCCTCCTGCTACTCTGGCTC

E   I   V   L   T   Q   S   P   A   T
germline    GAAATTGTGTTGACACAGTCTCCAGCCACC
TNVs        CCAGATACCACCGGA................................

L   S   L   S   P   G   E   R   A   T   L   S   C   R   A
germline    CTGTCTTTGTCTCCAGGGGAAAGAGCCACCCTCTCCTGCAGGGCC
TNVs        .............................................

S   Q   S   V   S   S   Y   L   A   W   Y   Q   Q   K   P
germline    AGTCAGAGTGTTAGCAGCTACTTAGCCTGGTACCAACAGAAACCT
TNV14,15    .............................................
TNV148,196  ............TA...............................

G   Q   A   P   R   L   L   I   Y   D   A   S   N   R   A
germline    GGCCAGGCTCCCAGGCTCCTCATCTATGATGCATCCAACAGGGCC
TNVs        .............................................

T   G   I   P   A   R   F   S   G   S   G   S   G   T   D
germline    ACTGGCATCCCAGCCAGGTTCAGTGGCAGTGGGTCTGGGACAGAC
TNVs        .............................................

F   T   L   T   I   S   S   L   E   P   E   D   F   A   V
germline    TTCACTCTCACCATCAGCAGCCTAGAGCCTGAAGATTTTGCAGTT
TNVs        .............................................

Y   Y   C   Q   Q   R   S   N   W   P   P   F   T   F   G      SEQ ID NO:8
Germline    TATTACTGTCAGCAGCGTAGCAACTGGCCTCCATTCACTTTCGGC                     SEQ ID NO:35
TNVs        ...............................A.............

P   G   T   K   V   D   I   K   R
germline    CCTGGGACCAAAGTGGATATCAAACGT
TNVs        ...........................
```

FIGURE 4

```
germline    MGFGLSWVFLVALLRGVQC                     signal      SEQ ID NO. 32
TNVs        ...................

germline    QVQLVESGGGVVQPGRSLRLSCAASGFTFS          FR1         SEQ ID NO. 7
TNVs        ..............................
TNV148(B)   ...........................I..

germline    SYAMH                                   CDR1        SEQ ID NO. 1
TNVs        .....

germline    WVRQAPGKGLEWVA                          FR2         SEQ ID NO. 7
TNVs        .............
TNV148(B)   .......N.....

germline    VISYDGSNKYYADSVKG                       CDR2        SEQ ID NO. 2
TNV14       I.L...S.K......D
TNV15       F.L......K......
TNV148(B)   FM.......K......
TNV196      F........KS.....

germline    RFTISRDNSKNTLYLQMNSLRAEDTAVYYCAR         FR3         SEQ ID NO. 7
TNV14       ...............................
TNV15       ..............A................
TNV148      ........P......................
TNV148B     ...............................
TNV196      ...V........F..............F....

germline    --------YYYYYGMDV
TNV14       DRGISAGGN........                       CDR3        SEQ ID NO. 3
TNV15       ...V....N........
TNV148(B)   ....A...N........
TNV196      ....G...N........

germline    WGQGTTVTVSS                             J6          SEQ ID NO. 7
TNVs        ...........
```

FIGURE 5

| | | | |
|---|---|---|---|
| TNVs | MEAPAQLLFLLLLWLPDTTG | signal | SEQ ID NO. 33 |
| germline | EIVLTQSPATLSLSPGERATLSC | FR1 | SEQ ID NO. 8 |
| TNVs | ....................... | | |
| germline | RASQSVSSYLA | CDR1 | SEQ ID NO. 4 |
| TNV14 | ........... | | |
| TNV15 | ........... | | |
| TNV148(B) | ......Y.... | | |
| TNV196 | ......Y.... | | |
| germline | WYQQKPGQAPRLLIY | FR2 | SEQ ID NO. 8 |
| TNVs | ............... | | |
| germline | DASNRAT | CDR2 | SEQ ID NO. 5 |
| TNVs | ....... | | |
| germline | GIPARFSGSGSGTDFTLTISSLEPEDFAVYYC | FR3 | SEQ ID NO. 8 |
| TNVs | ............................... | | |
| germline | QQRSNWPPFT | CDR3 | SEQ ID NO. 6 |
| TNVs | .......... | | |
| germline | FGPGTKVDIK | J3 | SEQ ID NO. 8 |
| TNVs | .......... | | |

FIGURE 9
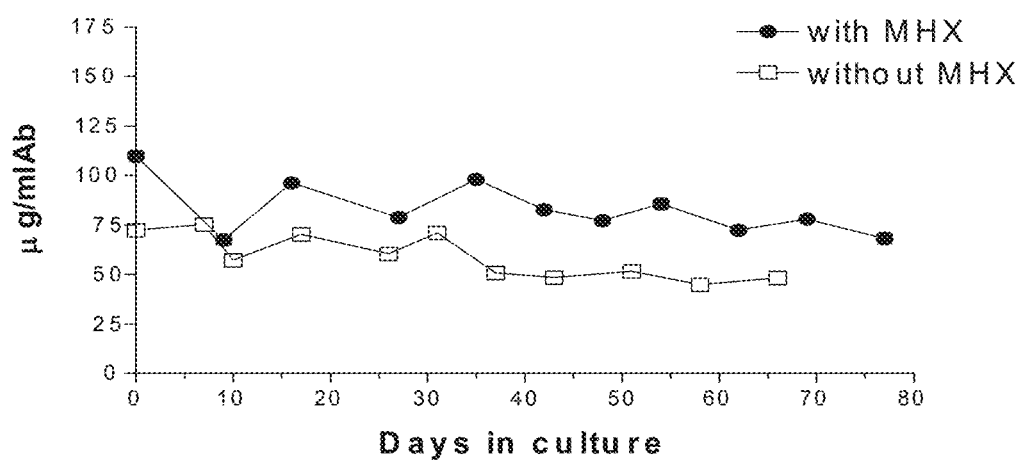
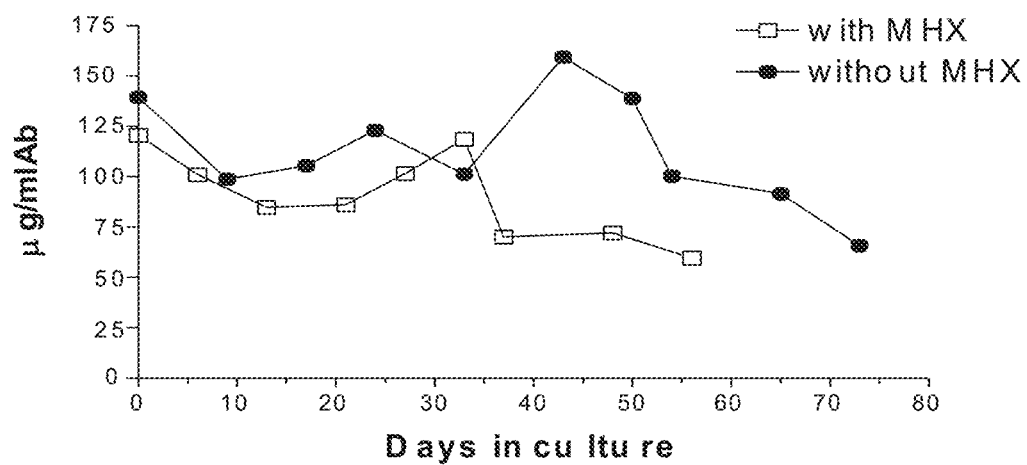

SEQUENCE LISTING

```
<160> NUMBER OF SEQ ID NOS: 37

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Heavy Chain complementarity determining region
      1 (CDR1).

<400> SEQUENCE: 1

Ser Tyr Ala Met His
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      2 (CDR2).
<220> FEATURE:
<221> NAME/KEY: MISC_FEATURE
<222> LOCATION: (1)..(1)
<223> OTHER INFORMATION: Xaa at position 1 is selected from Ile, Phe or
      Val.
<220> FEATURE:
<221> NAME/KEY: MISC_FEATURE
<222> LOCATION: (2)..(2)
<223> OTHER INFORMATION: Xaa at position 2 is selected from Ile or Met.
<220> FEATURE:
<221> NAME/KEY: MISC_FEATURE
<222> LOCATION: (3)..(3)
<223> OTHER INFORMATION: Xaa at position 3 is selected from Ser or Leu.
<220> FEATURE:
<221> NAME/KEY: MISC_FEATURE
<222> LOCATION: (4)..(4)
<223> OTHER INFORMATION: Xaa at position 4 is selected from Tyr or Phe.
<220> FEATURE:
<221> NAME/KEY: MISC_FEATURE
<222> LOCATION: (10)..(10)
```

```
<223> OTHER INFORMATION: Xaa at position 10 is selected from Lys or Tyr.
<220> FEATURE:
<221> NAME/KEY: MISC_FEATURE
<222> LOCATION: (11)..(11)
<223> OTHER INFORMATION: Xaa at position 11 is selected from Ser or Tyr.
<220> FEATURE:
<221> NAME/KEY: MISC_FEATURE
<222> LOCATION: (17)..(17)
<223> OTHER INFORMATION: Xaa at position 17 is selected from Asp or Gly.

<400> SEQUENCE: 2

Xaa Xaa Xaa Xaa Asp Gly Ser Asn Lys Xaa Xaa Ala Asp Ser Val Lys
1               5                   10                  15

Xaa

<210> SEQ ID NO 3
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Heavy Chain complementarity determining region
      3 (CDR3).
<220> FEATURE:
<221> NAME/KEY: MISC_FEATURE
<222> LOCATION: (4)..(4)
<223> OTHER INFORMATION: Xaa at position 4 is selected from Ile or Val.
<220> FEATURE:
<221> NAME/KEY: MISC_FEATURE
<222> LOCATION: (5)..(5)
<223> OTHER INFORMATION: Xaa at position 5 is selected from Ser, Ala or
      Gly.
<220> FEATURE:
<221> NAME/KEY: MISC_FEATURE
<222> LOCATION: (9)..(9)
<223> OTHER INFORMATION: Xaa at position 9 is selected from Asn or Tyr.

<400> SEQUENCE: 3

Asp Arg Gly Xaa Xaa Ala Gly Gly Xaa Tyr Tyr Tyr Tyr Gly Met Asp
1               5                   10                  15

Val

<210> SEQ ID NO 4
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: Light Chain complementarity determining region
      1 (CDR1).
<220> FEATURE:
<221> NAME/KEY: MISC_FEATURE
<222> LOCATION: (7)..(7)
<223> OTHER INFORMATION: Xaa at position 7 is selected from Ser or Tyr.

<400> SEQUENCE: 4

Arg Ala Ser Gln Ser Val Xaa Ser Tyr Leu Ala
1               5                   10

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Light Chain complementarity determining region
      2 (CDR2).
```

```
<400> SEQUENCE: 5

Asp Ala Ser Asn Arg Ala Thr
1               5

<210> SEQ ID NO 6
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: Light Chain complementarity determining region
      3 (CDR3).

<400> SEQUENCE: 6

Gln Gln Arg Ser Asn Trp Pro Pro Phe Thr
1               5                   10

<210> SEQ ID NO 7
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: heavy chain variable region sequences as
      presented in original Figure 4
<220> FEATURE:
<221> NAME/KEY: MISC_FEATURE
<222> LOCATION: (1)..(30)
<223> OTHER INFORMATION: framework 1
<220> FEATURE:
<221> NAME/KEY: MISC_FEATURE
<222> LOCATION: (28)..(28)
<223> OTHER INFORMATION: Xaa at position 28 is selected from Ile or Thr.
<220> FEATURE:
<221> NAME/KEY: MISC_FEATURE
<222> LOCATION: (31)..(35)
<223> OTHER INFORMATION: complementarity determining region 1 (CDR1).
<220> FEATURE:
<221> NAME/KEY: MISC_FEATURE
<222> LOCATION: (36)..(49)
<223> OTHER INFORMATION: framework 2
<220> FEATURE:
<221> NAME/KEY: MISC_FEATURE
<222> LOCATION: (43)..(43)
<223> OTHER INFORMATION: Xaa at position 43 is selected from Lys or Asn.
<220> FEATURE:
<221> NAME/KEY: MISC_FEATURE
<222> LOCATION: (50)..(66)
<223> OTHER INFORMATION: complementarity determining region 2 (CDR2).
<220> FEATURE:
<221> NAME/KEY: MISC_FEATURE
<222> LOCATION: (50)..(50)
<223> OTHER INFORMATION: Xaa at position 50 is selected from Ile, Phe or
      Val.
<220> FEATURE:
<221> NAME/KEY: MISC_FEATURE
<222> LOCATION: (51)..(51)
<223> OTHER INFORMATION: Xaa at position 51 is selected from Ile or Met.
<220> FEATURE:
<221> NAME/KEY: MISC_FEATURE
<222> LOCATION: (52)..(52)
<223> OTHER INFORMATION: Xaa at position 52 is selected from Ser or Leu.
<220> FEATURE:
<221> NAME/KEY: MISC_FEATURE
<222> LOCATION: (53)..(53)
<223> OTHER INFORMATION: Xaa at position 53 is selected from Tyr or Phe.
<220> FEATURE:
<221> NAME/KEY: MISC_FEATURE
<222> LOCATION: (59)..(59)
<223> OTHER INFORMATION: Xaa at position 59 is selected from Lys or Tyr.
<220> FEATURE:
<221> NAME/KEY: MISC_FEATURE
<222> LOCATION: (60)..(60)
```

```
<223> OTHER INFORMATION: Xaa at position 60 is selected from Ser or Tyr.
<220> FEATURE:
<221> NAME/KEY: MISC_FEATURE
<222> LOCATION: (66)..(66)
<223> OTHER INFORMATION: Xaa at position 66 is selected from Asp or Gly.
<220> FEATURE:
<221> NAME/KEY: MISC_FEATURE
<222> LOCATION: (67)..(98)
<223> OTHER INFORMATION: framework 3
<220> FEATURE:
<221> NAME/KEY: MISC_FEATURE
<222> LOCATION: (70)..(70)
<223> OTHER INFORMATION: Xaa at position 70 is selected from Val or Ile.
<220> FEATURE:
<221> NAME/KEY: MISC_FEATURE
<222> LOCATION: (75)..(75)
<223> OTHER INFORMATION: Xaa at position 75 is selected from Ser or Pro.
<220> FEATURE:
<221> NAME/KEY: MISC_FEATURE
<222> LOCATION: (78)..(78)
<223> OTHER INFORMATION: Xaa at position 78 is selected from Thr or Ala.
<220> FEATURE:
<221> NAME/KEY: MISC_FEATURE
<222> LOCATION: (80)..(80)
<223> OTHER INFORMATION: Xaa at position 80 is selected from Tyr or Phe.
<220> FEATURE:
<221> NAME/KEY: MISC_FEATURE
<222> LOCATION: (94)..(94)
<223> OTHER INFORMATION: Xaa at position 94 is selected from Tyr or Phe.
<220> FEATURE:
<221> NAME/KEY: MISC_FEATURE
<222> LOCATION: (99)..(115)
<223> OTHER INFORMATION: complementarity determining region 3 (CDR3).
<220> FEATURE:
<221> NAME/KEY: MISC_FEATURE
<222> LOCATION: (102)..(102)
<223> OTHER INFORMATION: Xaa at position 102 is selected from Ile or
      Val.
<220> FEATURE:
<221> NAME/KEY: MISC_FEATURE
<222> LOCATION: (116)..(126)
<223> OTHER INFORMATION: J6 region

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Xaa Phe Ser Ser Tyr
            20                  25                  30

Ala Met His Trp Val Arg Gln Ala Pro Gly Xaa Gly Leu Glu Trp Val
        35                  40                  45

Ala Xaa Xaa Xaa Xaa Asp Gly Ser Asn Lys Xaa Xaa Ala Asp Ser Val
    50                  55                  60

Lys Xaa Arg Phe Thr Xaa Ser Arg Asp Asn Xaa Lys Asn Xaa Leu Xaa
65                  70                  75                  80

Leu Gln Met Asn Ser Leu Arg Ala Glu Asp Thr Ala Val Xaa Tyr Cys
                85                  90                  95

Ala Arg Asp Arg Gly Xaa Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 8
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: light chain variable region sequences as
      presented in original Figure 5
```

```
<220> FEATURE:
<221> NAME/KEY: MISC_FEATURE
<222> LOCATION: (1)..(23)
<223> OTHER INFORMATION: framework 1
<220> FEATURE:
<221> NAME/KEY: MISC_FEATURE
<222> LOCATION: (24)..(34)
<223> OTHER INFORMATION: complementarity determining region 1 (CDR1).
<220> FEATURE:
<221> NAME/KEY: MISC_FEATURE
<222> LOCATION: (35)..(49)
<223> OTHER INFORMATION: framework 2
<220> FEATURE:
<221> NAME/KEY: MISC_FEATURE
<222> LOCATION: (50)..(56)
<223> OTHER INFORMATION: complementarity determining region 2 (CDR2).
<220> FEATURE:
<221> NAME/KEY: MISC_FEATURE
<222> LOCATION: (57)..(88)
<223> OTHER INFORMATION: framework 3
<220> FEATURE:
<221> NAME/KEY: MISC_FEATURE
<222> LOCATION: (89)..(98)
<223> OTHER INFORMATION: complementarity determining region 3 (CDR3).
<220> FEATURE:
<221> NAME/KEY: MISC_FEATURE
<222> LOCATION: (99)..(108)
<223> OTHER INFORMATION: J3 region

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 9
<211> LENGTH: 157
<212> TYPE: PRT
<213> ORGANISM: Homo sapiens
<220> FEATURE:
<221> NAME/KEY: MISC_FEATURE
<222> LOCATION: (1)..(157)
<223> OTHER INFORMATION: human TNF alpha monomer sequence

<400> SEQUENCE: 9

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80
```

```
Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155
```

```
<210> SEQ ID NO 10
<211> LENGTH: 18
<212> TYPE: DNA
<213> ORGANISM: Homo sapiens

<400> SEQUENCE: 10
ttggtccagt cggactgg                                                18

<210> SEQ ID NO 11
<211> LENGTH: 18
<212> TYPE: DNA
<213> ORGANISM: Homo sapiens

<400> SEQUENCE: 11
cacctgcact cggtgctt                                                18

<210> SEQ ID NO 12
<211> LENGTH: 30
<212> TYPE: DNA
<213> ORGANISM: Homo sapiens

<400> SEQUENCE: 12
cactgttttg agtgtgtacg ggcttaagtt                                   30

<210> SEQ ID NO 13
<211> LENGTH: 18
<212> TYPE: DNA
<213> ORGANISM: Homo sapiens

<400> SEQUENCE: 13
gccgcacgtg tggaaggg                                                18

<210> SEQ ID NO 14
<211> LENGTH: 25
<212> TYPE: DNA
<213> ORGANISM: Homo sapiens

<400> SEQUENCE: 14
agtcaaggtc ggactggctt aagtt                                        25

<210> SEQ ID NO 15
<211> LENGTH: 28
<212> TYPE: DNA
<213> ORGANISM: Homo sapiens

<400> SEQUENCE: 15
gttgtcccct ctcacaatct tcgaattt                                     28

<210> SEQ ID NO 16
<211> LENGTH: 18
<212> TYPE: DNA
```

<213> ORGANISM: Homo sapiens

<400> SEQUENCE: 16
ggcggtagac tactcgtc                                                  18

<210> SEQ ID NO 17
<211> LENGTH: 7
<212> TYPE: PRT
<213> ORGANISM: Homo sapiens

<400> SEQUENCE: 17

Met Asp Trp Thr Trp Ser Ile
1               5

<210> SEQ ID NO 18
<211> LENGTH: 35
<212> TYPE: DNA
<213> ORGANISM: Homo sapiens

<400> SEQUENCE: 18
tttcgtacgc caccatggac tggacctgga gcatc                               35

<210> SEQ ID NO 19
<211> LENGTH: 34
<212> TYPE: DNA
<213> ORGANISM: Homo sapiens

<400> SEQUENCE: 19
tttcgtacgc caccatgggg tttgggctga gctg                                34

<210> SEQ ID NO 20
<211> LENGTH: 35
<212> TYPE: DNA
<213> ORGANISM: Homo sapiens

<400> SEQUENCE: 20
tttcgtacgc caccatggag tttgggctga gcatg                               35

<210> SEQ ID NO 21
<211> LENGTH: 35
<212> TYPE: DNA
<213> ORGANISM: Homo sapiens

<400> SEQUENCE: 21
tttcgtacgc caccatgaaa cacctgtggt tcttc                               35

<210> SEQ ID NO 22
<211> LENGTH: 35
<212> TYPE: DNA
<213> ORGANISM: Homo sapiens

<400> SEQUENCE: 22
tttcgtacgc caccatgggg tcaaccgcca tcctc                               35

<210> SEQ ID NO 23
<211> LENGTH: 6
<212> TYPE: PRT
<213> ORGANISM: Homo sapiens

<400> SEQUENCE: 23

Thr Val Thr Val Ser Ser
1               5

```
<210> SEQ ID NO 24
<211> LENGTH: 36
<212> TYPE: DNA
<213> ORGANISM: Homo sapiens

<400> SEQUENCE: 24
gtgccagtgg cagaggagtc cattcaagct taagtt                                36

<210> SEQ ID NO 25
<211> LENGTH: 5
<212> TYPE: PRT
<213> ORGANISM: Homo sapiens

<400> SEQUENCE: 25

Met Asp Met Arg Val
1               5

<210> SEQ ID NO 26
<211> LENGTH: 31
<212> TYPE: DNA
<213> ORGANISM: Homo sapiens

<400> SEQUENCE: 26
tttgtcgaca ccatggacat gagggtcctc c                                     31

<210> SEQ ID NO 27
<211> LENGTH: 28
<212> TYPE: DNA
<213> ORGANISM: Homo sapiens

<400> SEQUENCE: 27
tttgtcgaca ccatggaagc cccagctc                                         28

<210> SEQ ID NO 28
<211> LENGTH: 6
<212> TYPE: PRT
<213> ORGANISM: Homo sapiens

<400> SEQUENCE: 28

Thr Lys Val Asp Ile Lys
1               5

<210> SEQ ID NO 29
<211> LENGTH: 41
<212> TYPE: DNA
<213> ORGANISM: Homo sapiens

<400> SEQUENCE: 29
ctggtttcac ctatagtttg cattcagaat tcggcgcctt t                          41

<210> SEQ ID NO 30
<211> LENGTH: 35
<212> TYPE: DNA
<213> ORGANISM: Homo sapiens

<400> SEQUENCE: 30
catctccaga gacaattcca agaacacgct gtatc                                 35

<210> SEQ ID NO 31
<211> LENGTH: 35
<212> TYPE: DNA
<213> ORGANISM: Homo sapiens

<400> SEQUENCE: 31
```
gtagaggtct ctgttaaggt tcttgtgcga catag       35

<210> SEQ ID NO 32
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Signal sequence for heavy chain variable region
      sequences as presented in original Figure 4

<400> SEQUENCE: 32

Met Gly Phe Gly Leu Ser Trp Val Phe Leu Val Ala Leu Leu Arg Gly
1               5                   10                  15

Val Gln Cys

<210> SEQ ID NO 33
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: Signal sequence for light chain variable region
      sequences as presented in original Figure 5

<400> SEQUENCE: 33

Met Glu Ala Pro Ala Gln Leu Leu Phe Leu Leu Leu Leu Trp Leu Pro
1               5                   10                  15

Asp Thr Thr Gly
            20

<210> SEQ ID NO 34
<211> LENGTH: 428
<212> TYPE: DNA
<213> ORGANISM: Homo sapiens
<220> FEATURE:
<221> NAME/KEY: MISC_FEATURE
<223> OTHER INFORMATION: heavy chain variable region DNA sequences as
      presented in original Figure 2A-2B with coding sequence 1 to 421

<400> SEQUENCE: 34
atggggtttg gctgagctg ggttttcctc gttgctcttt taagaggtgt ccagtgtcag      60
gtgcagctgg tggagtctgg gggaggcgtg gtccagcctg ggaggtccct gagactctcc    120
tgtgcagcct ctggttcacc ttcagtagct atgctatgca ctgggtccgc caggctccgg    180
caaggggctg gagtgggtgg cagttatatc atatgatgga aataaatac tacgcagact     240 ccgtgaaggg ccgattcacc atctagagac aattccaaga acacgctgta tctgcaaatg    300
aacagccaga gctgaggaca cggctgtgta ttactgtgcg agagatcgag gtatatcagc    360
aggtggaata ctactactac tacggtatgg acgtctgggg gcaagggacc acggtcaccg    420
tctcctca                                                              428

<210> SEQ ID NO 35
<211> LENGTH: 387
<212> TYPE: DNA
<213> ORGANISM: Homo sapiens
<220> FEATURE:
<221> NAME/KEY: MISC_FEATURE
<223> OTHER INFORMATION: light chain variable region DNA sequences as
      presented in original Figure 3 with coding sequence 1 to 387

<400> SEQUENCE: 35

```
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggcctccatt cactttcggc     360
cctgggacca aagtggatat caaacgt                                         387
```

<210> SEQ ID NO 36
<211> LENGTH: 456
<212> TYPE: PRT
<213> ORGANISM: Homo sapiens
<220> FEATURE:
<221> NAME/KEY: MISC_FEATURE
<222> LOCATION: (1)..(456)
<223> OTHER INFORMATION: Golimumab Heavy Chain (HC)

<400> SEQUENCE: 36

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285
```

```
Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 37
<211> LENGTH: 215
<212> TYPE: PRT
<213> ORGANISM: Homo sapiens
<220> FEATURE:
<221> NAME/KEY: MISC_FEATURE
<222> LOCATION: (1)..(215)
<223> OTHER INFORMATION: Golimumab Light Chain (LC)

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
-continued

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

ANTI-TNF ANTIBODIES, COMPOSITIONS, AND METHODS FOR THE TREATMENT OF ACTIVE ANKYLOSING SPONDYLITIS

CROSS REFERENCE TO RELATED APPLICATIONS

This application is a continuation application of U.S. Ser. No. 16/517,594, filed Jul. 20, 2019, which is a continuation application of U.S. Ser. No. 15/818,063, filed Nov. 20, 2017, which claims priority to U.S. Ser. No. 62/452,079, filed Jan. 30, 2017, the contents of which are hereby incorporated by reference in their entirety.

FIELD OF THE INVENTION

The present invention relates to compositions and methods utilizing anti-TNF antibodies having a heavy chain (HC) comprising SEQ ID NO:36 and a light chain (LC) comprising SEQ ID NO:37 for use in the safe and effective treatment of active Psoriatic Arthritis (PsA).

BACKGROUND OF THE INVENTION

TNF alpha is a soluble homotrimer of 17 kD protein subunits. A membrane-bound 26 kD precursor form of TNF also exists.

Cells other than monocytes or macrophages also produce TNF alpha. For example, human non-monocytic tumor cell lines produce TNF alpha and CD4+ and CD8+ peripheral blood T lymphocytes and some cultured T and B cell lines also produce TNF alpha.

TNF alpha causes pro-inflammatory actions which result in tissue injury, such as degradation of cartilage and bone, induction of adhesion molecules, inducing procoagulant activity on vascular endothelial cells, increasing the adherence of neutrophils and lymphocytes, and stimulating the release of platelet activating factor from macrophages, neutrophils and vascular endothelial cells.

TNF alpha has been associated with infections, immune disorders, neoplastic pathologies, autoimmune pathologies and graft-versus-host pathologies. The association of TNF alpha with cancer and infectious pathologies is often related to the host's catabolic state. Cancer patients suffer from weight loss, usually associated with anorexia.

The extensive wasting which is associated with cancer, and other diseases, is known as "cachexia". Cachexia includes progressive weight loss, anorexia, and persistent erosion of lean body mass in response to a malignant growth. The cachectic state causes much cancer morbidity and mortality. There is evidence that TNF alpha is involved in cachexia in cancer, infectious pathology, and other catabolic states.

TNF alpha is believed to play a central role in gram-negative sepsis and endotoxic shock, including fever, malaise, anorexia, and cachexia. Endotoxin strongly activates monocyte/macrophage production and secretion of TNF alpha and other cytokines. TNF alpha and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNF alpha increases in patients suffering from Gram-negative sepsis.

Thus, TNF alpha has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. Beneficial effects in open-label trials with a chimeric monoclonal antibody to TNF alpha (cA2) have been reported with suppression of inflammation and with successful retreatment after relapse in rheumatoid arthritis and in Crohn's disease. Beneficial results in a randomized, double-blind, placebo-controlled trial with cA2 have also been reported in rheumatoid arthritis with suppression of inflammation.

Other investigators have described mAbs specific for recombinant human TNF which had neutralizing activity in vitro. Some of these mAbs were used to map epitopes of human TNF and develop enzyme immunoassays and to assist in the purification of recombinant TNF. However, these studies do not provide a basis for producing TNF neutralizing antibodies that can be used for in vivo diagnostic or therapeutic uses in humans, due to immunogenicity, low specificity and/or pharmaceutical unsuitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems.

Putative receptor binding loci of hTNF has been disclosed and the receptor binding loci of TNF alpha as consisting of amino acids 11-13, 37-42, 49-57 and 155-157 of TNF have been disclosed.

Non-human mammalian, chimeric, polyclonal (e.g., antisera) and/or monoclonal antibodies (Mabs) and fragments (e.g., proteolytic digestion or fusion protein products thereof) are potential therapeutic agents that are being investigated in some cases to attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the readministration of the antibody or fragment. For example, repeated administration of antibodies or fragments comprising non-human portions can lead to serum sickness and/or anaphylaxis. In order to avoid these and other problems, a number of approaches have been taken to reduce the immunogenicity of such antibodies and portions thereof, including chimerization and humanization, as well known in the art. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins.

Accordingly, there is a need to provide anti-TNF antibodies or fragments that overcome one more of these problems, as well as improvements over known antibodies or fragments thereof.

SUMMARY OF THE INVENTION

The present invention provides at least one isolated mammalian anti-TNF antibody having a heavy chain (HC) comprising SEQ ID NO:36 and a light chain (LC) comprising SEQ ID NO:37 for use in the safe and effective treatment of active Psoriatic Arthritis, wherein said anti-TNF antibody is administered via intravenous (IV) infusion, and wherein at week 14 of treatment patients treated with the anti-TNF antibody achieve a mean change from baseline in one or more criteria selected from the group consisting of: Health Assessment Questionnaire Disability Index score (HAQ-DI)=−0.60±0.53 standard deviation (SD), enthesitis=−1.87±1.75 SD, dactylitis=−7.8±8.57 SD, 36-item Short-Form Health Survey Physical Summary score (SF-36 PCS)=8.65±7.60 SD, and 36-item Short-Form Health Survey Mental Component Summary score (SF-36 MCS)=5.33±9.95 SD.

The present invention provides at least one isolated mammalian anti-TNF antibody having a heavy chain (HC) comprising SEQ ID NO:36 and a light chain (LC) comprising SEQ ID NO:37 for use in the safe and effective treatment of active Psoriatic Arthritis, wherein said anti-TNF antibody is administered via intravenous (IV) infusion at a dose of 2 mg/kg over 30±10 minutes at Weeks 0 and 4, and then every 8 weeks (q8w) thereafter, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered via IV infusion, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered via IV infusion at a dose of 2 mg/kg over 30±10 minutes at Weeks 0 and 4, then every 8 weeks (q8w) thereafter, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered with or without MTX and the composition is administered via IV infusion, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion at a dose of 2 mg/kg over 30±10 minutes at Weeks 0 and 4, then every 8 weeks (q8w) thereafter, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33=9.95 SD.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered with or without MTX, and wherein said composition is administered via IV infusion at a dose of 2 mg/kg over 30±10 minutes at Weeks 0 and 4, then every 8 weeks (q8w) thereafter, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion, and wherein at week 14 of treatment patients treated with the anti-TNF antibody achieve a mean change from baseline in one or more criteria selected from the group consisting of: HAQ-DI=−0.60±0.53 SD, enthesitis=−1.87±1.75 SD, dactylitis=−7.8±8.57 SD, SF-36 PCS=8.65±7.60 SD, and SF-36 MCS=5.33±9.95 SD, the method further comprising administering, prior, concurrently or after said (a) administering, at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

The present invention provides at least one isolated mammalian anti-TNF antibody having a heavy chain (HC) comprising SEQ ID NO:36 and a light chain (LC) comprising SEQ ID NO:37 for use in the safe and effective treatment of active Psoriatic Arthritis, wherein said anti-TNF antibody is administered via intravenous (IV) infusion, and wherein at week 24 of treatment patients treated with the anti-TNF antibody achieve a mean change from baseline in total modified van der Heijde-Sharp score (vdH-S)=−0.36±0.144 Standard error (SE).

The present invention provides at least one isolated mammalian anti-TNF antibody having a heavy chain (HC) comprising SEQ ID NO:36 and a light chain (LC) comprising SEQ ID NO:37 for use in the safe and effective treatment of active Psoriatic Arthritis, wherein said anti-TNF antibody is administered via intravenous (IV) infusion at a dose of 2 mg/kg over 30±10 minutes at Weeks 0 and 4, and then every 8 weeks (q8w) thereafter, and wherein at week 24 of treatment patients treated with the anti-TNF antibody achieve a mean change from baseline in vdH-S=−0.36=0.144 SE.

The present invention provides at least one isolated mammalian anti-TNF antibody having a heavy chain (HC) comprising SEQ ID NO:36 and a light chain (LC) comprising SEQ ID NO:37 for use in the safe and effective treatment of active Psoriatic Arthritis, wherein said anti-TNF antibody is administered with or without MTX and the anti-TNF antibody is administered via intravenous (IV) infusion at a dose of 2 mg/kg over 30±10 minutes at Weeks 0 and 4, and then every 8 weeks (q8w) thereafter, and wherein at week 24 of treatment patients treated with the anti-TNF antibody achieve a mean change from baseline in vdH-S=−0.36±0.144 SE.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered via IV infusion, and wherein at week 24 of treatment patients treated with the anti-TNF antibody achieve a mean change from baseline in vdH-S=−0.36±0.144 SE.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered via IV infusion at a dose of 2 mg/kg over 30±10 minutes at Weeks 0 and 4, then every 8 weeks (q8w) thereafter, and wherein at week 24 of treatment patients treated with the anti-TNF antibody achieve a mean change from baseline in vdH-S=−0.36±0.144 SE.

The present invention provides a composition comprising at least one isolated mammalian anti-TNF antibody having a heavy chain (HC) comprising SEQ ID NO:36 and a light chain (LC) comprising SEQ ID NO:37, and at least one pharmaceutically acceptable carrier or diluent for use in the safe and effective treatment of active Psoriatic Arthritis, wherein said composition is administered via IV infusion at a dose of 2 mg/kg over 30±10 minutes at Weeks 0 and 4, then every 8 weeks (q8w) thereafter, and wherein at week 24 of treatment patients treated with the anti-TNF antibody achieve a mean change from baseline in vdH-S=−0.36±0.144 SE.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion, and wherein at week 24 of treatment patients treated with the anti-TNF antibody achieve a mean change from baseline in vdH-S=−0.36±0.144 SE.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion at a dose of 2 mg/kg over 30±10 minutes at Weeks 0 and 4, then every 8 weeks (q8w) thereafter, and wherein at week 24 of treatment patients treated with the anti-TNF antibody achieve a mean change from baseline in vdH-S=−0.36±0.144 SE.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered with or without MTX, and wherein the composition is administered via IV infusion at a dose of 2 mg/kg over 30±10 minutes at Weeks 0 and 4, then every 8 weeks (q8w) thereafter, and wherein at week 24 of treatment patients treated with the anti-TNF antibody achieve a mean change from baseline in vdH-S=−0.36±0.144 SE.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered with or without MTX, and wherein the composition is administered via IV infusion at a dose of 2 mg/kg over 30±10 minutes at Weeks 0 and 4, then every 8 weeks (q8w) thereafter, and wherein at week 24 of treatment patients treated with the anti-TNF antibody achieve a mean change from baseline in vdH-S=−0.36±0.144 SE, the method further comprising administering, prior, concurrently or after said (a) administering, at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

The present invention provides at least one isolated mammalian anti-TNF antibody having a heavy chain (HC) comprising SEQ ID NO:36 and a light chain (LC) comprising SEQ ID NO:37 for use in the safe and effective treatment or prevention of active Psoriatic Arthritis, wherein said anti-TNF antibody is administered via IV infusion and induces a clinical response selected from the group consisting of the responses in the table below:

|  | Placebo | Golimumab 2 mg/kg | P-values |
|---|---|---|---|
| Patients randomized, n | 239 | 241 | |
| Clinical efficacy at wk14 | | | |
| ACR20, n (%) | 52 (21.8%) | 181 (75.1%) | p < 0.001 |
| ACR50, n (%) | 15 (6.3%) | 105 (43.6%) | p < 0.001 |
| ACR70, n (%) | 5 (2.1%) | 59 (24.5%) | p < 0.001 |
| PASI 75, n (%)* | 27/198 (13.6%) | 116/196 (59.2%) | p < 0.001 |
| Minimal Disease Activity | | | |
| MDA n/N (%) | 10/239 (4.2%) | 65/241 (27.0%) | p < 0.001 |
| Number Needed to Treat | | | |
| NNT (95% CI) | | 1.9 (1.64, 2.18) | |
| Clinical efficacy at Week 24 | | | |
| ACR50, n (%) | 15 (6.3%) | 129 (53.5%) | |

*Among pts with ≥3% BSA involvement
ACR, American College of Rheumatology Criteria; PASI, Psoriasis Area Severity Index The present invention provides at least one isolated mammalian anti-TNF antibody having a heavy chain (HC) comprising SEQ ID NO:36 and a light chain (LC) comprising SEQ ID NO:37 for use in the safe and effective treatment or prevention of active Psoriatic Arthritis, wherein said anti-TNF antibody is administered via IV infusion, and wherein ≥65% of patients receiving the treatment achieve an ACR20 at week 14 of treatment.

The present invention provides at least one isolated mammalian anti-TNF antibody having a heavy chain (HC) comprising SEQ ID NO:36 and a light chain (LC) comprising SEQ ID NO:37 for use in the safe and effective treatment or prevention of active Psoriatic Arthritis, wherein said anti-TNF antibody is administered via IV infusion at a dose of 2 mg/kg over 30±10 minutes at Weeks 0 and 4, then every 8 weeks (q8w) thereafter, and wherein ≥65% of patients receiving the treatment achieve an ACR20 at week 14 of treatment.

The present invention provides at least one isolated mammalian anti-TNF antibody having a heavy chain (HC) comprising SEQ ID NO:36 and a light chain (LC) comprising SEQ ID NO:37 for use in the safe and effective treatment or prevention of active Psoriatic Arthritis, wherein said anti-TNF antibody is administered via IV infusion at a dose of 2 mg/kg over 30±10 minutes at Weeks 0 and 4, then every 8 weeks (q8w) thereafter, and wherein ≥65% of patients receiving the treatment achieve an ACR20 at week 14 of treatment and said ≥65% of patients that achieve an ACR20 at week 14 of treatment with a treatment difference (improvement compared to placebo) of ≥50%.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion at a dose of 2 mg/kg over 30±10 minutes at Weeks 0 and 4, then every 8 weeks (q8w) thereafter, and wherein ≥65% of patients receiving the treatment achieve an ACR20 at week 14 of treatment.

The present invention provides a method for treating a TNF related condition, wherein the TNF related condition is active Psoriatic Arthritis, the method comprising: administering a composition comprising a safe and effective amount of an isolated mammalian anti-TNF antibody having a heavy chain (HC) comprising SEQ ID NO:36 and a light chain (LC) comprising SEQ ID NO:37, wherein said composition is administered via IV infusion at a dose of 2 mg/kg over 30±10 minutes at Weeks 0 and 4, then every 8 weeks (q8w) thereafter, and wherein ≥65% of patients receiving the treatment achieve an ACR20 at week 14 of treatment and said ≥65% of patients that achieve an ACR20 at week 14 of treatment with a treatment difference (improvement compared to placebo) of ≥50%.

DESCRIPTION OF THE FIGURES

FIGS. 2A-B shows DNA sequences of the TNV mAb heavy chain variable regions. The germline gene shown is the DP-46 gene. 'TNVs' indicates that the sequence shown is the sequence of TNV14, TNV15, TNV148, and TNV196. The first three nucleotides in the TNV sequence define the translation initiation Met codon. Dots in the TNV mAb gene sequences indicate the nucleotide is the same as in the germline sequence. The first 19 nucleotides (underlined) of the TNV sequences correspond to the oligonucleotide used to PCR-amplify the variable region. An amino acid translation (single letter abbreviations) starting with the mature mAb is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb heavy chains use the J6 joining region.

FIG. 3 shows DNA sequences of the TNV mAb light chain variable regions. The germline gene shown is a representative member of the Vg/38K family of human kappa germline variable region genes. Dots in the TNV mAb gene sequences indicate the nucleotide is the same as in the germline sequence. The first 16 nucleotides (underlined) of the TNV sequences correspond to the oligonucleotide used to PCR-amplify the variable region. An amino acid translation of the mature mAb (single letter abbreviations) is shown only for the germline gene. The three CDR domains in the germline amino acid translation are marked in bold and underlined. Lines labeled TNV148(B) indicate that the sequence shown pertains to both TNV148 and TNV148B. Gaps in the germline DNA sequence (CDR3) are due to the sequence not being known or not existing in the germline gene. The TNV mAb light chains use the J3 joining sequence.

FIG. 4 shows deduced amino acid sequences of the TNV mAb heavy chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the DP-46 germline gene is shown on the top line for each domain. Dots indicate that the amino acid in the TNV mAb is identical to the germline gene. TNV148(B) indicates that the sequence shown pertains to both TNV148 and TNV148B. 'TNVs' indicates that the sequence shown pertains to all TNV mAbs unless a different sequence is shown. Dashes in the germline sequence (CDR3) indicate that the sequences are not known or do not exist in the germline gene.

FIG. 5 shows deduced amino acid sequences of the TNV mAb light chain variable regions. The amino acid sequences shown (single letter abbreviations) were deduced from DNA sequence determined from both uncloned PCR products and cloned PCR products. The amino sequences are shown partitioned into the secretory signal sequence (signal), framework (FW), and complementarity determining region (CDR) domains. The amino acid sequence for the Vg/38K-type light chain germline gene is shown on the top line for each domain. Dots indicate that the amino acid in the TNV mAb is identical to the germline gene. TNV148(B) indicates that the sequence shown pertains to both TNV148 and TNV148B. 'All' indicates that the sequence shown pertains to TNV14, TNV15, TNV148, TNV148B, and TNV186.

FIG. 9 shows graphical representations of the stability of mAb production over time from two rTNV148B-producing cell lines. Cell subclones that had been in continuous culture since performing transfections and subclonings were used to start long-term serial cultures in 24-well culture dishes. Cells were cultured in I5Q media with and without MHX selection. Cells were continually passaged by splitting the cultures every 4 to 6 days to maintain new viable cultures while previous cultures were allowed to go spent. Aliquots of spent cell supernatant were collected shortly after cultures were spent and stored until the mAb concentrations were determined. An ELISA for human IgG was performed on all sample aliquots at the same time.

DESCRIPTION OF THE INVENTION

Figure 1:
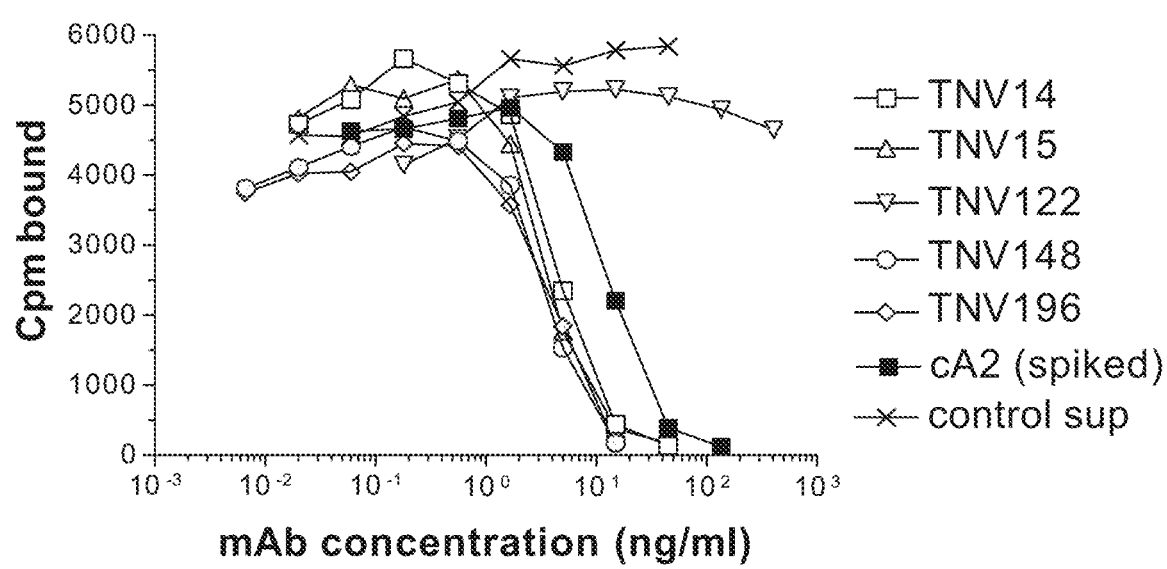
FIG. 1 shows a graphical representation showing an assay for ability of TNV mAbs in hybridoma cell supernatants to inhibit TNFα binding to recombinant TNF receptor. Varying amounts of hybridoma cell supernatants containing known amounts of TNV mAb were preincubated with a fixed concentration (5 ng/ml) of $^{125}$I-labeled TNFα. The mixture was transferred to 96-well Optiplates that had been previously coated with p55-sf2, a recombinant TNF receptor/IgG fusion protein. The amount of TNFα that bound to the p55 receptor in the presence of the mAbs was determined after washing away the unbound material and counting using a gamma counter. Although eight TNV mAb samples were tested in these experiments, for simplicity three of the mAbs that were shown by DNA sequence analyses to be identical to one of the other TNV mAbs (see Section 5.2.2) are not shown here. Each sample was tested in duplicate. The results shown are representative of two independent experiments.
Figure 6:
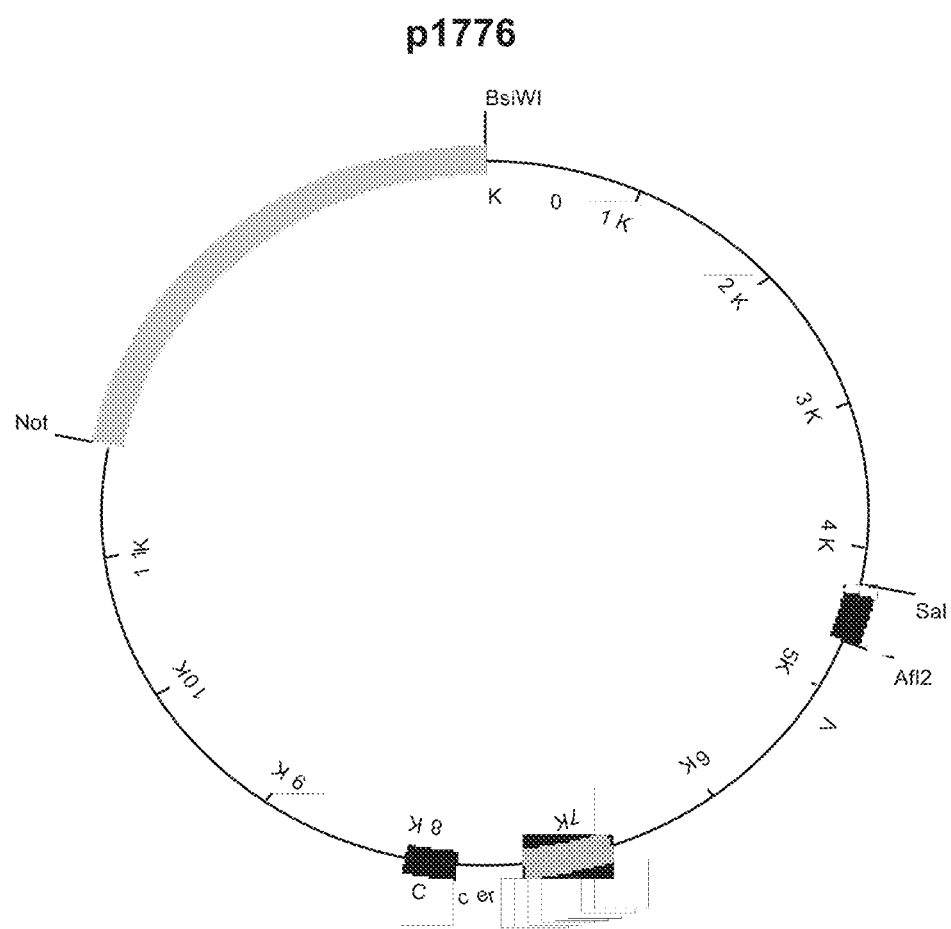
FIG. 6 shows schematic illustrations of the heavy and light chain expression plasmids used to make the rTNV148B-expressing C466 cells. p1783 is the heavy chain plasmid and p1776 is the light chain plasmid. The rTNV148B variable and constant region coding domains are shown as black boxes. The immunoglobulin enhancers in the J-C introns are shown as gray boxes. Relevant restriction sites are shown. The plasmids are shown oriented such that transcription of the Ab genes proceeds in a clockwise direction. Plasmid p1783 is 19.53 kb in length and plasmid p1776 is 15.06 kb in length. The complete nucleotide sequences of both plasmids are known. The variable region coding sequence in p1783 can be easily replaced with another heavy chain variable region sequence by replacing the BsiWI/BstBI restriction fragment. The variable region coding sequence in p1776 can be replaced with another variable region sequence by replacing the SalI/AflII restriction fragment.

The present invention provides isolated, recombinant and/or synthetic anti-TNF human, primate, rodent, mammalian, chimeric, humanized or CDR-grafted, antibodies comprising all of the heavy chain variable CDR regions of SEQ ID NOS: 1, 2 and 3 and/or all of the light chain variable CDR regions of SEQ ID NOS:4, 5 and 6 and TNF anti-idiotype antibodies thereto, as well as compositions and encoding nucleic acid molecules comprising at least one polynucleotide encoding at least one anti-TNF antibody or anti-idiotype antibody. The present invention further includes, but is not limited to, methods of making and using such nucleic acids and antibodies and anti-idiotype antibodies, including diagnostic and therapeutic compositions, methods and devices.

As used herein, an "anti-tumor necrosis factor alpha antibody," "anti-TNF antibody," "anti-TNF antibody portion," or "anti-TNF antibody fragment" and/or "anti-TNF antibody variant" and the like include any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an TNF receptor or binding protein, which can be incorporated into an antibody of the present invention. Such antibody optionally further affects a specific ligand, such as but not limited to where such antibody modulates, decreases, increases, antagonizes, agonizes, mitigates, alleviates, blocks, inhibits, abrogates and/or interferes with at least one TNF activity or binding, or with TNF receptor activity or binding, in vitro, in situ and/or in vivo. As a non-limiting example, a suitable anti-TNF antibody, specified portion or variant of the present invention can bind at least one TNF, or specified portions, variants or domains thereof. A suitable anti-TNF antibody, specified portion, or variant can also optionally affect at least one of TNF activity or function, such as but not limited to, RNA, DNA or protein synthesis, TNF release, TNF receptor signaling, membrane TNF cleavage, TNF activity, TNF production and/or synthesis. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian TNF. For example, antibody fragments capable of binding to TNF or portions thereof, including, but not limited to Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the CHI domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one TNF protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-TNF antibodies (also termed TNF antibodies) useful in the methods and compositions of the present invention can optionally be characterized by high affinity binding to TNF and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (less than about 300, preferably less than about 100 measured with a double antigen enzyme immunoassay) (Elliott et al., Lancet 344: 1125-1127 (1994), entirely incorporated herein by reference).

Utility: The isolated nucleic acids of the present invention can be used for production of at least one anti-TNF antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one TNF condition, selected from, but not limited to, at least one of an immune disorder or disease, a cardiovascular disorder or disease, an infectious, malignant, and/or neurologic disorder or disease.

Such a method can comprise administering an effective amount of a composition or a pharmaceutical composition comprising at least one anti-TNF antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts. Citations. All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention: At least one anti-TNF antibody of the present invention comprising all of the heavy chain variable CDR regions of SEQ ID NOS: 1, 2 and 3 and/or all of the light chain variable CDR regions of SEQ ID NOS:4, 5 and 6 can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

Human antibodies that are specific for human TNF proteins or fragments thereof can be raised against an appropriate immunogenic antigen, such as isolated and/or TNF protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, CA; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723, 323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182: 155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., Response to Office Action dated Aug. 6, 2020 but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/~pedro/research_tools.html;

www.mgen.uniheidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/~mrc7/mikeimages.html; www.antibodyresource.com/; mcb.harvard.edu/BioLinks/Immunology.html; www.immunologylink.com/; pathbox.wustl.edu/~hcenter/index.html; www.biotech.ufl.edu/~hcl/; www.pebio.com/pa/340913/340913.html; www.nal.usda.gov/awic/pubs/antibody/; www.m.ehime-u.ac.jp/~yasuhito/Elisa.html; www.biodesign.com/table.asp; www.icnet.uk/axp/facs/davies/links.html; www.biotech.ufl.edu/~fccl/protocol.html; www.isac-net.org/sites_geo.html; aximtl.imt.uni-marburg.de/~rek/AEPStart.html; baserv.uci.kun.nl/~jraats/links1.html; www.recab.uni-hd.de/immuno.bme.nwu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/~martin/abs/index.html; antibody-.bath.ac.uk/; abgen.cvm.tamu.edu/lab/wwwabgen.html; www.unizh.ch/~honegger/AHOseminar/Slide01.html; www.cryst.bbk.ac.uk/~ubcg07s/; www.nimr.mrc.ac.uk/CC/ccaewg/ccaewg.htm; www.path.cam.ac.uk/~mrc7/humanisation/TAHHP.html; www.ibt.unam.mx/vir/structure/stat_aim.html; www.biosci.missouri.edu/smithgp/index.html; www.cryst.bioc.cam.ac.uk/~fmolina/Webpages/Pept/spottech.html; www.jerini.de/fr_products.htm; www.patents.ibm.com/ibm.html.Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeven et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755: WO90/14443, WO90/14424, WO90/14430, EP 229246, each entirely incorporated herein by reference, included references cited therein.

The anti-TNF antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-TNF antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al. Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643, 768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693, 493, 5,698,417, assigned to Xoma, Colligan, supra; Ausubel, supra; or Sambrook, supra, each of the above patents and publications entirely incorporated herein by reference.

Antibodies of the present invention can also be prepared using at least one anti-TNF antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-TNF antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464: 127-147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109: 341-6 (1995); Whitelam et al., Biochem. Soc. Trans. 22:940-944 (1994); and references cited therein. See, also generally for plant expression of antibodies, but not limited to, Each of the above references is entirely incorporated herein by reference.

The antibodies of the invention can bind human TNF with a wide range of affinities ($K_D$). In a preferred embodiment, at least one human mAb of the present invention can optionally bind human TNF with high affinity. For example, a human mAb can bind human TNF with a $K_D$ equal to or less than about $10^{-7}$ M, such as but not limited to, 0.1-9.9 (or any range or value therein) $\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, NY (1984); Kuby, *Janis Immunology*, W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules. Using the information provided herein, such as the nucleotide sequences encoding at least 70-100% of the contiguous amino acids of at least one of SEQ ID NOS: 1, 2, 3, 4, 5, 6, 7, 8, specified fragments, variants or consensus sequences thereof, or a deposited vector comprising at least one of these sequences, a nucleic acid molecule of the present invention encoding at least one anti-TNF antibody comprising all of the heavy chain variable CDR regions of SEQ ID NOS:1, 2 and 3 and/or all of the light chain variable CDR regions of SEQ ID NOS:4, 5 and 6 can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS: 1-3) or light chain (e.g., SEQ ID NOS: 4-6); nucleic acid molecules comprising the coding sequence for an anti-TNF antibody or variable region (e.g., SEQ ID NOS:7,8); and nucleic acid molecules which comprise a nucleotide sequence substantially different from those described above but which, due to the degeneracy of the genetic code, still encode at least one anti-TNF antibody as described herein and/or as known in the art. Of course, the genetic code is well known in the art. Thus, it would be routine for one skilled in the art to generate such degenerate nucleic acid variants that code for specific anti-TNF antibodies of the present invention. See, e.g., Ausubel, et al., supra, and such nucleic acid variants are included in the present invention. Non-limiting examples of isolated nucleic acid molecules of the present invention include SEQ ID NOS:10, 11, 12, 13, 14, 15, corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an anti-TNF antibody can include, but are not limited to, those encoding the amino acid sequence of an antibody fragment, by itself; the coding sequence for the entire antibody or a portion thereof: the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Which Selectively Hybridize to a Polynucleotide as Described Herein. The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids. The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids. The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Nucleic Acid Screening and Isolation Methods. A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses antisense RNA to the target sequence as a template for double-stranded DNA synthesis (U.S. Pat. No. 5,130,238 to Malek, et al, with the trade name NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids. The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes. The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells. The present invention also relates to vectors that include isolated nucleic acid molecules of the present invention, host cells that are genetically engineered with the recombinant vectors, and the production of at least one anti-TNF antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63 Ag8.653, SP2/0-Ag14, 293 cells, HeLa cells and the like, which are readily available from, for example, American Type Culture Collection, Manassas, Va (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos.

5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody. An anti-TNF antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-TNF Antibodies

The isolated antibodies of the present invention, comprising all of the heavy chain variable CDR regions of SEQ ID NOS: 1, 2 and 3 and/or all of the light chain variable CDR regions of SEQ ID NOS:4, 5 and 6, comprise antibody amino acid sequences disclosed herein encoded by any suitable polynucleotide, or any isolated or prepared antibody. Preferably, the human antibody or antigen-binding fragment binds human TNF and, thereby partially or substantially neutralizes at least one biological activity of the protein. An antibody, or specified portion or variant thereof, that partially or preferably substantially neutralizes at least one biological activity of at least one TNF protein or fragment can bind the protein or fragment and thereby inhibit activities mediated through the binding of TNF to the TNF receptor or through other TNF-dependent or mediated mechanisms. As used herein, the term "neutralizing antibody" refers to an antibody that can inhibit an TNF-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-TNF antibody to inhibit an TNF-dependent activity is preferably assessed by at least one suitable TNF protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other transgenic non-human mammal comprising at least one human light chain (e.g., IgG, IgA☐ and IgM (e.g., γ1, γ2, γ3, γ4) transgenes as described herein and/or as known in the art. In another embodiment, the anti-human TNF human antibody comprises an IgG1 heavy chain and a IgG1 light chain.

At least one antibody of the invention binds at least one specified epitope specific to at least one TNF protein, subunit, fragment, portion or any combination thereof. The at least one epitope can comprise at least one antibody binding region that comprises at least one portion of said protein, which epitope is preferably comprised of at least one extracellular, soluble, hydrophilic, external or cytoplasmic portion of said protein. The at least one specified epitope can comprise any combination of at least one amino acid sequence of at least 1-3 amino acids to the entire specified portion of contiguous amino acids of the SEQ ID NO:9.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the antibody or antigen-binding fragment have the amino acid sequence of the corresponding CDR of at least one of mAb TNV148, TNV14, TNV15, TNV196, TNV118, TNV32, TNV86, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-TNF antibody can comprise at least one of a heavy or light chain variable region having a defined amino acid sequence. For example, in a preferred embodiment, the anti-TNF antibody comprises at least one of heavy chain variable region, optionally having the amino acid sequence of SEQ ID NO:7 and/or at least one light chain variable region, optionally having the amino acid sequence of SEQ ID NO:8. antibodies that bind to human TNF and that comprise a defined heavy or light chain variable region can be prepared using suitable methods, such as phage display (Katsube, Y., et al., Int J Mol. Med, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human TNF or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human TNF with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes. The amino acids that make up anti-TNF antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylalanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-TNF antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-TNF antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-TNF antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one TNF neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-TNF antibodies of the present invention can include, but are not limited to, at least one portion, sequence or combination selected from 1 to all of the contiguous amino acids of at least one of SEQ ID NOS: 1, 2, 3, 4, 5, 6.

A(n) anti-TNF antibody can further optionally comprise a polypeptide of at least one of 70-100% of the contiguous amino acids of at least one of SEQ ID NOS:7, 8.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10-100% of the number of contiguous residues in an anti-TNF antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-1000% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, CA (1996).

Anti-Idiotype Antibodies To Anti-Tnf Antibody Compositions. In addition to monoclonal or chimeric anti-TNF antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Anti-Tnf Antibody Compositions. The present invention also provides at least one anti-TNF antibody composition comprising at least one, at least two, at least three, at least four, at least five, at least six or more anti-TNF antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-TNF antibody amino acid sequence selected from the group consisting of 70-100% of the contiguous amino acids of SEQ ID NOS: 1, 2, 3, 4, 5, 6, 7, 8, or specified fragments, domains or variants thereof. Preferred anti-TNF antibody compositions include at least one or two full length, fragments, domains or variants as at least one CDR or LBR containing portions of the anti-TNF antibody sequence of 70-100% of SEQ ID NOS:1, 2, 3, 4, 5, 6, or specified fragments, domains or variants thereof. Further preferred compositions comprise 40-99% of at least one of 70-100% of SEQ ID NOS:1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-TNF antibody compositions of the present invention can further comprise at least one of any suitable and effective amount of a composition or pharmaceutical composition comprising at least one anti-TNF antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxy chloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, $2^{nd}$ Edition, Appleton and Lange, Stamford, C T (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype O157: H7), *Staphylococcus* species (e.g., *Staphylococcus aureus*,

*Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi. Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliocbacter* species, (e.g., *Heliocbacter pylori*), *Aeromonas* species (e.g., *Aeromonas sobria, Aeromonas hydrophila, Aeromonas caviae*), *Pleisomonas shigelloides, Yersinia enterocolitica, Vibrio* species (e.g., *Vibrio cholerae, Vibrio parahemolyticus*), *Klebsiella* species, *Pseudomonas aeruginosa,* and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-TNF antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, PA) 1990. Pharmaceutically acceptable carriers can be routinely selected that are suitable for the mode of administration, solubility and/or stability of the anti-TNF antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-TNF antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-TNF antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-TNF antibody, portion or variant compositions according to the invention are known in the art, e.g., as listed in "Remington: The Science & Practice of Pharmacy", $19^{th}$ ed., Williams & Williams, (1995), and in the "Physician's Desk Reference", $52^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents.

Formulations. As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-TNF antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-TNF antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-TNF antibody, and a second vial comprising an aqueous diluent of prescribed buffer or preservative, wherein said packaging material comprises a label that instructs a patient to reconstitute the at least one anti-TNF antibody in the aqueous diluent to form a solution that can be held over a period of twenty-four hours or greater.

The at least one anti-TNF antibody used in accordance with the present invention can be produced by recombinant means, including from mammalian cell or transgenic preparations, or can be purified from other biological sources, as described herein or as known in the art.

The range of at least one anti-TNF antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyols, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-TNF antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-TNF antibody and preservative in an aqueous diluent is carried out using conventional dissolution and mixing procedures. To prepare a suitable formulation, for example, a measured amount of at least one anti-TNF antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-TNF antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-TNF antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-TNF antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-TNF antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.westonmedical.com), Medi-Ject Corp (Minneapolis, MN, www.mediject.com). Recognized devices comprising a dual vial system include those pen-injector systems for reconstituting a lyophilized drug in a cartridge for delivery of the reconstituted solution such as the Humatro-Pen®.

The products presently claimed include packaging material. The packaging material provides, in addition to the information required by the regulatory agencies, the conditions under which the product can be used. The packaging material of the present invention provides instructions to the patient to reconstitute the at least one anti-TNF antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-TNF antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-TNF antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-TNF antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications. The present invention also provides a method for modulating or treating at least one TNF related disease, in a cell, tissue, organ, animal, or patient, as known in the art or as described herein, using at least one dual integrin antibody of the present invention.

The present invention also provides a method for modulating or treating at least one TNF related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, NJ (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aortic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphedema, lipedema, unstable angina, reperfusion injury, post pump syndrome, ischemia-reperfusion injury, and the like. Such a method can optionally comprise administering an effective amount of a composition or pharmaceutical composition comprising at least one anti-TNF antibody to a cell, tissue, organ, animal or patient in need of such modulation, treatment or therapy.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, *E. coli* 0157:h7, hemolytic uremic syndrome/thrombolytic thrombocytopenia purpura, malaria, dengue hemorrhagic fever, leishmaniasis, leprosy, toxic shock syndrome, streptococcal myositis, gas gangrene, *Mycobacterium tuberculosis, Mycobacterium avium intracellulare, Pneumocystis carinii* pneumonia, pelvic inflammatory disease, orchitis/epidydimitis, legionella, lyme disease, influenza a, epstein-barr virus, viral-associated hemaphagocytic syndrome, vital encephalitis/aseptic meningitis, and the like.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasiaa, and mitochondrial multi-system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, NJ (1992)

Any method of the present invention can comprise administering an effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, CT (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10} M^{-1}$. Preferred methods for determining monoclonal antibody specificity and affinity by competitive inhibition can be found in Harlow, et al., *antibodies: A Laboratory Manual*, Cold Spring Harbor Laboratory Press, Cold Spring Harbor, New York, 1988; Colligan et al., eds., *Current Protocols in Immunology*, Greene Publishing Assoc. and Wiley Interscience, New York, (1992-2000); Kozbor et al., *Immunol. Today.* 4:72-79 (1983); Ausubel et al., eds. *Current Protocols in Molecular Biology*, Wiley Interscience, New York (1987-2000); and Muller, *Meth. Enzymol.*, 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2(3): 162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules. Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNF with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2000).

Cytokines include any known cytokine. See, e.g., CopewithCytokines.com. Cytokine antagonists include, but are not limited to, any antibody, fragment or mimetic, any soluble receptor, fragment or mimetic, any small molecule antagonist, or any combination thereof.

Therapeutic Treatments. Any method of the present invention can comprise a method for treating a TNF mediated disorder, comprising administering a safe and effective amount of a composition or pharmaceutical composition comprising at least one anti-TNF antibody to a cell, tissue, organ, animal or patient in need of such modulation, treatment or therapy. Such a method can optionally further comprise co-administration or combination therapy for treating such immune diseases, wherein the administering of said at least one anti-TNF antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxy chloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antpsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist.

As used herein, the term "safe", as it relates to a composition, dose, dosage regimen, treatment or method with an anti-TNF antibody of the present invention (e.g., the anti-TNF antibody golimumab), refers to a favorable risk:benefit ratio with an acceptable frequency and/or acceptable severity of adverse events (AEs) and serious adverse events (SAEs) compared to the standard of care or to another comparator such as other anti-TNF agents. An adverse event is an untoward medical occurrence in a patient administered a medicinal product. In particular, safe as it relates to a composition, dose, dosage regimen, treatment or method with an anti-TNF antibody of the present invention refers to an acceptable frequency and/or acceptable severity of adverse events including, for example, infusion reactions, hepatobiliary laboratory abnormalities, infections including TB, and malignancies.

The terms "efficacy" and "effective" as used herein in the context of a composition, dose, dosage regimen, treatment or method refer to the effectiveness of a particular composition, dose, dosage, treatment or method with an anti-TNF antibody of the present invention (e.g., the anti-TNF antibody golimumab). Efficacy can be measured based on change in the course of the disease in response to an agent of the present invention. For example, an anti-TNF antibody of the present invention is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician or other adequately trained individual, who may make the determination based on signs, symptoms, biopsies, or other test results that indicate amelioration of clinical symptoms or any other measure of disease activity. For example, an anti-TNF antibody of the present invention may be administered to achieve an improvement in a patient's condition related to Psoriatic Arthritis (PSA). Improvement in a patient's condition related to PsA can be assessed using one or more criteria including, for example, a Health Assessment Questionnaire Disability Index score (HAQ-DI), an enthesitis assessment, a dactylitis assessment, a 36-item Short-Form Health Survey Physical Summary score (SF-36 PCS), and/or a 36-item Short-Form Health Survey Mental Component Summary score (SF-36 MCS). HAQ-DI is a 20-question instrument that assesses the degree of difficulty a person has in accomplishing tasks in 8 functional areas (dressing, arising, eating, walking, hygiene, reaching, gripping, and activities of daily living). Enthesitis can be assessed by evaluating the presence or absence of pain by applying local pressure to entheses including, e.g., the left and right lateral elbow epicondyle, the left and right medial femoral condyle, and the left and right Achilles tendon insertion. Dactylitis can be assessed for presence and severity in both hands and both feet. SF-36 is a questionnaire consisting of 8 multi-item scales that are scored and SF-36 PSA and SF-36 MCS are summary scores derived from the SF-36 that allow comparisons of the relative burden of different diseases and the relative benefit of different treatments.

Typically, treatment of pathologic conditions is effected by administering a safe and effective amount or dosage of at least one anti-TNF antibody composition that total, on average, a range from at least about 0.01 to 500 milligrams of at least one anti-TNF antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration. Many known and developed modes of administration can be used according to the present invention for administering pharmaceutically effective amounts of at least one anti-TNF antibody according to the present invention. While pulmonary administration is used in the following description, other modes of administration can be used according to the present invention with suitable results.

TNF antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration. Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery. The invention further relates to the administration of at least one anti-TNF antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-TNF antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration. For pulmonary administration, preferably at least one anti-TNF antibody composition is delivered in a particle size effective for reaching the lower airways of the lung or sinuses. According to the invention, at least one anti-TNF antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non-aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458, 135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404, 871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-TNF antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 μm, preferably about 1-5 μm, for good respirability.

Administration of TNF antibody Compositions as a Spray. A spray including TNF antibody composition protein can be produced by forcing a suspension or solution of at least one anti-TNF antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-TNF antibody composition protein delivered by a sprayer have a particle size less than about 10 μm, preferably in the range of about 1 μm to about 5 μm, and most preferably about 2 μm to about 3 μm.

Formulations of at least one anti-TNF antibody composition protein suitable for use with a sprayer typically include antibody composition protein in an aqueous solution at a concentration of about 0.1 mg to about 100 mg of at least one anti-TNF antibody composition protein per ml of solution or mg/gm, or any range or value therein, e.g., but not limited to, 0.1, 0.2, 0.3, 4, 5, 6, 7, 8, 9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as TNF antibodies, or specified portions or variants, can also be included in the formulation.

Administration of TNF antibody compositions by a Nebulizer. Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 µm, preferably in the range of about 1 µm to about 5 µm, and most preferably about 2 µm to about 3 µm.

Formulations of at least one anti-TNF antibody suitable for use with a nebulizer, either jet or ultrasonic, typically include a concentration of about 0.1 mg to about 100 mg of at least one anti-TNF antibody protein per ml of solution. The formulation can include agents such as an excipient, a buffer, an isotonicity agent, a preservative, a surfactant, and, preferably, zinc. The formulation can also include an excipient or agent for stabilization of the at least one anti-TNF antibody composition protein, such as a buffer, a reducing agent, a bulk protein, or a carbohydrate. Bulk proteins useful in formulating at least one anti-TNF antibody composition proteins include albumin, protamine, or the like. Typical carbohydrates useful in formulating at least one anti-TNF antibody include sucrose, mannitol, lactose, trehalose, glucose, or the like. The at least one anti-TNF antibody formulation can also include a surfactant, which can reduce or prevent surface-induced aggregation of the at least one anti-TNF antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of TNF antibody compositions By A Metered Dose Inhaler. In a metered dose inhaler (MDI), a propellant, at least one anti-TNF antibody, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-TNF antibody for use with a metered-dose inhaler device will generally include a finely divided powder containing at least one anti-TNF antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluroalkane-227), or the like. Preferably the propellant is a hydrofluorocarbon. The surfactant can be chosen to stabilize the at least one anti-TNF antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one anti-TNF antibody compositions via devices not described herein.

Oral Formulations and Administration. Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat.

Nos. 5,879,681 and 5,871,753 are used to deliver biologically active agents orally are known in the art.

Mucosal Formulations and Administration. For absorption through mucosal surfaces, compositions and methods of administering at least one anti-TNF antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration. For transdermal administration, the at least one anti-TNF antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations. It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a poly basic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

Example 1: Cloning and Expression of TNF Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, CA), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells. The vector pC4 is used for the expression of TNF antibody. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are transfected with these plasmids can be selected by growing the cells in a selective medium (e.g., alpha minus MEM, Life Technologies, Gaithersburg, MD) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can be used to express the TNF in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Example 2: Generation of High Affinity Human IgG Monoclonal Antibodies Reactive with Human TNF Using Transgenic Mice Summary Transgenic mice have been used that contain human heavy and light chain immunoglobulin genes to generate high affinity, completely human, monoclonal antibodies that can be used therapeutically to inhibit the action of TNF for the treatment of one or more TNF-mediated disease. (CBA/J×C57/BL6/J) $F_2$ hybrid mice containing human variable and constant region antibody transgenes for both heavy and light chains are immunized with human recombinant TNF (Taylor et al., Intl. Immunol. 6:579-591 (1993); Lonberg, et al., Nature 368:856-859 (1994); Neuberger, M., Nature Biotech. 14:826 (1996); Fishwild, et al., Nature Biotechnology 14:845-851 (1996)). Several fusions yielded one or more panels of completely human TNF reactive IgG monoclonal antibodies. The completely human anti-TNF antibodies are further characterized. All are IgG1κ. Such antibodies are found to have affinity constants somewhere between $1\times10^9$ and $9\times10^{12}$. The unexpectedly high affinities of these fully human monoclonal antibodies make them suitable candidates for therapeutic applications in TNF related diseases, pathologies or disorders.

Abbreviations. BSA—bovine serum albumin; $CO_2$—carbon dioxide; DMSO—dimethyl sulfoxide; EIA—enzyme immunoassay; FBS—fetal bovine serum; $H_2O_2$—hydrogen peroxide; HRP—horseradish peroxidase; ID—interadermal; Ig—immunoglobulin; TNF—tissue necrosis factor alpha; IP—intraperitoneal; IV—intravenous; Mab—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; v/v—volume per volume; w/v—weight per volume.

Materials and Methods

Animals. Transgenic mice that can express human antibodies are known in the art (and are commercially available (e.g., from GenPharm International, San Jose, CA; Abgenix, Freemont, CA, and others) that express human immunoglobulins but not mouse IgM or Igκ. For example, such transgenic mice contain human sequence transgenes that undergo V(D)J joining, heavy-chain class switching, and somatic mutation to generate a repertoire of human sequence immunoglobulins (Lonberg, et al., Nature 368:856-859 (1994)). The light chain transgene can be derived, e.g., in part from a yeast artificial chromosome clone that includes nearly half of the germline human Vκ region. In addition, the heavy-chain transgene can encode both human µ and human γ1 (Fishwild, et al., Nature Biotechnology 14:845-851 (1996)) and/or γ3 constant regions. Mice derived from appropriate genotypic lineages can be used in the immunization and fusion processes to generate fully human monoclonal antibodies to TNF.

Immunization. One or more immunization schedules can be used to generate the anti-TNF human hybridomas. The first several fusions can be performed after the following exemplary immunization protocol, but other similar known protocols can be used. Several 14-20 week old female and/or surgically castrated transgenic male mice are immunized IP and/or ID with 1-1000 μg of recombinant human TNF emulsified with an equal volume of TITERMAX or complete Freund's adjuvant in a final volume of 100-400 μL (e.g., 200). Each mouse can also optionally receive 1-10 μg in 100 μL physiological saline at each of 2 SQ sites. The mice can then be immunized 1-7, 5-12, 10-18, 17-25 and/or 21-34 days later IP (1-400 μg) and SQ (1-400 μg×2) with TNF emulsified with an equal volume of TITERMAX or incomplete Freund's adjuvant. Mice can be bled 12-25 and 25-40 days later by retro-orbital puncture without anticoagulant. The blood is then allowed to clot at RT for one hour and the serum is collected and titered using an TNF EIA assay according to known methods. Fusions are performed when repeated injections do not cause titers to increase. At that time, the mice can be given a final IV booster injection of 1-400 μg TNF diluted in 100 μL physiological saline. Three days later, the mice can be euthanized by cervical dislocation and the spleens removed aseptically and immersed in 10 mL of cold phosphate buffered saline (PBS) containing 100 U/mL penicillin, 100 μg/mL streptomycin, and 0.25 μg/mL amphotericin B (PSA). The splenocytes are harvested by sterilely perfusing the spleen with PSA-PBS. The cells are washed once in cold PSA-PBS, counted using Trypan blue dye exclusion and resuspended in RPMI 1640 media containing 25 mM Hepes.

Cell Fusion. Fusion can be carried out at a 1:1 to 1:10 ratio of murine myeloma cells to viable spleen cells according to known methods, e.g., as known in the art. As a non-limiting example, spleen cells and myeloma cells can be pelleted together. The pellet can then be slowly resuspended, over 30 seconds, in 1 mL of 50% (w/v) PEG/PBS solution (PEG molecular weight 1,450, Sigma) at 37° C. The fusion can then be stopped by slowly adding 10.5 mL of RPMI 1640 medium containing 25 mM Hepes (37° C.) over 1 minute. The fused cells are centrifuged for 5 minutes at 500-1500 rpm. The cells are then resuspended in HAT medium (RPMI 1640 medium containing 25 mM Hepes, 10% Fetal Clone I serum (Hyclone), 1 mM sodium pyruvate, 4 mM L-glutamine, 10 μg/mL gentamicin, 2.5% Origen culturing supplement (Fisher), 10% 653-conditioned RPMI 1640/Hepes media, 50 μM 2-mercaptoethanol, 100 μM hypoxanthine, 0.4 μM aminopterin, and 16 μM thymidine) and then plated at 200 μL/well in fifteen 96-well flat bottom tissue culture plates. The plates are then placed in a humidified 37° C. incubator containing 5% $CO_2$ and 95% air for 7-10 days.

Detection of Human IgG Anti-TNF Antibodies in Mouse Serum. Solid phase EIA's can be used to screen mouse sera for human IgG antibodies specific for human TNF. Briefly, plates can be coated with TNF at 2 μg/mL in PBS overnight. After washing in 0.15M saline containing 0.02% (v/v) Tween 20, the wells can be blocked with 1% (w/v) BSA in PBS, 200 L/well for 1 hour at RT. Plates are used immediately or frozen at −20° C. for future use. Mouse serum dilutions are incubated on the TNF coated plates at 50 μL/well at RT for 1 hour. The plates are washed and then probed with 50 μL/well HRP-labeled goat anti-human IgG, Fc specific diluted 1:30,000 in 1% BSA-PBS for 1 hour at RT. The plates can again be washed and 100 μL/well of the citrate-phosphate substrate solution (0.1M citric acid and 0.2M sodium phosphate, 0.01% $H_2O_2$ and 1 mg/mL OPD) is added for 15 minutes at RT. Stop solution (4N sulfuric acid) is then added at 25 μL/well and the OD's are read at 490 nm via an automated plate spectrophotometer.

Detection of Completely Human Immunoglobulins in Hybridoma Supernates. Growth positive hybridomas secreting fully human immunoglobulins can be detected using a suitable EIA. Briefly, 96 well pop-out plates (VWR, 610744) can be coated with 10 μg/mL goat anti-human IgG Fc in sodium carbonate buffer overnight at 4° C. The plates are washed and blocked with 1% BSA-PBS for one hour at 37°C and used immediately or frozen at −20° C. Undiluted hybridoma supernatants are incubated on the plates for one hour at 37° C. The plates are washed and probed with HRP labeled goat anti-human kappa diluted 1:10,000 in 1% BSA-PBS for one hour at 37° C. The plates are then incubated with substrate solution as described above.

Determination of Fully Human Anti-TNF Reactivity. Hybridomas, as above, can be simultaneously assayed for reactivity to TNF using a suitable RIA or other assay. For example, supernatants are incubated on goat anti-human IgG Fc plates as above, washed and then probed with radiolabeled TNF with appropriate counts per well for 1 hour at RT. The wells are washed twice with PBS and bound radiolabeled TNF is quantitated using a suitable counter.

Human IgG1κ anti-TNF secreting hybridomas can be expanded in cell culture and serially subcloned by limiting dilution. The resulting clonal populations can be expanded and cryopreserved in freezing medium (95% FBS, 5% DMSO) and stored in liquid nitrogen.

Isotyping. Isotype determination of the antibodies can be accomplished using an EIA in a format similar to that used to screen the mouse immune sera for specific titers. TNF can be coated on 96-well plates as described above and purified antibody at 2 μg/mL can be incubated on the plate for one hour at RT. The plate is washed and probed with HRP labeled goat anti-human IgG1 or HRP labeled goat anti-human IgG3 diluted at 1:4000 in 1% BSA-PBS for one hour at RT. The plate is again washed and incubated with substrate solution as described above.

Binding Kinetics of Human Anti-Human TNF Antibodies With Human TNF. Binding characteristics for antibodies can be suitably assessed using an TNF capture EIA and BIAcore technology, for example. Graded concentrations of purified human TNF antibodies can be assessed for binding to EIA plates coated with 2 μg/mL of TNF in assays as described above. The OD's can be then presented as semi-log plots showing relative binding efficiencies.

Quantitative binding constants can be obtained, e.g., as follows, or by any other known suitable method. A BIAcore CM-5 (carboxy methyl) chip is placed in a BIAcore 2000 unit. HBS buffer (0.01 M HEPES, 0.15 M NaCl, 3 mM EDTA, 0.005% v/v P20 surfactant, pH 7.4) is flowed over a flow cell of the chip at 5 μL/minute until a stable baseline is obtained. A solution (100 μL) of 15 mg of EDC (N-ethyl-N'-(3-dimethyl-aminopropyl)-carbodiimide hydrochloride) in 200 μL water is added to 100 μL of a solution of 2.3 mg of NHS (N-hydroxysuccinimide) in 200 μL water. Forty (40) μL of the resulting solution is injected onto the chip. Six μL of a solution of human TNF (15 μg/mL in 10 mM sodium acetate, pH 4.8) is injected onto the chip, resulting in an increase of ca. 500 RU. The buffer is changed to TBS/Ca/Mg/BSA running buffer (20 mM Tris, 0.15 M sodium chloride, 2 mM calcium chloride, 2 mM magnesium acetate, 0.5% Triton X-100, 25 μg/mL BSA, pH 7.4) and flowed over the chip overnight to equilibrate it and to hydrolyze or cap any unreacted succinimide esters.

Antibodies are dissolved in the running buffer at 33.33, 16.67, 8.33, and 4.17 nM. The flow rate is adjusted to 30

μL/min and the instrument temperature to 25° C. Two flow cells are used for the kinetic runs, one on which TNF had been immobilized (sample) and a second, underivatized flow cell (blank). 120 μL of each antibody concentration is injected over the flow cells at 30 μL/min (association phase) followed by an uninterrupted 360 seconds of buffer flow (dissociation phase). The surface of the chip is regenerated (tissue necrosis factor alpha/antibody complex dissociated) by two sequential injections of 30 μL each of 2 M guanidine thiocyanate.

Analysis of the data is done using BIA evaluation 3.0 or CLAMP 2.0, as known in the art. For each antibody concentration the blank sensogram is subtracted from the sample sensogram. A global fit is done for both dissociation ($k_d$, sec$^{-1}$) and association ($k_a$, mol$^{-1}$ sec$^{-1}$) and the dissociation constant ($K_D$, mol) calculated ($k_d/k_a$). Where the antibody affinity is high enough that the RUs of antibody captured are >100, additional dilutions of the antibody are run.

Results and Discussion

Generation of Anti-Human TNF Monoclonal Antibodies. Several fusions are performed and each fusion is seeded in 15 plates (1440 wells/fusion) that yield several dozen antibodies specific for human TNF. Of these, some are found to consist of a combination of human and mouse Ig chains. The remaining hybridomas secret anti-TNF antibodies consisting solely of human heavy and light chains. Of the human hybridomas all are expected to be IgG1κ.

Binding Kinetics of Human Anti-Human TNF Antibodies. ELISA analysis confirms that purified antibody from most or all of these hybridomas bind TNF in a concentration-dependent manner. FIGS. 1-2 show the results of the relative binding efficiency of these antibodies. In this case, the avidity of the antibody for its cognate antigen (epitope) is measured. It should be noted that binding TNF directly to the EIA plate can cause denaturation of the protein and the apparent binding affinities cannot be reflective of binding to undenatured protein. Fifty percent binding is found over a range of concentrations.

Quantitative binding constants are obtained using BIAcore analysis of the human antibodies and reveals that several of the human monoclonal antibodies are very high affinity with $K_D$ in the range of $1 \times 10^{-9}$ to $7 \times 10^{-12}$.

Conclusions.

Several fusions are performed utilizing splenocytes from hybrid mice containing human variable and constant region antibody transgenes that are immunized with human TNF. A set of several completely human TNF reactive IgG monoclonal antibodies of the IgG1κ isotype are generated. The completely human anti-TNF antibodies are further characterized. Several of generated antibodies have affinity constants between $1 \times 10^9$ and $9 \times 10^{12}$. The unexpectedly high affinities of these fully human monoclonal antibodies make them suitable for therapeutic applications in TNF-dependent diseases, pathologies or related conditions.

Example 3: Generation of Human IgG Monoclonal Antibodies Reactive to Human TNFα

Summary (CBA/J×C57BL/6J) F$_2$ hybrid mice (1-4) containing human variable and constant region antibody transgenes for both heavy and light chains were immunized with recombinant human TNFα. One fusion, named GenTNV, yielded eight totally human IgG1κ monoclonal antibodies that bind to immobilized recombinant human TNFα. Shortly after identification, the eight cell lines were transferred to Molecular Biology for further characterization. As these Mabs are totally human in sequence, they are expected to be less immunogenic than cA2 (Remicade) in humans.

Abbreviations. BSA—bovine serum albumin; $CO_2$—carbon dioxide; DMSO—dimethyl sulfoxide; EIA—enzyme immunoassay; FBS—fetal bovine serum; $H_2O_2$-hydrogen peroxide; HC—heavy chain; HRP—horseradish peroxidase; ID—interadermal; Ig—immunoglobulin; TNF—tissue necrosis factor alpha; IP—intraperitoneal; IV—intravenous; Mab—monoclonal antibody; OD—optical density; OPD—o-Phenylenediamine dihydrochloride; PEG—polyethylene glycol; PSA—penicillin, streptomycin, amphotericin; RT—room temperature; SQ—subcutaneous; TNFα—tumor necrosis factor alpha; v/v—volume per volume; w/v—weight per volume.

Introduction. Transgenic mice that contain human heavy and light chain immunoglobulin genes were utilized to generate totally human monoclonal antibodies that are specific to recombinant human TNFα. It is hoped that these unique antibodies can be used, as cA2 (Remicade) is used to therapeutically inhibit the inflammatory processes involved in TNFα-mediated disease with the benefit of increased serum half-life and decreased side effects relating to immunogenicity.

Materials and Methods.

Animals. Transgenic mice that express human immunoglobulins, but not mouse IgM or Igκ, have been developed by GenPharm International. These mice contain functional human antibody transgenes that undergo V(D)J joining, heavy-chain class switching and somatic mutation to generate a repertoire of antigen-specific human immunoglobulins (1). The light chain transgenes are derived in part from a yeast artificial chromosome clone that includes nearly half of the germline human Vκ locus. In addition to several VH genes, the heavy-chain (HC) transgene encodes both human μ and human γ1 (2) and/or γ3 constant regions. A mouse derived from the HCo12/KCo5 genotypic lineage was used in the immunization and fusion process to generate the monoclonal antibodies described here.

Purification of Human TNFα. Human TNFα was purified from tissue culture supernatant from C237A cells by affinity chromatography using a column packed with the TNFα receptor-Fc fusion protein (p55-sf2) (5) coupled to Sepharose 4B (Pharmacia). The cell supernatant was mixed with one-ninth its volume of 10× Dulbecco's PBS (D-PBS) and passed through the column at 4° C. at 4 mL/min. The column was then washed with PBS and the TNFα was eluted with 0.1 M sodium citrate, pH 3.5 and neutralized with 2 M Tris-HCl pH 8.5. The purified TNFα was buffer exchanged into 10 mM Tris, 0.12 M sodium chloride pH 7.5 and filtered through a 0.2 μm syringe filter.

Immunizations. A female GenPharm mouse, approximately 16 weeks old, was immunized IP (200 μL) and ID (100 μL at the base of the tail) with a total of 100 μg of TNFα (lot JG102298 or JG102098) emulsified with an equal volume of Titermax adjuvant on days 0, 12 and 28. The mouse was bled on days 21 and 35 by retro-orbital puncture without anti-coagulant. The blood was allowed to clot at RT for one hour and the serum was collected and titered using TNFα solid phase EIA assay. The fusion, named GenTNV, was performed after the mouse was allowed to rest for seven weeks following injection on day 28. The mouse, with a specific human IgG titer of 1:160 against TNFα, was then given a final IV booster injection of 50 μg TNFα diluted in 100 μL physiological saline. Three days later, the mouse was euthanized by cervical dislocation and the spleen was removed aseptically and immersed in 10 mL of cold phosphate-buffered saline (PBS) containing 100 U/mL penicillin, 100 µg/mL streptomycin, and 0.25 µg/mL amphotericin B (PSA). The splenocytes were harvested by sterilely perfusing the spleen with PSA-PBS. The cells were washed once in cold PSA-PBS, counted using a Coulter counter and resuspended in RPMI 1640 media containing 25 mM Hepes.

Cell Lines. The non-secreting mouse myeloma fusion partner, 653 was received into Cell Biology Services (CBS) group on 5-14-97 from Centocor's Product Development group. The cell line was expanded in RPMI medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of mycoplasma (Bionique Laboratories). Cells were maintained in log phase culture until fusion. They were washed in PBS, counted, and viability determined (>95%) via trypan blue dye exclusion prior to fusion.

Human TNFα was produced by a recombinant cell line, named C237A, generated in Molecular Biology at Centocor. The cell line was expanded in IMDM medium (JRH Biosciences) supplemented with 5% (v/v) FBS (Cell Culture Labs), 2 mM L-glutamine (all from JRH Biosciences), and 0.5 :g/mL mycophenolic acid, and cryopreserved in 95% FBS and 5% DMSO (Sigma), then stored in a vapor phase liquid nitrogen freezer in CBS (13). The cell bank was sterile (Quality Control Centocor, Malvern) and free of mycoplasma (Bionique Laboratories).

Cell Fusion. The cell fusion was carried out using a 1:1 ratio of 653 murine myeloma cells and viable murine spleen cells. Briefly, spleen cells and myeloma cells were pelleted together. The pellet was slowly resuspended over a 30 second period in 1 mL of 50% (w/v) PEG/PBS solution (PEG molecular weight of 1,450 g/mole, Sigma) at 37° C. The fusion was stopped by slowly adding 10.5 mL of RPMI media (no additives) (JRH) (37° C.) over 1 minute. The fused cells were centrifuged for 5 minutes at 750 rpm. The cells were then resuspended in HAT medium (RPMI/HEPES medium containing 10% Fetal Bovine Serum (JRH), 1 mM sodium pyruvate, 2 mM L-glutamine, 10 µg/mL gentamicin, 2.5% Origen culturing supplement (Fisher), 50 µM 2-mercaptoethanol, 1% 653-conditioned RPMI media, 100 µM hypoxanthine, 0.4 µM aminopterin, and 16 µM thymidine) and then plated at 200 µL/well in five 96-well flat bottom tissue culture plates. The plates were then placed in a humidified 37° C. incubator containing 5% $CO_2$ and 95% air for 7-10 days.

Detection of Human IgG Anti-TNFα Antibodies in Mouse Serum. Solid phase EIAs were used to screen mouse sera for human IgG antibodies specific for human TNFα. Briefly, plates were coated with TNFα at 1 µg/mL in PBS overnight. After washing in 0.15 M saline containing 0.02% (v/v) Tween 20, the wells were blocked with 1% (w/v) BSA in PBS, 200 µL/well for 1 hour at RT. Plates were either used immediately or frozen at −20° C. for future use. Mouse sera were incubated in two-fold serial dilutions on the human TNFα-coated plates at 50 µL/well at RT for 1 hour. The plates were washed and then probed with 50 µL/well HRP-labeled goat anti-human IgG, Fc specific (Accurate) diluted 1:30,000 in 1% BSA-PBS for 1 hour at RT. The plates were again washed and 100 µL/well of the citrate-phosphate substrate solution (0.1 M citric acid and 0.2 M sodium phosphate, 0.01% $H_2O_2$ and 1 mg/mL OPD) was added for 15 minutes at RT. Stop solution (4N sulfuric acid) was then added at 25 µL/well and the OD's were read at 490 nm using an automated plate spectrophotometer.

Detection of Totally Human Immunoglobulins in Hybridoma Supernatants. Because the GenPharm mouse is capable of generating both mouse and human immunoglobulin chains, two separate EIA assays were used to test growth-positive hybridoma clones for the presence of both human light chains and human heavy chains. Plates were coated as described above and undiluted hybridoma supernatants were incubated on the plates for one hour at 37° C. The plates were washed and probed with either HRP-conjugated goat anti-human kappa (Southern Biotech) antibody diluted 1:10,000 in 1% BSA-HBSS or HRP-conjugated goat anti-human IgG Fc specific antibody diluted to 1:30,000 in 1% BSA-HBSS for one hour at 37° C. The plates were then incubated with substrate solution as described above. Hybridoma clones that did not give a positive signal in both the anti-human kappa and anti-human IgG Fc EIA formats were discarded.

Isotyping. Isotype determination of the antibodies was accomplished using an EIA in a format similar to that used to screen the mouse immune sera for specific titers. EIA plates were coated with goat anti-human IgG (H+L) at 10 :g/mL in sodium carbonate buffer overnight at 4EC and blocked as described above. Neat supernatants from 24 well cultures were incubated on the plate for one hour at RT. The plate was washed and probed with HRP-labeled goat anti-human IgG1, IgG2, $IgG_3$ or $IgG_4$ (Binding Site) diluted at 1:4000 in 1% BSA-PBS for one hour at RT. The plate was again washed and incubated with substrate solution as described above.

Results and Discussion. Generation of Totally Human Anti-Human TNFα Monoclonal Antibodies. One fusion, named GenTNV, was performed from a GenPharm mouse immunized with recombinant human TNFα protein. From this fusion, 196 growth-positive hybrids were screened. Eight hybridoma cell lines were identified that secreted totally human IgG antibodies reactive with human TNFα. These eight cell lines each secreted immunoglobulins of the human IgG1κ isotype and all were subcloned twice by limiting dilution to obtain stable cell lines (>90% homogeneous). Cell line names and respective C code designations are listed in Table 1. Each of the cell lines was frozen in 12-vial research cell banks stored in liquid nitrogen.

Parental cells collected from wells of a 24-well culture dish for each of the eight cell lines were handed over to Molecular Biology group on 2-18-99 for transfection and further characterization.

TABLE 1

GenTNV Cell Line Designations

| Name | C Code Designation |
|---|---|
| GenTNV14.17.12 | C414A |
| GenTNV15.28.11 | C415A |
| GenTNV32.2.16 | C416A |
| GenTNV86.14.34 | C417A |
| GenTNV118.3.36 | C418A |
| GenTNV122.23.2 | C419A |
| GenTNV148.26.12 | C420A |
| GenTNV196.9.1 | C421A |

Conclusion.

The GenTNV fusion was performed utilizing splenocytes from a hybrid mouse containing human variable and constant region antibody transgenes that was immunized with recombinant human TNFα prepared at Centocor. Eight totally human, TNFα-reactive IgG monoclonal antibodies of the IgG1κ isotype were generated. Parental cell lines were transferred to Molecular Biology group for further characterization and development. One of these new human antibodies may prove useful in anti-inflammatory with the potential benefit of decreased immunogenicity and allergic-type complications as compared with Remicade.

REFERENCES

Taylor, et al., International Immunology 6:579-591 (1993).
Lonberg, et al., Nature 368:856-859 (1994).
Neuberger, M. Nature Biotechnology 14:826 (1996).
Fishwild, et al., Nature Biotechnology 14:845-851 (1996).
Scallon, et al., Cytokine 7:759-770 (1995).

Example 4: Cloning and Preparation of Cell Lines Expressing Human Anti-TNFα Antibody Summary A panel of eight human monoclonal antibodies (mAbs) with a TNV designation were found to bind immobilized human TNFα with apparently high avidity. Seven of the eight mAbs were shown to efficiently block huTNFα binding to a recombinant TNF receptor. Sequence analysis of the DNA encoding the seven mAbs confirmed that all the mAbs had human V regions. The DNA sequences also revealed that three pairs of the mAbs were identical to each other, such that the original panel of eight mAbs contained only four distinct mAbs, represented by TNV14, TNV15, TNV148, and TNV196. Based on analyses of the deduced amino acid sequences of the mAbs and results of in vitro TNFα neutralization data, mAb TNV148 and TNV14 were selected for further study.

Because the proline residue at position 75 (framework 3) in the TNV148 heavy chain was not found at that position in other human antibodies of the same subgroup during a database search, site-directed DNA mutagenesis was performed to encode a serine residue at that position in order to have it conform to known germline framework e sequences. The serine modified mAb was designated TNV148B. PCR-amplified DNA encoding the heavy and light chain variable regions of TNV 148B and TNV14 was cloned into newly prepared expression vectors that were based on the recently cloned heavy and light chain genes of another human mAb (12B75), disclosed in U.S. patent application No. 60/236,827, filed Oct. 7, 2000, entitled IL-12 Antibodies, Compositions, Methods and Uses, published as WO 02/12500 which is entirely incorporated herein by reference.

P3X63Ag8.653 (653) cells or Sp2/0-Ag14 (Sp2/0) mouse myeloma cells were transfected with the respective heavy and light chain expression plasmids and screened through two rounds of subcloning for cell lines producing high levels of recombinant TNV148B and TNV14 (rTNV148B and rTNV14) mAbs. Evaluations of growth curves and stability of mAb production over time indicated that 653-transfectant clones C466D and C466C stably produced approximately 125 :g/ml of rTNV148B mAb in spent cultures whereas Sp2/0 transfectant 1.73-12-122 (C467A) stably produced approximately 25 :g/ml of rTNV148B mAb in spent cultures. Similar analyses indicated that Sp2/0-transfectant clone C476A produced 18 :g/ml of rTNV14 in spent cultures.

Introduction. A panel of eight mAbs derived from human TNFα-immunized GenPharm/Medarex mice (HCo12/KCo5 genotype) were previously shown to bind human TNFα and to have a totally human IgG1, kappa isotype. A simple binding assay was used to determine whether the exemplary mAbs of the invention were likely to have TNFα-neutralizing activity by evaluating their ability to block TNFα from binding to recombinant TNF receptor. Based on those results, DNA sequence results, and in vitro characterizations of several of the mAbs, TNV148 was selected as the mAb to be further characterized.

DNA sequences encoding the TNV148 mAb were cloned, modified to fit into gene expression vectors that encode suitable constant regions, introduced into the well-characterized 653 and Sp2/0 mouse myeloma cells, and resulting transfected cell lines screened until subclones were identified that produced 40-fold more mAb than the original hybridoma cell line.

Materials and Methods.

Reagents and Cells. TRIZOL reagent was purchased from Gibco BRL. Proteinase K was obtained from Sigma Chemical Company. Reverse Transcriptase was obtained from Life Sciences, Inc. Taq DNA Polymerase was obtained from either Perkin Elmer Cetus or Gibco BRL. Restriction enzymes were purchased from New England Biolabs. QIAquick PCR Purification Kit was from Qiagen. A QuikChange Site-Directed Mutagenesis Kit was purchased from Stratagene. Wizard plasmid miniprep kits and RNasin were from Promega. Optiplates were obtained from Packard. $^{125}$Iodine was purchased from Amersham. Custom oligonucleotides were purchased from Keystone/Biosource International. The names, identification numbers, and sequences of the oligonucleotides used in this work are shown in Table 2.

Table 2. Oligonucleotides Used to Clone, Engineer, or Sequence the TNV mAb Genes.

The amino acids encoded by oligonucleotide 5'14s and HuH-J6 are shown above the sequence. The 'M' amino acid residue represents the translation start codon. The underlined sequences in oligonucleotides 5'14s and HuH-J6 mark the BsiWI and BstBI restriction sites, respectively. The slash in HuH-J6 corresponds to the exon/intron boundary. Note that oligonucleotides whose sequence corresponds to the minus strand are written in a 3'-5' orientation.

| Name | I.D. | Sequence |
|---|---|---|
| HG1-4b | 119 | 3'-TTGGTCCAGTCGGACTGG-5' (SEQ ID NO: 10) |
| HG1-5b | 354 | 3'-CACCTGCACTCGGTGCTT-5' (SEQ ID NO: 11) |
| HG1hg | 360 | 3'-CACTGTTTTGAGTGTGTACGGGCTTAAGTT-5' (SEQ ID NO: 12) |
| HG1-6 | 35 | 3'-GCCGCACGTGTGGAAGGG-5' (SEQ ID NO: 13) |
| HCK1-3E | 117 | 3'-AGTCAAGGTCGGACTGGCTTAAGTT-5' (SEQ ID NO: 14) |
| HuK-3'Hd | 208 | 3'-GTTGTCCCCTCTCACAATCTTCGAATTT-5' (SEQ ID NO: 15) |
| HVKRNAseq | 34 | 3'-GGCGGTAGACTACTCGTC-5' (SEQ ID NO: 16) |
| BsiWI | | M D W T W S I (SEQ ID NO: 17) |
| 5'14s | 366 | 5-TTTCGTACGCCACCATGGACTGGACCTGGAGCATC-3' (SEQ ID NO: 18) |
| 5'46s | 367 | 5'-TTTCGTACGCCACCATGGGGTTTGGGCTGAGCTG-3' (SEQ ID NO: 19) |

-continued

| Name | I.D. | Sequence |
|---|---|---|
| 5'47s | 368 | 5'-TTTCGTACGCCACCATGGAGTTTGGGCTGAGC ATG-3' (SEQ ID NO: 20) |
| 5'63s | 369 | 5'-TTTCGTACGCCACCATGAAACACCTGTGGTTC TTC-3' (SEQ ID NO: 21) |
| 5'73s | 370 | 5'-TTTCGTACGCCACCATGGGGTCAACCGCCATC CTC-3' (SEQ ID NO: 22) |
| T V T V S S | | BstBI (SEQ ID NO: 23) |
| HuH-J6 | 388 | 3'GTGCCAGTGGCAGAGGAGTCCATTCAAGCTTAA GTT-5' (SEQ ID NO: 24) |
| SalI | | M D M R V (SEQ ID NO: 25) |
| LK7s | 362 | 5'-TTTGTCGACACCATGGACATGAGGGTCC(TC) C-3' (SEQ ID NO: 26) |
| LVgs | 363 | 5'-TTTGTCGACACCATGGAAGCCCCAGCTC-3' (SEQ ID NO: 27) |
| T K V D I K | | AflII (SEQ ID NO: 28) |
| HuL-J3 | 380 | 3'CTGGTTTCACCTATAGTTTG/CATTCAGAATTC GGCGCCTTT (SEQ ID NO: 29) |
| V148-QC1 | 399 | 5'-CATCTCCAGAGACAATtCCAAGAACACGCTGT ATC-3' (SEQ ID NO: 30) |
| V148-QC2 | 400 | 3'-GTAGAGGTCTCTGTTAaGGTTCTTGTGCGACA TAG-5' (SEQ ID NO: 31) |

A single frozen vial of 653 mouse myeloma cells was obtained. The vial was thawed that day and expanded in T flasks in IMDM, 5% FBS, 2 mM glutamine (media). These cells were maintained in continuous culture until they were transfected 2 to 3 weeks later with the anti-TNF DNA described here. Some of the cultures were harvested 5 days after the thaw date, pelleted by centrifugation, and resuspended in 95% FBS, 5% DMSO, aliquoted into 30 vials, frozen, and stored for future use. Similarly, a single frozen vial of Sp2/0 mouse myeloma cells was obtained. The vial was thawed, a new freeze-down prepared as described above, and the frozen vials stored in CBC freezer boxes AA and AB. These cells were thawed and used for all Sp2/0 transfections described here.

Assay for Inhibition of TNF Binding to Receptor. Hybridoma cell supernatants containing the TNV mAbs were used to assay for the ability of the mAbs to block binding of $^{125}$I-labeled TNFα to the recombinant TNF receptor fusion protein, p55-sf2 (Scallon et al. (1995) *Cytokine* 7:759-770). 50 :l of p55-sf2 at 0.5 :g/ml in PBS was added to Optiplates to coat the wells during a one-hour incubation at 37° C. Serial dilutions of the eight TNV cell supernatants were prepared in 96-well round-bottom plates using PBS/0.1% BSA as diluent. Cell supernatant containing anti-IL-18 mAb was included as a negative control and the same anti-IL-18 supernatant spiked with cA2 (anti-TNF chimeric antibody, Remicade, U.S. Pat. No. 5,770,198, entirely incorporated herein by reference) was included as a positive control. $^{125}$I-labeled TNFα (58 :Ci/:g, D. Shealy) was added to 100 :l of cell supernatants to have a final TNFα concentration of 5 ng/ml. The mixture was preincubated for one hour at RT. The coated Optiplates were washed to remove unbound p55-sf2 and 50 :l of the $^{125}$I-TNFα/cell supernatant mixture was transferred to the Optiplates. After 2 hrs at RT, Optiplates were washed three times with PBS-Tween. 100 :l of Microscint-20 was added and the cpm bound determined using the TopCount gamma counter.

Amplification of V Genes and DNA Sequence Analysis. Hybridoma cells were washed once in PBS before addition of TRIZOL reagent for RNA preparation. Between 7×10$^6$ and 1.7×10$^7$ cells were resuspended in 1 ml TRIZOL. Tubes were shaken vigorously after addition of 200 µl of chloroform. Samples were centrifuged at 4° C. for 10 minutes. The aqueous phase was transferred to a fresh microfuge tube and an equal volume of isopropanol was added. Tubes were shaken vigorously and allowed to incubate at room temperature for 10 minutes. Samples were then centrifuged at 4° C. for 10 minutes. The pellets were washed once with 1 ml of 70% ethanol and dried briefly in a vacuum dryer. The RNA pellets were resuspended with 40 µl of DEPC-treated water. The quality of the RNA preparations was determined by fractionating 0.5 µl in a 1% agarose gel. The RNA was stored in a −80° C. freezer until used.

To prepare heavy and light chain cDNAs, mixtures were prepared that included 3 µl of RNA and 1 µg of either oligonucleotide 119 (heavy chain) or oligonucleotide 117 (light chain) (see Table 1) in a volume of 11.5 µl. The mixture was incubated at 70° C. for 10 minutes in a water bath and then chilled on ice for 10 minutes. A separate mixture was prepared that was made up of 2.5 µl of 10× reverse transcriptase buffer, 10 µl of 2.5 mM dNTPs, 1 µl of reverse transcriptase (20 units), and 0.4 µl of ribonuclease inhibitor RNasin (1 unit). 13.5 µl of this mixture was added to the 11.5 µl of the chilled RNA/oligonucleotide mixture and the reaction incubated for 40 minutes at 42° C. The cDNA synthesis reaction was then stored in a −20° C. freezer until used.

The unpurified heavy and light chain cDNAs were used as templates to PCR-amplify the variable region coding sequences. Five oligonucleotide pairs (366/354, 367/354, 368/354, 369/354, and 370/354, Table 1) were simultaneously tested for their ability to prime amplification of the heavy chain DNA. Two oligonucleotide pairs (362/208 and 363/208) were simultaneously tested for their ability to prime amplification of the light chain DNA. PCR reactions were carried out using 2 units of PLATINUM™ high fidelity (HIFI) Taq DNA polymerase in a total volume of 50 µl. Each reaction included 2 µl of a cDNA reaction, 10 pmoles of each oligonucleotide, 0.2 mM dNTPs, 5 µl of 10×HIFI Buffer, and 2 mM magnesium sulfate. The thermal cycler program was 95° C. for 5 minutes followed by 30 cycles of (94° C. for 30 seconds, 62° C. for 30 seconds, 68° C. for 1.5 minutes). There was then a final incubation at 68° C. for 10 minutes.

To prepare the PCR products for direct DNA sequencing, they were purified using the QIAquick™ PCR Purification Kit according to the manufacturer's protocol. The DNA was eluted from the spin column using 50 µl of sterile water and then dried down to a volume of 10 µl using a vacuum dryer. DNA sequencing reactions were then set up with 1 µl of purified PCR product, 10 µM oligonucleotide primer, 4 µl BigDye Terminator™ ready reaction mix, and 14 µl sterile water for a total volume of 20 µl. Heavy chain PCR products made with oligonucleotide pair 367/354 were sequenced with oligonucleotide primers 159 and 360. Light chain PCR products made with oligonucleotide pair 363/208 were sequenced with oligonucleotides 34 and 163. The thermal cycler program for sequencing was 25 cycles of (96° C. for 30 seconds, 50° C. for 15 seconds, 60°C for 4 minutes) followed by overnight at 4° C. The reaction products were fractionated through a polyacrylamide gel and detected using an ABI 377 DNA Sequencer.

Site-directed Mutagenesis to Change an Amino Acid. A single nucleotide in the TNV148 heavy chain variable region DNA sequence was changed in order to replace Pro$^{75}$ with a Serine residue in the TNV148 mAb. Complimentary oligonucleotides, 399 and 400 (Table 1), were designed and ordered to make this change using the QuikChange™ site-directed mutagenesis method as described by the manufacturer. The two oligonucleotides were first fractionated through a 15% polyacrylamide gel and the major bands purified. Mutagenesis reactions were prepared using either 10 ng or 50 ng of TNV 148 heavy chain plasmid template (p1753), 5 µl of 10× reaction buffer, 1 µl of dNTP mix, 125 ng of primer 399, 125 ng of primer 400, and 1 µl of Pfu DNA Polymerase. Sterile water was added to bring the total volume to 50 µl. The reaction mix was then incubated in a thermal cycler programmed to incubate at 95° C. for 30 seconds, and then cycle 14 times with sequential incubations of 95° C. for 30 seconds, 55° C. for 1 minute, 64° C. for 1 minute, and 68° C. for 7 minutes, followed by 30° C. for 2 minutes (1 cycle). These reactions were designed to incorporate the mutagenic oligonucleotides into otherwise identical, newly synthesized plasmids. To rid of the original TNV148 plasmids, samples were incubated at 37°C for 1 hour after addition of 1 µl of DpnI endonuclease, which cleaves only the original methylated plasmid. One µl of the reaction was then used to transform Epicurian Coli XL1-Blue supercompetent E. coli by standard heat-shock methods and transformed bacteria identified after plating on LB-ampicillin agar plates. Plasmid minipreps were prepared using the Wizard™ kits as described by the manufacturer. After elution of sample from the Wizard™ column, plasmid DNA was precipitated with ethanol to further purify the plasmid DNA and then resuspended in 20 µl of sterile water. DNA sequence analysis was then performed to identify plasmid clones that had the desired base change and to confirm that no other base changes were inadvertently introduced into the TNV 148 coding sequence. One µl of plasmid was subjected to a cycle sequencing reaction prepared with 3 µl of BigDye mix, 1 µl of pUC19 Forward primer, and 10 µl of sterile water using the same parameters described in Section 4.3.

Construction of Expression Vectors from 12B75 Genes. Several recombinant DNA steps were performed to prepare a new human IgG1 expression vector and a new human kappa expression vector from the previously-cloned genomic copies of the 12B75-encoding heavy and light chain genes, respectively, disclosed in U.S. patent application No. 60/236,827, filed Oct. 7, 2000, entitled IL-12 Antibodies, Compositions, Methods and Uses, published as WO 02/12500, which is entirely incorporated herein by reference. The final vectors were designed to permit simple, one-step replacement of the existing variable region sequences with any appropriately-designed, PCR-amplified, variable region.

To modify the 12B75 heavy chain gene in plasmid p1560, a 6.85 kb BamHI/HindIII fragment containing the promoter and variable region was transferred from p1560 to pUC19 to make p1743. The smaller size of this plasmid compared to p1560 enabled use of QuikChange™ mutagenesis (using oligonucleotides BsiWI-1 and BsiWI-2) to introduce a unique BsiWI cloning site just upstream of the translation initiation site, following the manufacturer's protocol. The resulting plasmid was termed p1747. To introduce a BstBI site at the 3' end of the variable region, a 5' oligonucleotide primer was designed with SalI and BstBI sites. This primer was used with the pUC reverse primer to amplify a 2.75 kb fragment from p1747. This fragment was then cloned back into the naturally-occurring SalI site in the 12B75 variable region and a HindIII site, thereby introducing the unique BstBI site. The resulting intermediate vector, designated p1750, could accept variable region fragments with BsiWI and BstBI ends. To prepare a version of heavy chain vector in which the constant region also derived from the 12B75 gene, the BamHI-HindIII insert in p1750 was transferred to pBR322 in order to have an EcoRI site downstream of the HindIII site. The resulting plasmid, p1768, was then digested with HindIII and EcoRI and ligated to a 5.7 kb HindIII-EcoRI fragment from p1744, a subclone derived by cloning the large BamHI-BamHI fragment from p1560 into pBC. The resulting plasmid, p1784, was then used as vector for the TNV Ab cDNA fragments with BsiWI and BstBI ends. Additional work was done to prepare expression vectors, p1788 and p1798, which include the IgG1 constant region from the 12B75 gene and differ from each other by how much of the 12B75 heavy chain J-C intron they contain.

To modify the 12B75 light chain gene in plasmid p1558, a 5.7 kb SalI/AflII fragment containing the 12B75 promoter and variable region was transferred from p1558 into the XhoI/AflII sites of plasmid L28. This new plasmid, p1745, provided a smaller template for the mutagenesis step. Oligonucleotides (C340salI and C340sal2) were used to introduce a unique SalI restriction site at the 5' end of the variable region by QuikChange™ mutagenesis. The resulting intermediate vector, p1746, had unique SalI and AflII restriction sites into which variable region fragments could be cloned. Any variable region fragment cloned into p1746 would preferably be joined with the 3' half of the light chain gene. To prepare a restriction fragment from the 3' half of the 12B75 light chain gene that could be used for this purpose, oligonucleotides BAHN-1 and BAHN-2 were annealed to each other to form a double-stranded linker containing the restriction sites BsiW1, AflII, HindII, and NotI and which contained ends that could be ligated into KpnI and SacI sites. This linker was cloned between the KpnI and SacI sites of pBC to give plasmid p1757. A 7.1 kb fragment containing the 12B75 light chain constant region, generated by digesting p1558 with AflII, then partially digesting with HindIII, was cloned between the AflII and HindII sites of p1757 to yield p1762. This new plasmid contained unique sites for BsiWI and AflII into which the BsiWI/AflII fragment containing the promoter and variable regions could be transferred uniting the two halves of the gene.

cDNA Cloning and Assembly of Expression Plasmids. All RT-PCR reactions (see above) were treated with Klenow enzyme to further fill in the DNA ends. Heavy chain PCR fragments were digested with restriction enzymes BsiWI and BstBI and then cloned between the BsiWI and BstBI sites of plasmid L28 (L28 used because the 12B75-based intermediate vector p1750 had not been prepared yet). DNA sequence analysis of the cloned inserts showed that the resulting constructs were correct and that there were no errors introduced during PCR amplifications. The assigned identification numbers for these L28 plasmid constructs (for TNV14, TNV15, TNV148, TNV148B, and TNV196) are shown in Table 3.

The BsiWI/BstBI inserts for TNV14, TNV148, and TNV148B heavy chains were transferred from the L28 vector to the newly prepared intermediate vector, p1750. The assigned identification numbers for these intermediate plasmids are shown in Table 2. This cloning step and subsequent steps were not done for TNV15 and TNV196. The variable regions were then transferred into two different human IgG1 expression vectors. Restriction enzymes EcoRI and HindIII were used to transfer the variable regions into Centocor's previously-used IgG1 vector, p104. The resulting expression plasmids, which encode an IgG1 of the Gm(f+) allotype, were designated p1781 (TNV14), p1782 (TNV148), and p1783 (TNV148B) (see Table 2). The variable regions were also cloned upstream of the IgG1 constant region derived from the 12B75 (GenPharm) gene. Those expression plasmids, which encode an IgG1 of the G1m(z) allotype, are also listed in Table 3.

Table 3. Plasmid Identification Numbers for Various Heavy and Light Chain Plasmids.

The L28 vector or pBC vector represents the initial Ab cDNA clone. The inserts in those plasmids were transferred to an incomplete 12B75-based vector to make the intermediate plasmids. One additional transfer step resulted in the final expression plasmids that were either introduced into cells after being linearized or used to purify the mAb gene inserts prior to cell transfection. (ND)=not done.

| Mab | Gm(f+) 128 vector Plasmid ID | Intermediate Plasmid ID | G1m(z) Expression Plasmid ID | Expression Plasmid ID |
|---|---|---|---|---|
| Heavy Chains | | | | |
| TNV14 | p1751 | p1777 | p1781 | p1786 |
| TNV15 | p1752 | (ND) | (ND) | (ND) |
| TNV148 p1753 | p1778 | p1782 | p1787 | |
| TNV148B p1760 | p1779 | p1783 | p1788 | |
| TNV196 p1754 | (ND) | (ND) | (ND) | |
| Light Chains | pBC vector Plasmid ID | Intermediate Plasmid | Expression ID Plasmid ID | |
| TNV14 | p1748 | p1755 | p1775 | |
| TNV15 | p1748 | p1755 | p1775 | |
| TNV148 | p1749 | p1756 | p1776 | |
| TNV196 | p1749 | p1756 | p1776 | |

Light chain PCR products were digested with restriction enzymes SalI and SacII and then cloned between the SalI and SacII sites of plasmid pBC. The two different light chain versions, which differed by one amino acid, were designated p1748 and p1749 (Table 2). DNA sequence analysis confirmed that these constructs had the correct sequences. The SalI/AflII fragments in p1748 and p1749 were then cloned between the SalI and AflII sites of intermediate vector p1746 to make p1755 and p1756, respectively. These 5' halves of the light chain genes were then joined to the 3' halves of the gene by transferring the BsiWI/AflII fragments from p1755 and p1756 to the newly prepared construct p1762 to make the final expression plasmids p1775 and p1776, respectively (Table 2).

Cell Transfections, Screening, and Subcloning. A total of 15 transfections of mouse myeloma cells were performed with the various TNV expression plasmids (see Table 3 in the Results and Discussion section). These transfections were distinguished by whether (1) the host cells were Sp2/0 or 653; (2) the heavy chain constant region was encoded by Centocor's previous IgG1 vector or the 12B75 heavy chain constant region; (3) the mAb was TNV148B, TNV148, TNV14, or a new HC/LC combination; (4) whether the DNA was linearized plasmid or purified Ab gene insert; and (5) the presence or absence of the complete J-C intron sequence in the heavy chain gene. In addition, several of the transfections were repeated to increase the likelihood that a large number of clones could be screened.

Sp2/0 cells and 653 cells were each transfected with a mixture of heavy and light chain DNA (8-12 :g each) by electroporation under standard conditions as previously described (Knight D M et al. (1993) *Molecular Immunology* 30:1443-1453). For transfection numbers 1, 2, 3, and 16, the appropriate expression plasmids were linearized by digestion with a restriction enzyme prior to transfection. For example, SalI and NotI restriction enzymes were used to linearize TNV 148B heavy chain plasmid p1783 and light chain plasmid p1776, respectively. For the remaining transfections, DNA inserts that contained only the mAb gene were separated from the plasmid vector by digesting heavy chain plasmids with BamHI and light chain plasmids with BsiWI and NotI. The mAb gene inserts were then purified by agarose gel electrophoresis and Qiex purification resins. Cells transfected with purified gene inserts were simultaneously transfected with 3-5 :g of PstI-linearized pSV2gpt plasmid (p13) as a source of selectable marker. Following electroporation, cells were seeded in 96-well tissue culture dishes in IMDM, 15% FBS, 2 mM glutamine and incubated at 37° C. in a 5% $CO_2$ incubator. Two days later, an equal volume of IMDM, 5% FBS, 2 mM glutamine, 2×MHX selection (1×MHX=0.5 :g/ml mycophenolic acid, 2.5 :g/ml hypoxanthine, 50 :g/ml xanthine) was added and the plates incubated for an additional 2 to 3 weeks while colonies formed.

Cell supernatants collected from wells with colonies were assayed for human IgG by ELISA as described. In brief, varying dilutions of the cell supernatants were incubated in 96-well EIA plates coated with polyclonal goat anti-human IgG Fc fragment and then bound human IgG was detected using Alkaline Phosphatase-conjugated goat anti-human IgG(H+L) and the appropriate color substrates. Standard curves, which used as standard the same purified mAb that was being measured in the cell supernatants, were included on each EIA plate to enable quantitation of the human IgG in the supernatants. Cells in those colonies that appeared to be producing the most human IgG were passaged into 24-well plates for additional production determinations in spent cultures and the highest-producing parental clones were subsequently identified.

The highest-producing parental clones were subcloned to identify higher-producing subclones and to prepare a more homogenous cell line. 96-well tissue culture plates were seeded with one cell per well or four cells per well in of IMDM, 5% FBS, 2 mM glutamine, 1×MHX and incubated at 37° C. in a 5% $CO_2$ incubator for 12 to 20 days until colonies were apparent. Cell supernatants were collected from wells that contained one colony per well and analyzed by ELISA as described above. Selected colonies were passaged to 24-well plates and the cultures allowed to go spent before identifying the highest-producing subclones by quantitating the human IgG levels in their supernatants. This process was repeated when selected first-round subclones were subjected to a second round of subcloning. The best second-round subclones were selected as the cell lines for development.

Characterization of Cell Subclones. The best second-round subclones were chosen and growth curves performed to evaluate mAb production levels and cell growth characteristics. T75 flasks were seeded with $1\times10^5$ cells/ml in 30 ml IMDM, 5% FBS, 2 mM glutamine, and 1×MHX (or serum-free media). Aliquots of 300 μl were taken at 24 hr intervals and live cell density determined. The analyses continued until the number of live cells was less than $1\times10^5$ cells/ml. The collected aliquots of cell supernatants were assayed for the concentration of antibody present. ELISA assays were performed using as standard rTNV148B or rTNV14 JG92399. Samples were incubated for 1 hour on ELISA plates coated with polyclonal goat anti-human IgG Fc and bound mAb detected with Alkaline Phosphatase-conjugated goat anti-human IgG(H+L) at a 1:1000 dilution.

A different growth curve analysis was also done for two cell lines for the purpose of comparing growth rates in the presence of varying amounts of MHX selection. Cell lines C466A and C466B were thawed into MHX-free media (IMDM, 5% FBS, 2 mM glutamine) and cultured for two additional days. Both cell cultures were then divided into three cultures that contained either no MHX, 0.2×MHX, or 1×MHX (1×MHX=0.5 :g/ml mycophenolic acid, 2.5 :g/ml hypoxanthine, 50 :g/ml xanthine). One day later, fresh T75 flasks were seeded with the cultures at a starting density of $1\times10^5$ cells/ml and cells counted at 24 hour intervals for one week. Aliquots for mAb production were not collected. Doubling times were calculated for these samples using the formula provided in SOP PD32.025.

Additional studies were performed to evaluate stability of mAb production over time. Cultures were grown in 24-well plates in IMDM, 5% FBS, 2 mM glutamine, either with or without MHX selection. Cultures were split into fresh cultures whenever they became confluent and the older culture was then allowed to go spent. At this time, an aliquot of supernatant was taken and stored at 4° C. Aliquots were taken over a 55-78 day period. At the end of this period, supernatants were tested for amount of antibody present by the anti-human IgG Fc ELISA as outlined above.

Results and Discussion.
Inhibition of TNF Binding to Recombinant Receptor.

A simple binding assay was done to determine whether the eight TNV mAbs contained in hybridoma cell supernatant were capable of blocking TNFα binding to receptor. The concentrations of the TNV mAbs in their respective cell supernatants were first determined by standard ELISA analysis for human IgG. A recombinant p55 TNF receptor/IgG fusion protein, p55-sf2, was then coated on EIA plates and $^{125}$I-labeled TNFα allowed to bind to the p55 receptor in the presence of varying amounts of TNV mAbs. As shown in FIG. 1, all but one (TNV122) of the eight TNV mAbs efficiently blocked TNFα binding to p55 receptor. In fact, the TNV mAbs appeared to be more effective at inhibiting TNFα binding than cA2 positive control mAb that had been spiked into negative control hybridoma supernatant. These results were interpreted as indicating that it was highly likely that the TNV mAbs would block TNFα bioactivity in cell-based assays and in vivo and therefore additional analyses were warranted.

DNA Sequence Analysis.
Confirmation that the RNAs Encode Human mAbs.

As a first step in characterizing the seven TNV mAbs (TNV14, TNV15, TNV32, TNV86, TNV118, TNV148, and TNV196) that showed TNFα-blocking activity in the receptor binding assay, total RNA was isolated from the seven hybridoma cell lines that produce these mAbs. Each RNA sample was then used to prepare human antibody heavy or light chain cDNA that included the complete signal sequence, the complete variable region sequence, and part of the constant region sequence for each mAb. These cDNA products were then amplified in PCR reactions and the PCR-amplified DNA was directly sequenced without first cloning the fragments. The heavy chain cDNAs sequenced were >90% identical to one of the five human germline genes present in the mice, DP-46 (FIG. 2). Similarly, the light chain cDNAs sequenced were either 100% or 98% identical to one of the human germline genes present in the mice (FIG. 3). These sequence results confirmed that the RNA molecules that were transcribed into cDNA and sequenced encoded human antibody heavy chains and human antibody light chains. It should be noted that, because the variable regions were PCR-amplified using oligonucleotides that map to the 5' end of the signal sequence coding sequence, the first few amino acids of the signal sequence may not be the actual sequence of the original TNV translation products but they do represent the actual sequences of the recombinant TNV mAbs.

Unique Neutralizing mAbs.

Analyses of the cDNA sequences for the entire variable regions of both heavy and light chains for each mAb revealed that TNV32 is identical to TNV15, TNV118 is identical to TNV14, and TNV86 is identical to TNV148. The results of the receptor binding assay were consistent with the DNA sequence analyses, i.e. both TNV86 and TNV148 were approximately 4-fold better than both TNV118 and TNV 14 at blocking TNF binding. Subsequent work was therefore focused on only the four unique TNV mAbs, TNV14, TNV15, TNV148, and TNV 196.

Relatedness of the Four mAbs

The DNA sequence results revealed that the genes encoding the heavy chains of the four TNV mAbs were all highly homologous to each other and appear to have all derived from the same germline gene, DP-46 (FIG. 2). In addition, because each of the heavy chain CDR3 sequences are so similar and of the same length, and because they all use the J6 exon, they apparently arose from a single VDJ gene rearrangement event that was then followed by somatic changes that made each mAb unique. DNA sequence analyses revealed that there were only two distinct light chain genes among the four mAbs (FIG. 3). The light chain variable region coding sequences in TNV14 and TNV15 are identical to each other and to a representative germline sequence of the Vg/38K family of human kappa chains. The TNV148 and TNV 196 light chain coding sequences are identical to each other but differ from the germline sequence at two nucleotide positions (FIG. 3).

The deduced amino acid sequences of the four mAbs revealed the relatedness of the actual mAbs. The four mAbs contain four distinct heavy chains (FIG. 4) but only two distinct light chains (FIG. 5). Differences between the TNV mAb sequences and the germline sequences were mostly confined to CDR domains but three of the mAb heavy chains also differed from the germline sequence in the framework regions (FIG. 4). Compared to the DP-46 germline-encoded Ab framework regions, TNV14 was identical, TNV15 differed by one amino acid, TNV148 differed by two amino acids, and TNV 196 differed by three amino acids.

Cloning of cDNAs, Site-specific Mutagenesis, and Assembly of Final Expression Plasmids. Cloning of cDNAs. Based on the DNA sequence of the PCR-amplified variable regions, new oligonucleotides were ordered to perform another round of PCR amplification for the purpose of adapting the coding sequence to be cloned into expression vectors. In the case of the heavy chains, the products of this second round of PCR were digested with restriction enzymes BsiWI and BstBI and cloned into plasmid vector L28 (plasmid identification numbers shown in Table 2). In the case of the light chains, the second-round PCR products were digested with SalI and AflII and cloned into plasmid vector pBC. Individual clones were then sequenced to confirm that their sequences were identical to the previous sequence obtained from direct sequencing of PCR products, which reveals the most abundant nucleotide at each position in a potentially heterogeneous population of molecules.

Site-specific Mutagenesis to Change TNV148. mAbs TNV 148 and TNV 196 were being consistently observed to be four-fold more potent than the next best mAb (TNV14) at neutralizing TNFα bioactivity. However, as described above, the TNV148 and TNV196 heavy chain framework sequences differed from the germline framework sequences. A comparison of the TNV148 heavy chain sequence to other human antibodies indicated that numerous other human mAbs contained an Ile residue at position 28 in framework 1 (counting mature sequence only) whereas the Pro residue at position 75 in framework 3 was an unusual amino acid at that position.

A similar comparison of the TNV 196 heavy chain suggested that the three amino acids by which it differs from the germline sequence in framework 3 may be rare in human mAbs. There was a possibility that these differences may render TNV148 and TNV196 immunogenic if administered to humans. Because TNV148 had only one amino acid residue of concern and this residue was believed to be unimportant for TNFα binding, a site-specific mutagenesis technique was used to change a single nucleotide in the TNV148 heavy chain coding sequence (in plasmid p1753) so that a germline Ser residue would be encoded in place of the Pro residue at position 75. The resulting plasmid was termed p1760 (see Table 2). The resulting gene and mAb were termed TNV148B to distinguish it from the original TNV148 gene and mAb (see FIG. 5).

Assembly of Final Expression Plasmids. New antibody expression vectors were prepared that were based on the 12B75 heavy chain and light chain genes previously cloned as genomic fragments. Although different TNV expression plasmids were prepared (see Table 2), in each case the 5' flanking sequences, promoter, and intron enhancer derived from the respective 12B75 genes. For the light chain expression plasmids, the complete J-C intron, constant region coding sequence and 3' flanking sequence were also derived from the 12B75 light chain gene. For the heavy chain expression plasmids that resulted in the final production cell lines (p1781 and p1783, see below), the human IgG1 constant region coding sequences derived from Centocor's previously-used expression vector (p104). Importantly, the final production cell lines reported here express a different allotype (Gm(f+)) of the TNV mAbs than the original, hybridoma-derived TNV mAbs (Glm(z)). This is because the 12B75 heavy chain gene derived from the GenPharm mice encodes an Arg residue at the C-terminal end of the CHI domain whereas Centocor's IgG1 expression vector p104 encodes a Lys residue at that position. Other heavy chain expression plasmids (e.g. p1786 and p1788) were prepared in which the J-C intron, complete constant region coding sequence and 3' flanking sequence were derived from the 12B75 heavy chain gene, but cell lines transfected with those genes were not selected as the production cell lines. Vectors were carefully designed to permit one-step cloning of future PCR-amplified V regions that would result in final expression plasmids.

PCR-amplified variable region cDNAs were transferred from L28 or pBC vectors to intermediate-stage, 12B75-based vectors that provided the promoter region and part of the J-C intron (see Table 2 for plasmid identification numbers). Restriction fragments that contained the 5' half of the antibody genes were then transferred from these intermediate-stage vectors to the final expression vectors that provided the 3' half of the respective genes to form the final expression plasmids (see Table 2 for plasmid identification numbers).

Cell Transfections and Subcloning. Expression plasmids were either linearized by restriction digest or the antibody gene inserts in each plasmid were purified away from the plasmid backbones. Sp2/0 and 653 mouse myeloma cells were transfected with the heavy and light chain DNA by electroporation. Fifteen different transfections were done, most of which were unique as defined by the Ab, specific characteristics of the Ab genes, whether the genes were on linearized whole plasmids or purified gene inserts, and the host cell line (summarized in Table 4). Cell supernatants from clones resistant to mycophenolic acid were assayed for the presence of human IgG by ELISA and quantitated using purified rTNV148B as a reference standard curve.

Highest-Producing rTNV148B Cell Lines

Ten of the best-producing 653 parental lines from rTNV148B transfection 2 (produced 5-10 :g/ml in spent 24-well cultures) were subcloned to screen for higher-producing cell lines and to prepare a more homogeneous cell population. Two of the subclones of the parental line 2.320, 2.320-17 and 2.320-20, produced approximately 50 :g/ml in spent 24-well cultures, which was a 5-fold increase over their parental line. A second round of subcloning of subcloned lines 2.320-17 and 2.320-20 led The identification numbers of the heavy and light chain plasmids that encode each mAb are shown. In the case of transfections done with purified mAb gene inserts, plasmid p13 (pSV2gpt) was included as a source of the gpt selectable marker. The heavy chain constant regions were encoded either by the same human IgG1 expression vector used to encode Remicade ('old') or by the constant regions contained within the 12B75 (GenPharm/Medarex) heavy chain gene ('new'). H1/L2 refers to a "novel" mAb made up of the TNV14 heavy chain and the TNV148 light chain. Plasmids p1783 and p1801 differ only by how much of the J-C intron their heavy chain genes contain. The transfection numbers, which define the first number of the generic names for cell clones, are shown on the right. The rTNV148B-producing cell lines C466 (A, B, C, D) and C467A described here derived from transfection number 2 and 1, respectively. The rTNV14-producing cell line C476A derived from transfection number 3.

TABLE 4

Summary of Cell Transfections.

| Plasmids | | HC DNA | | Transfection no. | |
|---|---|---|---|---|---|
| mAb | HC/LC/gpt | vector | format | Sp2/0 | 653 |
| rTNV148B | 1783/1776 | old | linear | 1 | 2 |
| rTNV14 | 1781/1775 | old | linear | 3 | — |
| rTNV148B | 1788/1776/13 | new | insert | 4, 6 | 5, 7 |
| rTNV14 | 1786/1775/13 | new | insert | 8, 10 | 9, 11 |
| rTNV148 | 1787/1776/13 | new | insert | 12 | 17 |
| rH1/L2 | 1786/1776/13 | new | insert | 13 | 14 |
| rTNV148B | 1801/1776 | old | linear | 16 | |

ELISA assays on spent 24-well culture supernatants indicated that these second-round subclones all produced between 98 and 124 :g/ml, which was at least a 2-fold increase over the first-round subclones. These 653 cell lines were assigned C code designations as shown in Table 5.

Three of the best-producing Sp2/0 parental lines from rTNV148B transfection 1 were subcloned. Two rounds of subcloning of parental line 1.73 led to the identification of a clone that produced 25 :g/ml in spent 24-well cultures. This Sp2/0 cell line was designated C467A (Table 5).

Highest-Producing rTNV14 Cell Lines

Three of the best-producing Sp2/0 parental lines from rTNV14 transfection 3 were subcloned once. Subclone 3.27-1 was found to be the highest-producer in spent 24-well cultures with a production of 19 :g/ml. This cell line was designated C476A (Table 5).

Table 5. Summary of Selected Production Cell Lines and their C Codes.

The first digit of the original clone names indicates which transfection the cell line derived from. All of the C-coded cell lines reported here were derived from transfections with heavy and light chain whole plasmids that had been linearized with restriction enzymes.

| Original mAb | Clone Name | C code | Host Cell | Production |
|---|---|---|---|---|
| rTNV148B | 2.320-17-36 | C466A | 653 | 103: g/ml |
|  | 2.320-20-111 | C466B | 653 | 102: g/ml |
|  | 2.320-17-4 | C466C | 653 | 98: g/ml |
|  | 2.320-20-99 | C466D | 653 | 124: g/ml |
|  | 1.73-12-122 | C467A | Sp2/0 | 25: g/ml |
| rTNV14 | 3.27-1 | C476A | Sp2/0 | 19: g/ml |

Characterization of Subcloned Cell Lines

Figure 7:
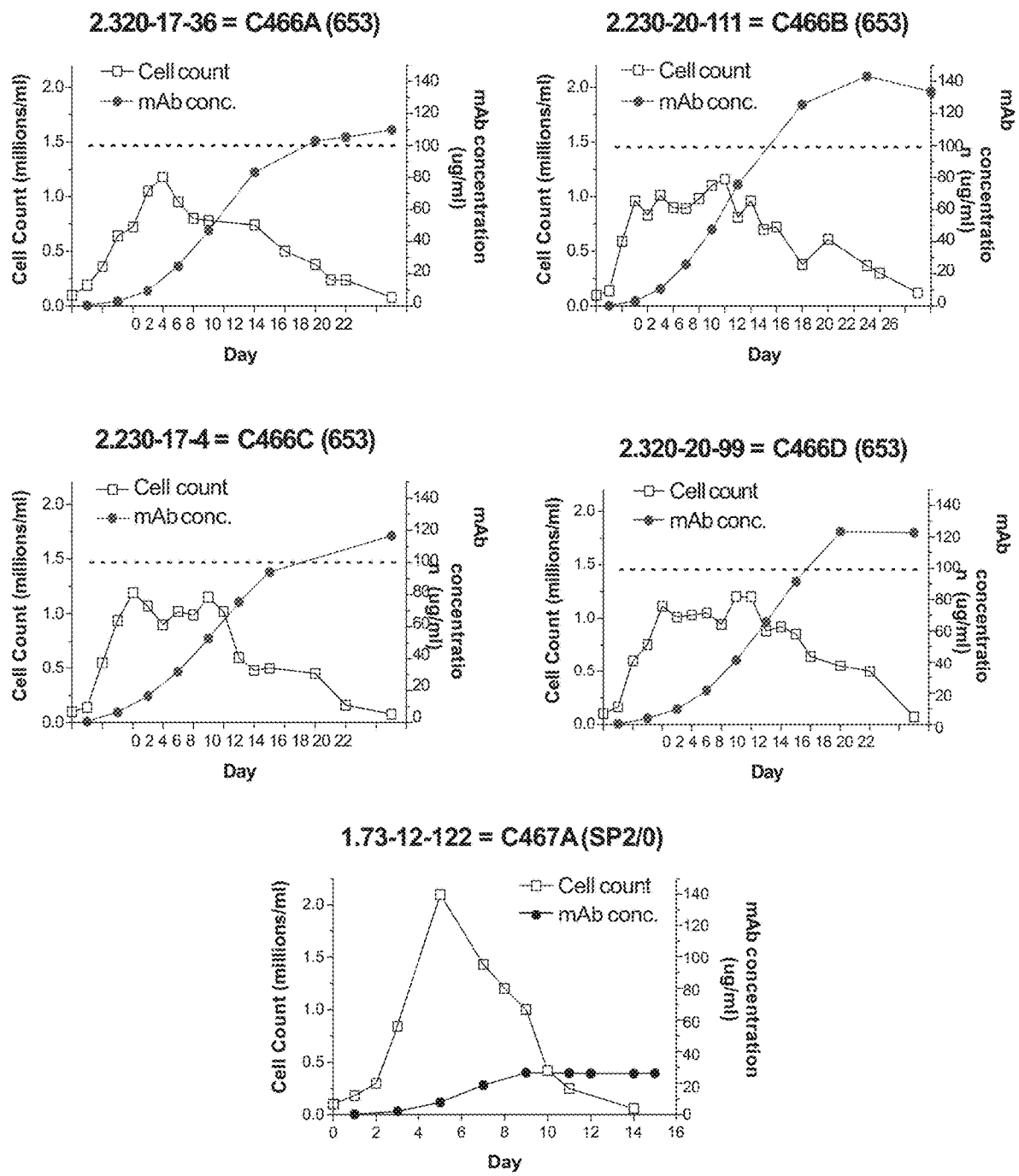
FIG. 7 shows graphical representation of growth curve analyses of five rTNV148B-producing cell lines. Cultures were initiated on day 0 by seeding cells into T75 flasks in I5Q+MHX media to have a viable cell density of $1.0 \times 10^5$ cells/ml in a 30 ml volume. The cell cultures used for these studies had been in continuous culture since transfections and subclonings were performed. On subsequent days, cells in the T flasks were thoroughly resuspended and a 0.3 ml aliquot of the culture was removed. The growth curve studies were terminated when cell counts dropped below $1.5 \times 10^5$ cells/ml. The number of live cells in the aliquot was determined by typan blue exclusion and the remainder of the aliquot stored for later mAb concentration determination. An ELISA for human IgG was performed on all sample aliquots at the same time.

To more carefully characterize cell line growth characteristics and determine mAb-production levels on a larger scale, growth curves analyses were performed using T75 cultures. The results showed that each of the four C466 series of cell lines reached peak cell density between $1.0 \times 10^6$ and $1.25 \times 10^6$ cells/ml and maximal mAb accumulation levels of between 110 and 140 :g/ml (FIG. 7). In contrast, the best-producing Sp2/0 subclone, C467A, reached peak cell density of $2.0 \times 10^6$ cells/ml and maximal mAb accumulation levels of 25 :g/ml (FIG. 7). A growth curve analysis was not done on the rTNV14-producing cell line, C476A.

Figure 8:
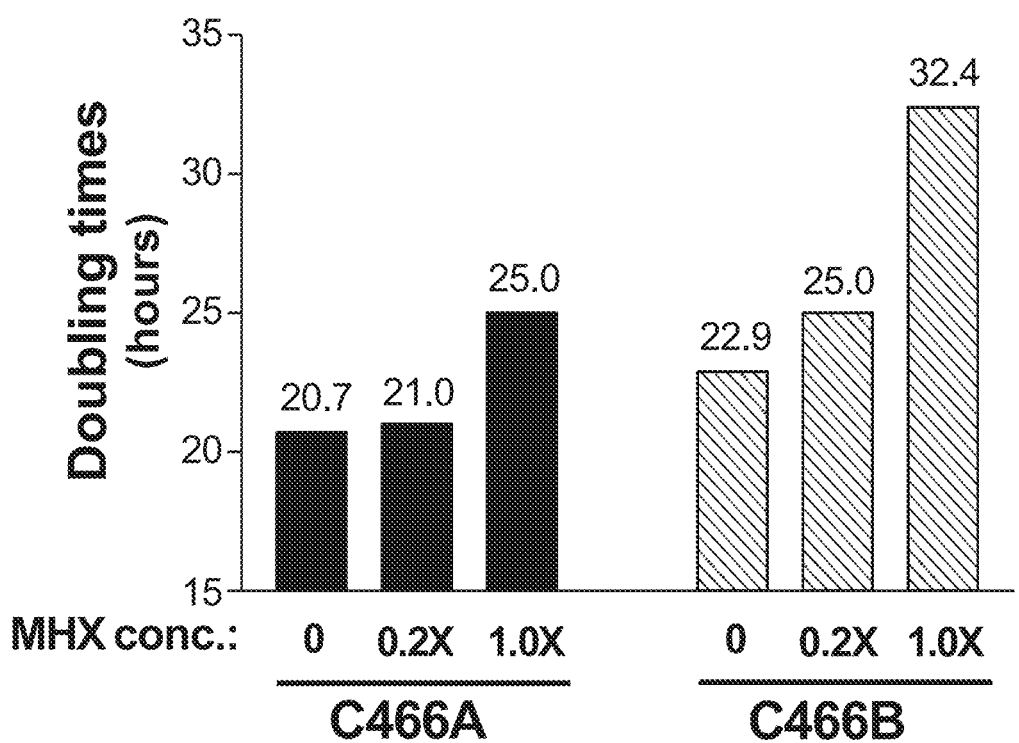
FIG. 8 shows a graphical representation of the comparison of cell growth rates in the presence of varying concentrations of MHX selection. Cell subclones C466A and C466B were thawed into MHX-free media (IMDM, 5% FBS, 2 mM glutamine) and cultured for two additional days. Both cell cultures were then divided into three cultures that contained either no MHX, 0.2×MHX, or 1×MHX. One day later, fresh T75 flasks were seeded with the cultures at a starting density of $1 \times 10^5$ cells/ml and cells counted at 24 hour intervals for one week. Doubling times during the first 5 days were calculated using the formula in SOP PD32.025 and are shown above the bars.

An additional growth curve analysis was done to compare the growth rates in different concentrations of MHX selection. This comparison was prompted by recent observations that C466 cells cultured in the absence of MHX seemed to be growing faster than the same cells cultured in the normal amount of MHX (1×). Because the cytotoxic concentrations of compounds such as mycophenolic acid tend to be measured over orders of magnitude, it was considered possible that the use of a lower concentration of MHX might result in significantly faster cell doubling times without sacrificing stability of mAb production. Cell lines C466A and C466B were cultured either in: no MHX, 0.2×MHX, or 1×MHX. Live cell counts were taken at 24-hour intervals for 7 days. The results did reveal an MHX concentration-dependent rate of cell growth (FIG. 8). Cell line C466A showed a doubling time of 25.0 hours in 1×MHX but only 20.7 hours in no MHX. Similarly, cell line C466B showed a doubling time of 32.4 hours in 1×MHX but only 22.9 hours in no MHX. Importantly, the doubling times for both cell lines in 0.2× MHX were more similar to what was observed in no MHX than in 1×MHX (FIG. 8). This observation raises the possibility than enhanced cell performance in bioreactors, for which doubling times are an important parameter, could be realized by using less MHX. However, although stability test results (see below) suggest that cell line C466D is capable of stably producing rTNV148B for at least 60 days even with no MHX present, the stability test also showed higher mAb production levels when the cells were cultured in the presence of MHX compared to the absence of MHX.

To evaluate mAb production from the various cell lines over a period of approximately 60 days, stability tests were performed on cultures that either contained, or did not contain, MHX selection. Not all of the cell lines maintained high mAb production. After just two weeks of culture, clone C466A was producing approximately 45% less than at the beginning of the study. Production from clone C466B also appeared to drop significantly. However, clones C466C and C466D maintained fairly stable production, with C466D showing the highest absolute production levels (FIG. 9).

Conclusion

From an initial panel of eight human mAbs against human TNFα, TNV148B was selected as preferred based on several criteria that included protein sequence and TNF neutralization potency, as well as TNV14. Cell lines were prepared that produce greater than 100 :g/ml of rTNV148B and 19 :g/ml rTNV14.

Example 5: Arthritic Mice Study Using Anti-TNF Antibodies and Controls Using Single Bolus Injection At approximately 4 weeks of age the Tg197 study mice were assigned, based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg.

Figure 10:
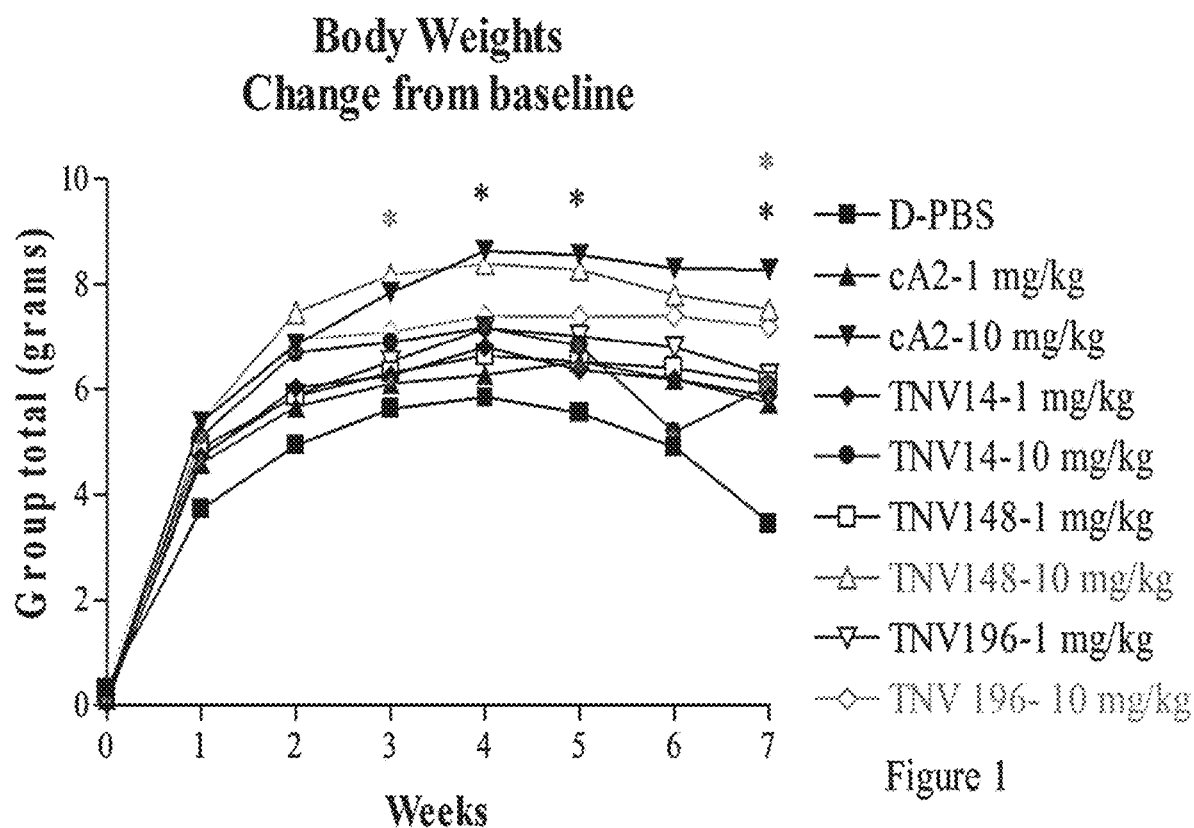
FIG. 10 shows arthritis mouse model mice Tg197 weight changes in response to anti-TNF antibodies of the present invention as compared to controls in Example 4. At approximately 4 weeks of age the Tg197 study mice were assigned, based on gender and body weight, to one of 9 treatment groups and treated with a single intraperitoneal bolus dose of Dulbecco's PBS (D-PBS) or an anti-TNF antibody of the present invention (TNV14, TNV148 or TNV196) at either 1 mg/kg or 10 mg/kg. When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study.

RESULTS: When the weights were analyzed as a change from pre-dose, the animals treated with 10 mg/kg cA2 showed consistently higher weight gain than the D-PBS-treated animals throughout the study. This weight gain was significant at weeks 3-7. The animals treated with 10 mg/kg TNV148 also achieved significant weight gain at week 7 of the study. (See FIG. 10).

Figure 11A:
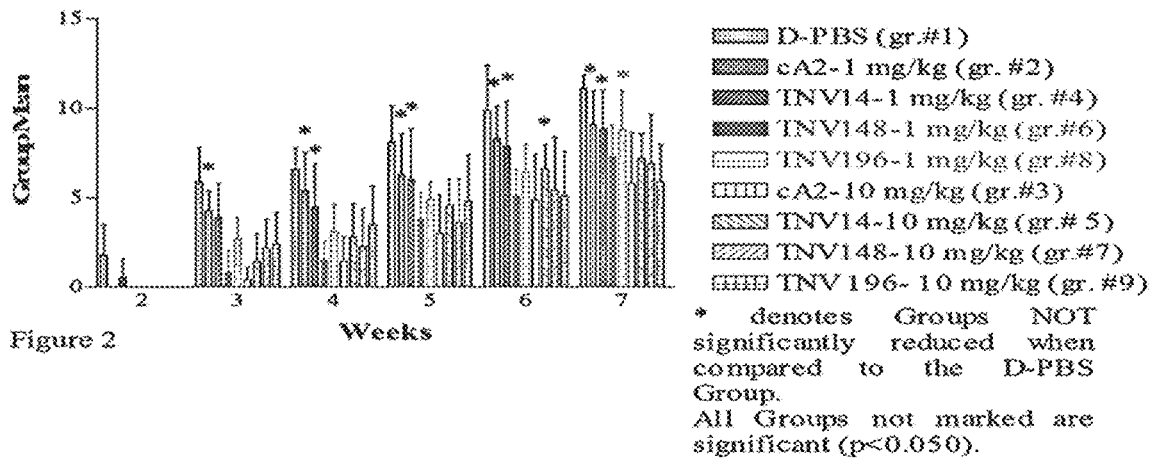
FIGS. 11A-C represent the progression of disease severity based on the arthritic index as presented in Example 4. The 10 mg/kg cA2-treated group's arthritic index was lower than the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV 14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.
Figure 11B:
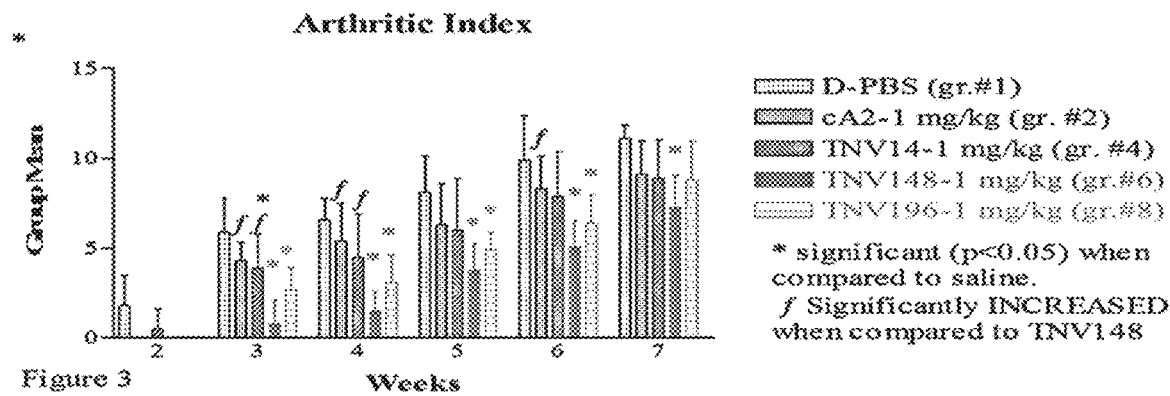
Figure 11C:
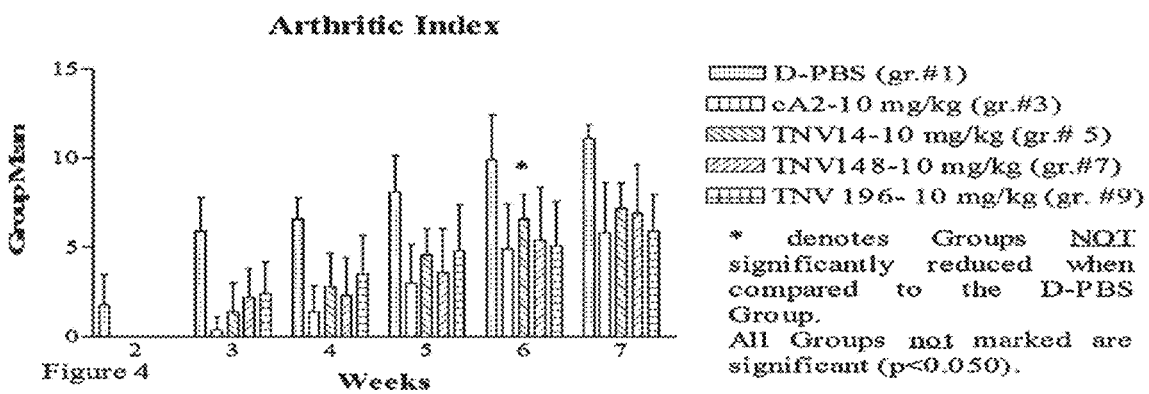

FIGS. 11A-C represent the progression of disease severity based on the arthritic index. The 10 mg/kg cA2-treated group's arthritic index was lower than the D-PBS control group starting at week 3 and continuing throughout the remainder of the study (week 7). The animals treated with 1 mg/kg TNV14 and the animals treated with 1 mg/kg cA2 failed to show significant reduction in AI after week 3 when compared to the D-PBS-treated Group. There were no significant differences between the 10 mg/kg treatment groups when each was compared to the others of similar dose (10 mg/kg cA2 compared to 10 mg/kg TNV14, 148 and 196). When the 1 mg/kg treatment groups were compared, the 1 mg/kg TNV148 showed a significantly lower AI than 1 mg/kg cA2 at 3, 4 and 7 weeks. The 1 mg/kg TNV148 was also significantly lower than the 1 mg/kg TNV14-treated Group at 3 and 4 weeks. Although TNV196 showed significant reduction in AI up to week 6 of the study (when compared to the D-PBS-treated Group), TNV148 was the only 1 mg/kg treatment that remained significant at the conclusion of the study.

Example 6: Arthritic Mice Study Using Anti-TNF Antibodies and Controls as Multiple Bolus Doses At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV148 at weeks 2, 3 and 4.

Figure 12:
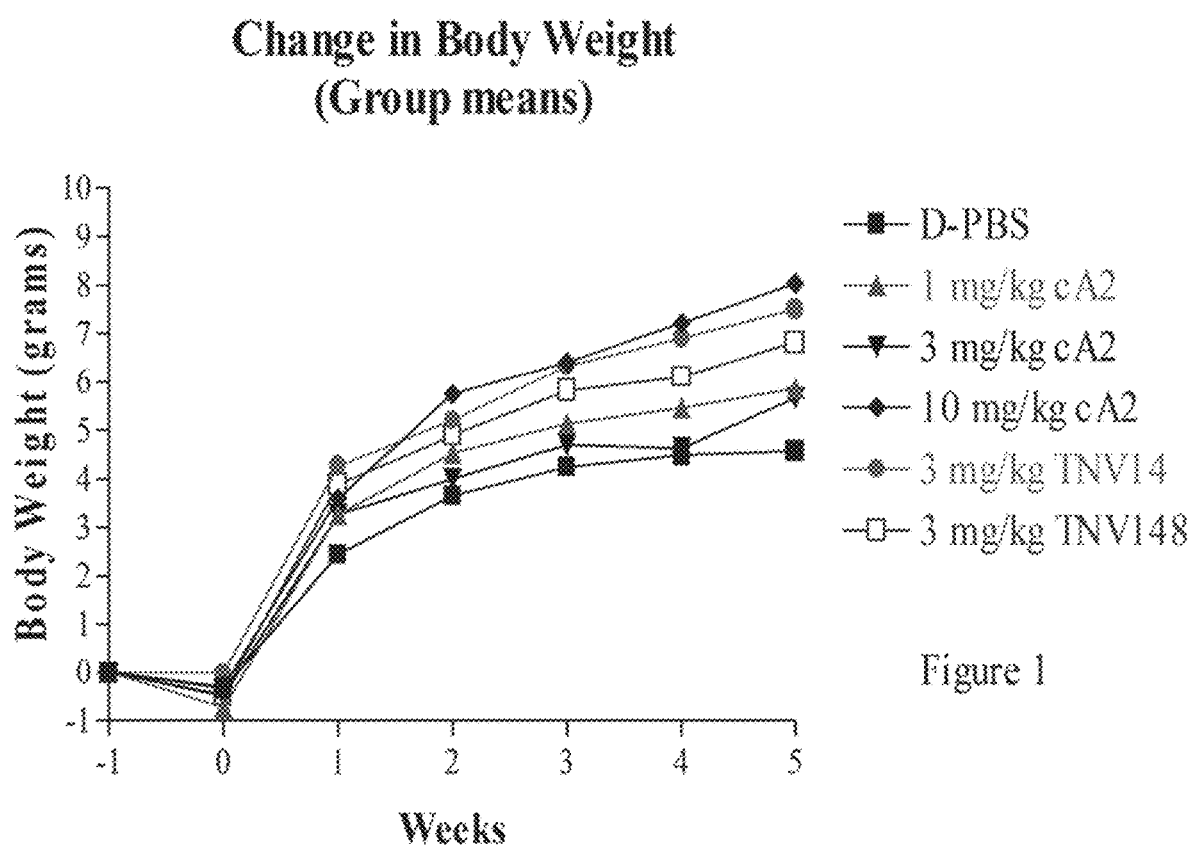
FIG. 12 shows arthritis mouse model mice Tg197 weight changes in response to anti-TNF antibodies of the present invention as compared to controls in Example 5. At approximately 4 weeks of age the Tg197 study mice were assigned, based on body weight, to one of 8 treatment groups and treated with a intraperitoneal bolus dose of control article (D-PBS) or antibody (TNV14, TNV148) at 3 mg/kg (week 0). Injections were repeated in all animals at weeks 1, 2, 3, and 4. Groups 1-6 were evaluated for test article efficacy. Serum samples, obtained from animals in Groups 7 and 8 were evaluated for immune response induction and pharmacokinetic clearance of TNV14 or TNV 148 at weeks 2, 3 and 4.

RESULTS: No significant differences were noted when the weights were analyzed as a change from pre-dose. The animals treated with 10 mg/kg cA2 showed consistently higher weight gain than the D-PBS-treated animals throughout the study. (See FIG. 12).

Figure 13A:
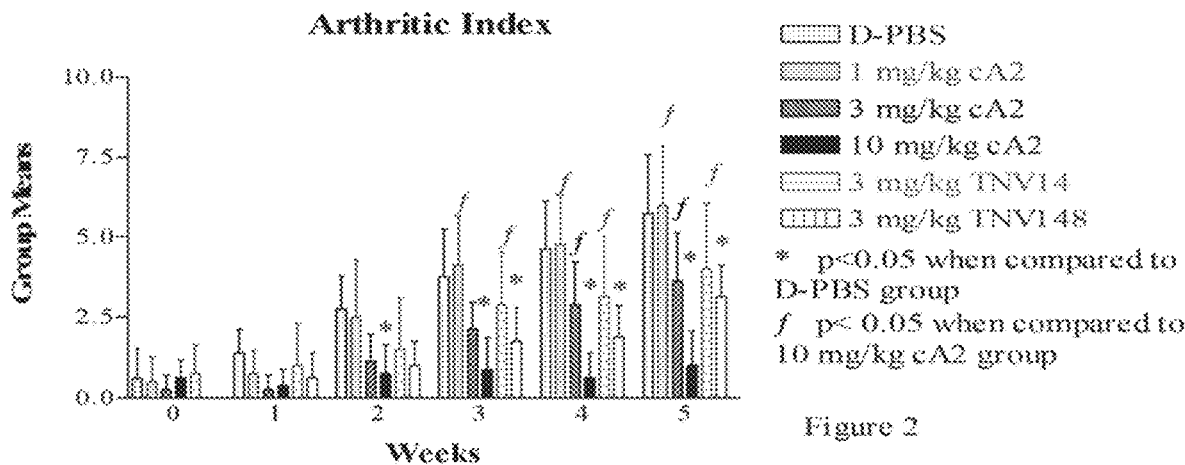
FIGS. 13A-C are graphs representing the progression of disease severity in Example 5 based on the arthritic index. The 10 mg/kg cA2-treated group's arthritic index was significantly lower than the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.
Figure 13B:
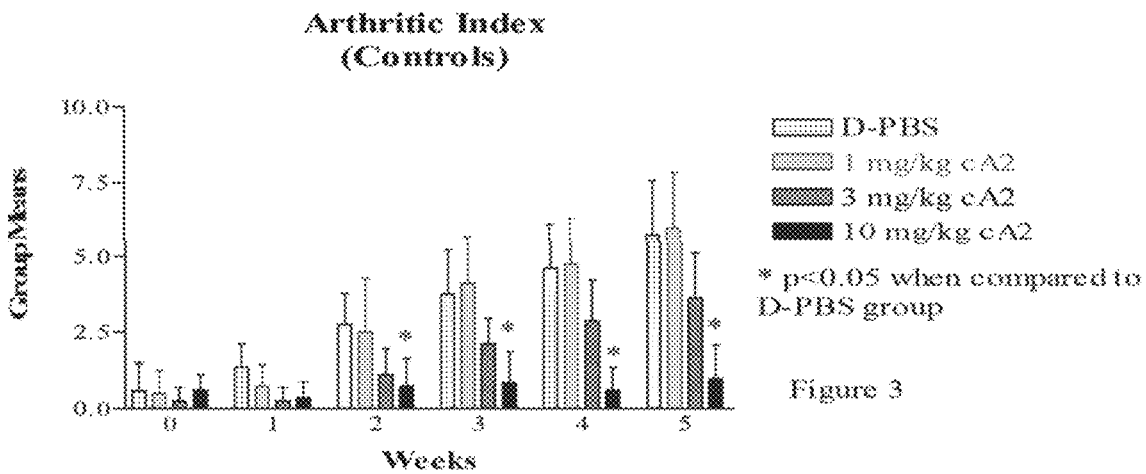
Figure 13C:
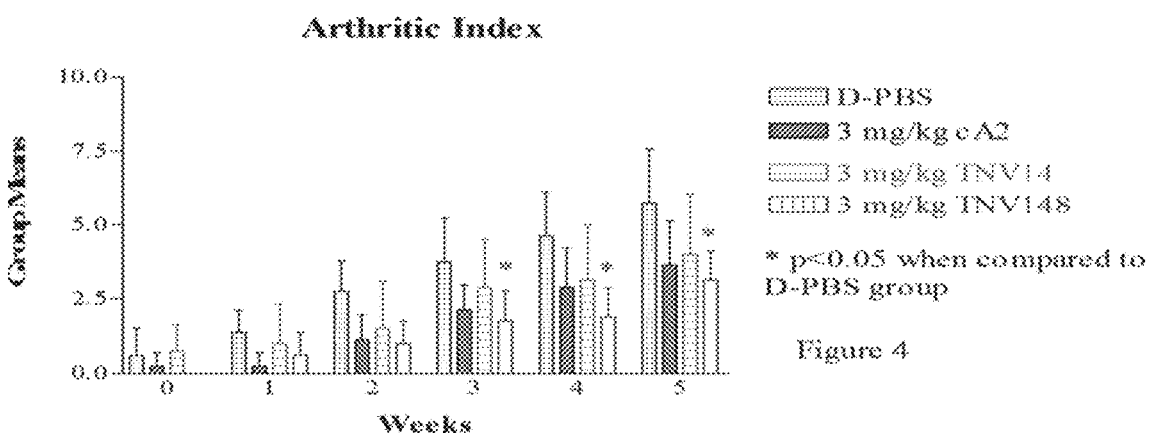

FIGS. 13A-C represent the progression of disease severity based on the arthritic index. The 10 mg/kg cA2-treated group's arthritic index was significantly lower than the D-PBS control group starting at week 2 and continuing throughout the remainder of the study (week 5). The animals treated with 1 mg/kg or 3 mg/kg of cA2 and the animals treated with 3 mg/kg TNV14 failed to achieve any significant reduction in AI at any time throughout the study when compared to the d-PBS control group. The animals treated with 3 mg/kg TNV 148 showed a significant reduction when compared to the d-PBS-treated group starting at week 3 and continuing through week 5. The 10 mg/kg cA2-treated animals showed a significant reduction in AI when compared to both the lower doses (1 mg/kg and 3 mg/kg) of cA2 at weeks 4 and 5 of the study and was also significantly lower than the TNV14-treated animals at weeks 3-5. Although there appeared to be no significant differences between any of the 3 mg/kg treatment groups, the AI for the animals treated with 3 mg/kg TNV14 were significantly higher at some time points than the 10 mg/kg whereas the animals treated with TNV148 were not significantly different from the animals treated with 10 mg/kg of cA2.

Example 7: Arthritic Mice Study Using Anti-TNF Antibodies and Controls as Single Intraperitoneal Bolus Dose At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

Figure 14:
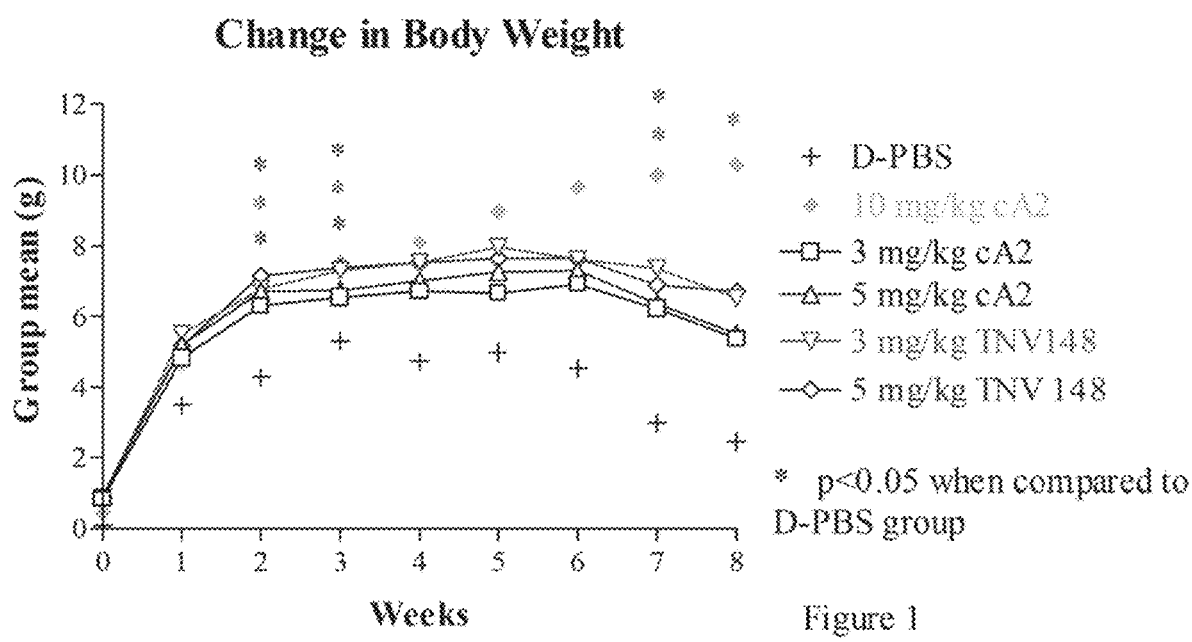
FIG. 14 shows arthritis mouse model mice Tg197 weight changes in response to anti-TNF antibodies of the present invention as compared to controls in Example 6. At approximately 4 weeks of age the Tg197 study mice were assigned, based on gender and body weight, to one of 6 treatment groups and treated with a single intraperitoneal bolus dose of antibody (cA2, or TNV148) at either 3 mg/kg or 5 mg/kg. This study utilized the D-PBS and 10 mg/kg cA2 control Groups.

When the weights were analyzed as a change from pre-dose, all treatments achieved similar weight gains. The animals treated with either 3 or 5 mg/kg TNV148 or 5 mg/kg cA2 gained a significant amount of weight early in the study (at weeks 2 and 3). Only the animals treated with TNV 148 maintained significant weight gain in the later time points. Both the 3 and 5 mg/kg TNV148-treated animals showed significance at 7 weeks and the 3 mg/kg TNV148 animals were still significantly elevated at 8 weeks post injection. (See FIG. 14).

Figure 15:
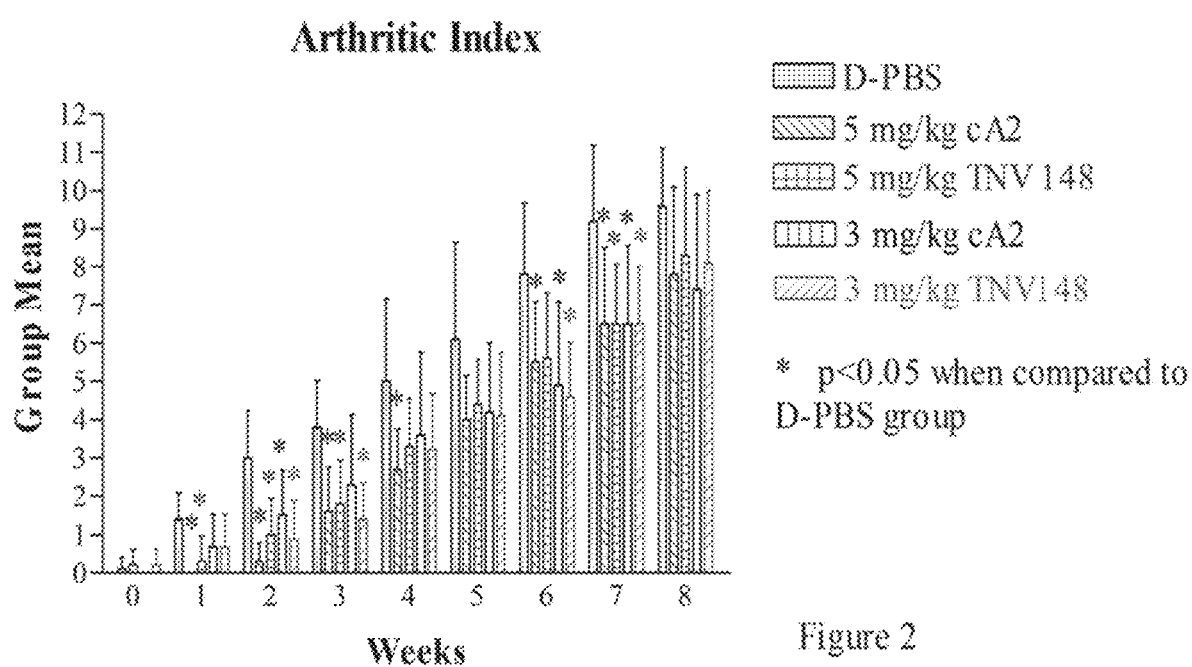
FIG. 15 represents the progression of disease severity based on the arthritic index as presented in Example 6. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

FIG. 15 represents the progression of disease severity based on the arthritic index. All treatment groups showed some protection at the earlier time points, with the 5 mg/kg cA2 and the 5 mg/kg TNV148 showing significant reductions in AI at weeks 1-3 and all treatment groups showing a significant reduction at week 2. Later in the study the animals treated with 5 mg/kg cA2 showed some protection, with significant reductions at weeks 4, 6 and 7. The low dose (3 mg/kg) of both the cA2 and the TNV 148 showed significant reductions at 6 and all treatment groups showed significant reductions at week 7. None of the treatment groups were able to maintain a significant reduction at the conclusion of the study (week 8). There were no significant differences between any of the treatment groups (excluding the saline control group) at any time point.

Example 8: Arthritic Mice Study Using Anti-TNF Antibodies and Controls as Single Intraperitoneal Bolus Dose Between Anti-TNF Antibody and Modified Anti-TNF Antibody To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco=S PBS (D-PBS) or antibody (TNV148, rTNV148B) at 1 mg/kg.

Figure 16:
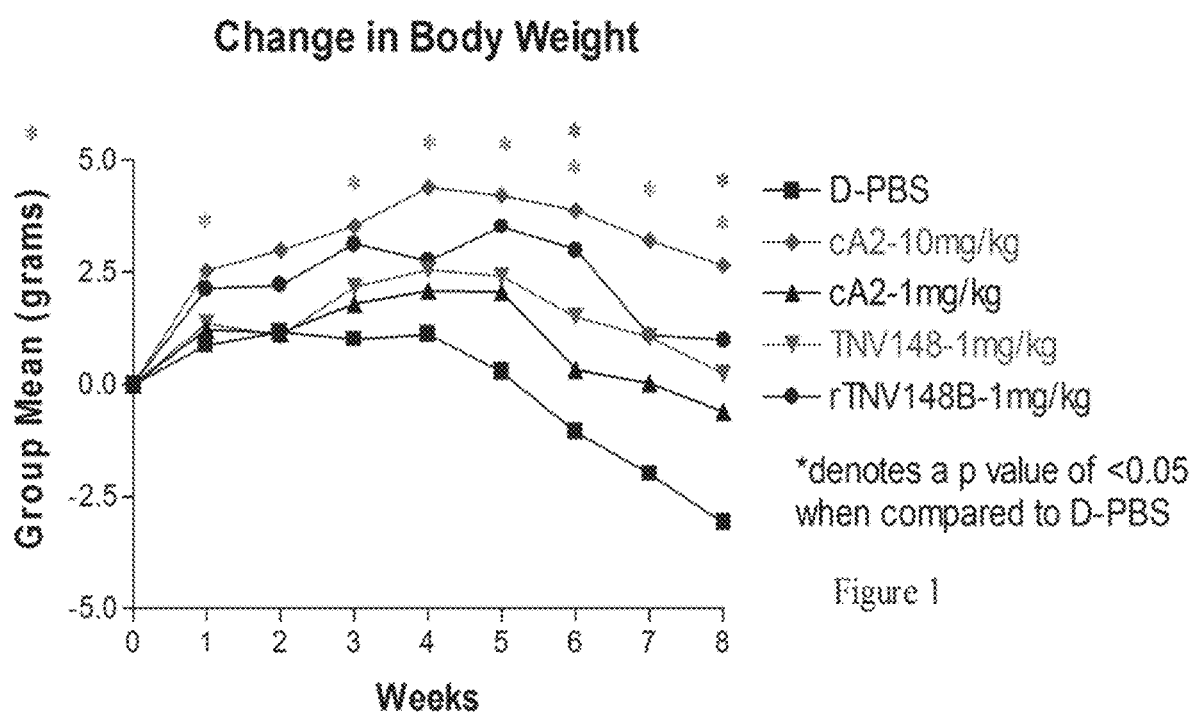
FIG. 16 shows arthritis mouse model mice Tg197 weight changes in response to anti-TNF antibodies of the present invention as compared to controls in Example 7. To compare the efficacy of a single intraperitoneal dose of TNV148 (derived from hybridoma cells) and rTNV148B (derived from transfected cells). At approximately 4 weeks of age the Tg197 study mice were assigned, based on gender and body weight, to one of 9 treatment groups and treated with a single intraperitoneal bolus dose of Dulbecco's PBS (D-PBS) or antibody (TNV148, rTNV148B) at 1 mg/kg.

When the weights were analyzed as a change from pre-dose, the animals treated with 10 mg/kg cA2 showed a consistently higher weight gain than the D-PBS-treated animals throughout the study. This weight gain was significant at weeks 1 and weeks 3-8. The animals treated with 1 mg/kg TNV148 also achieved significant weight gain at weeks 5, 6 and 8 of the study. (See FIG. 16).

Figure 17:
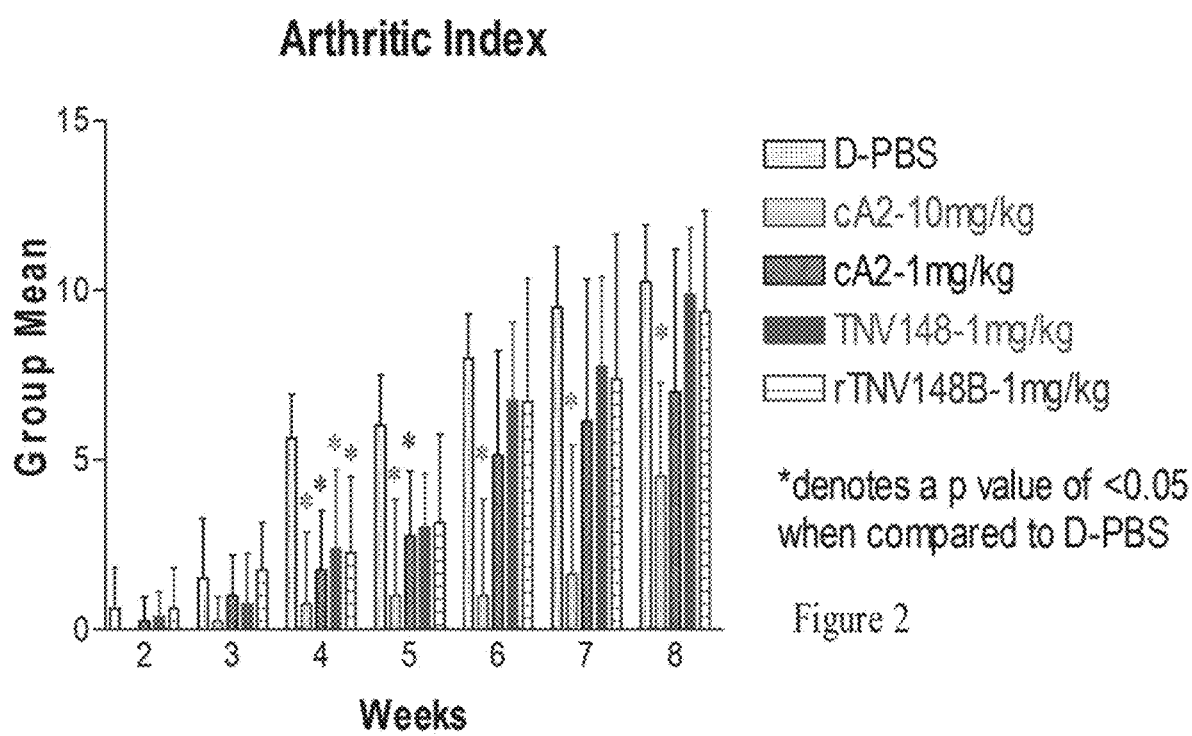
FIG. 17 represents the progression of disease severity based on the arthritic index as presented in Example 7. The 10 mg/kg cA2-treated group's arthritic index was lower than the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

FIG. 17 represents the progression of disease severity based on the arthritic index. The 10 mg/kg cA2-treated group's arthritic index was lower than the D-PBS control group starting at week 4 and continuing throughout the remainder of the study (week 8). Both of the TNV148-treated Groups and the 1 mg/kg cA2-treated Group showed a significant reduction in AI at week 4. Although a previous study (P-099-017) showed that TNV148 was slightly more effective at reducing the Arthritic Index following a single 1 mg/kg intraperitoneal bolus, this study showed that the AI from both versions of the TNV antibody-treated groups was slightly higher. Although (with the exception of week 6) the 1 mg/kg cA2-treated Group was not significantly increased when compared to the 10 mg/kg cA2 group and the TNV148-treated Groups were significantly higher at weeks 7 and 8, there were no significant differences in AI between the 1 mg/kg cA2, 1 mg/kg TNV148 and 1 mg/kg TNV148B at any point in the study.

Example 9: Anti-TNF Antibody for the Treatment of Active Psoriatic Arthritis

Synopsis
A Multicenter, Randomized, Double-blind, Placebo-controlled Trial of Golimumab, an Anti-TNFα Monoclonal Antibody, Administered Intravenously, in Subjects with Active Psoriatic Arthritis (PsA)

SIMPONI® (golimumab) is a fully human monoclonal antibody with an Immunoglobulin G 1 (IgG1) heavy chain isotype (G1m[z] allotype) and a kappa light chain isotype. Golimumab has a heavy chain (HC) comprising SEQ ID NO:36 and a light chain (LC) comprising SEQ ID NO:37. The molecular weight of golimumab ranges from 149,802 to 151,064 daltons. Golimumab binds to human tumor necrosis factor alpha (TNFα) with high affinity and specificity and neutralizes TNFα bioactivity.

Objectives and Hypothesis
Primary Objective
The primary objective of this study is to evaluate the efficacy of IV administration of golimumab 2 mg/kg in subjects with active psoriatic arthritis (PsA) by assessing the reduction in signs and symptoms of PsA.

Secondary Objectives

The secondary objectives are to assess the following for IV golimumab:

Efficacy related to improving psoriatic skin lesions, physical function, health-related quality of life, and other health outcomes Inhibition of progression of structural damage Safety Pharmacokinetics (PK), pharmacodynamics (PD), and immunogenicity Hypothesis To address the primary objective of the study, the statistical hypothesis (alternative hypothesis) is that golimumab 2 mg/kg is statistically superior to placebo in reducing the signs and symptoms of subjects with active PsA based on the primary efficacy endpoint.

The primary endpoint of this study is the proportion of subjects who achieve a 20% improvement from baseline in the American College of Rheumatology criteria (called ACR 20) at Week 14. This endpoint was chosen because it is well-accepted by regulatory authorities and the clinical PsA community.

Overview of Study Design

This is a Phase 3 multicenter, randomized, double-blind, placebo-controlled study of the efficacy and safety of IV golimumab compared with placebo in subjects with active PsA. Approximately 440 subjects will be randomized at approximately 90 investigational sites. Subjects will be randomly assigned to receive golimumab 2 mg/kg or placebo IV infusions at Weeks 0, 4, 12, and 20. At Week 16, all subjects who qualify for early escape will be allowed one of the following concomitant medication interventions, as selected by the investigator: an increase in their corticosteroid dose (maximum total dose prednisone 10 mg/day, or equivalent), methotrexate (MTX) dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit. At Week 24, all subjects receiving placebo infusions will cross over and begin receiving golimumab IV infusions.

Subjects in the golimumab IV treatment group will continue to receive golimumab IV infusions. Database locks (DBL) are scheduled for Weeks 24 and 60. Subjects will be followed for adverse events (AE) and serious adverse events (SAE) at least 8 weeks following the last study treatment administration. The end of study is defined as the time the last subject completes the Week 60 visit.

Subject Population

Subjects eligible for the study will be men or women 18 years of age or older with PsA for at least 6 months prior to the first administration of study agent and meet CASPAR criteria at screening. Subjects must have symptoms of active disease (5 or more swollen joints and 5 or more tender joints) at screening and at baseline and have a C-reactive protein (CRP) level of ≥0.6 mg/dL. Subjects must not have been treated with biologics. Subjects may continue MTX treatment during the study.

Screening for eligible subjects will be performed within 6 weeks before administration of the study agent.

Subjects must also meet the inclusion and exclusion criteria.

Dosage and Administration

At the initial screening visit, informed consent will be obtained from all subjects who are deemed potentially eligible for the study, according to the protocol-specified inclusion and exclusion criteria, for enrollment in the study. At the randomization visit, subjects will be re-assessed and, if all specified inclusion and exclusion criteria are met, subjects will be randomized to receive either golimumab IV infusions or placebo IV infusions. Randomization will be stratified by geographic region and baseline methotrexate (MTX) use (yes, or no).

Before the first infusion of study agent, subjects will be randomly assigned in a 1:1 ratio to 1 of the following 2 treatment groups:

Group 1 (n=220): Subjects will receive IV placebo infusions at Weeks 0, 4, 12, and 20. Subjects will switch to IV golimumab 2 mg/kg at Week 24, and receive administrations at Weeks 24, 28, and q8w thereafter.

Group 2 (n=220): Subjects will receive IV golimumab 2 mg/kg at Weeks 0, 4, and q8w thereafter. Subjects will receive an IV placebo infusion at Week 24 to maintain the blind.

At Week 16, all subjects in Groups I and II with <5% improvement from baseline in both tender and swollen joint counts will enter early escape (EE). At Week 16, all subjects who qualify for early escape will be allowed one of the following concomitant medication interventions, as selected by the investigator: an increase in their corticosteroid dose (maximum total dose prednisone 10 mg/day, or equivalent), MTX dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit.

All infusions will be completed over 30±10 minutes.

Efficacy Evaluations/Endpoints

Efficacy evaluations chosen for this study were established in previous trials of therapeutic biologic agents for the treatment of PsA. Patient reported outcomes (PRO) chosen for this study are consistent with clinically relevant measurements that are accepted in the medical literature for other studies in PsA and applicable US/EU regulatory guidance documents.

Psoriatic arthritis and psoriasis response evaluations include:

Subject's Assessment of Pain

Subject's Global Assessment of Disease

Physician's Global Assessment of Disease

Joint Assessment

Disability Index of the Health Assessment Questionnaire (HAQ-DI)

Psoriasis Area and Severity Index (PASI)

X-ray evaluations of hands and feet 36-item short form health survey (SF-36)

Dactylitis Assessment

Enthesitis Assessment

Bath Ankylosing Spondylitis Disease Activity Index (BASDAI)

Modified NAPSI

Dermatology Life Quality Index (DLQI)

Functional Assessment of Chronic Illness Therapy (FACIT)—Fatigue

Work Limitations Questionnaire (WLQ)

Productivity VAS

EuroQol-5D (EQ-5D) Questionnaire

Primary Endpoint

The primary endpoint of this study is the proportion of subjects who achieve an ACR 20 response at Week 14.

The study will be considered positive if the proportion of subjects with ACR 20 at Week 14 is demonstrated to be significantly greater in the golimumab group compared with the placebo group.

Major Secondary Endpoints

The following major secondary analyses endpoints are listed in order of importance as specified below:

The change from baseline in the HAQ-DI score at Week 14.

The proportion of subjects with ACR 50 response at Week 14.

The proportion of subjects (with baseline ≥3% BSA psoriatic involvement) who achieve a PASI 75 response at Week 14.

The change from baseline in total modified van der Heijde-Sharp (vdH-S) score at Week 24.

Pharmacokinetic Evaluations

Blood samples will be collected at selected visits to evaluate the PK of IV golimumab in adult subjects with PsA. Pharmacokinetic samples should be drawn from a different arm than the IV infusion line if study agent is administered at that visit. At the Weeks 0, 4, 12, 20, 36, and 52 visits, 2 samples for serum golimumab concentrations will be collected: 1 sample will be collected immediately prior to infusion and the other collected one hour after the end of the infusion. For each of the remaining visits, only 1 sample for serum golimumab concentrations will be collected, which should be collected immediately prior to infusion if an infusion of the study agent is administered at that visit. A random PK sample will also be drawn for population PK analysis between the Week 14 and Week 20 visits (other than at the time of the Week 14 or Week 20 visit); this random sample must be collected at least 24 hours prior to or after a study agent infusion.

At applicable time points, sera for the measurement of both golimumab concentration and antibodies to golimumab will be derived from the same blood draw.

Immunogenicity Evaluations

To evaluate the immunogenicity of golimumab in adult subjects with PsA, serum samples for the detection of antibodies to golimumab will be collected according to the Time and Events Schedule.

Biomarker Evaluations

Biomarker samples will be collected to gain a molecular understanding of inter-individual variability in clinical outcomes, which may help to identify population subgroups that respond differently to the drug. The biomarker samples may also be used to help address emerging issues and to enable the development of safer, more effective, and ultimately individualized therapies in the future.

Pharmacogenomics (DNA) Evaluations

Genomic testing will be done to search for links of specific genes to disease or response to drug. Only DNA research related to golimumab or to the diseases for which this drug is developed will be performed. Genome wide pharmacogenomics and/or epigenetics testing will be undertaken in this study in consenting subjects. Subjects participating in this portion of the study must sign a separate informed consent. Further, a subject may withdraw such consent at any time without affecting their participation in other aspects of the study, or their future participation in the study.

Pharmacogenomics blood samples will be collected to allow for pharmacogenomics research, as necessary (where local regulations permit). Subject participation in the pharmacogenomics research is optional.

Safety Evaluations

Based upon the safety profile of other anti-TNFα agents, as well as the golimumab safety data to date, several AEs of interest have been identified and will be monitored and assessed in this study. These include: infusion reactions, hepatobiliary laboratory abnormalities, infections including TB, and malignancies.

Statistical Methods

To assess the comparability of subject baseline, demographic, and baseline disease characteristics data will be summarized by treatment group.

Binary categorical data (eg, the proportion of subjects with an ACR 20 response) will be analyzed using the chi-square test or the Cochran Mantel Haenszel (CMH) test when stratification is employed. Continuous data will be analyzed using an analysis of variance (ANOVA). Van der Waerden normal scores will be utilized if endpoints are deemed non-Gaussian. All efficacy analyses will be based on the intent-to-treat principle; thus, subjects will be analyzed according to the treatment for which they were randomized regardless of the treatment they actually receive.

All statistical testing will be performed at an alpha level of 0.05 (2-sided). Both tabular and graphical summaries of data will be utilized.

Population Set

Efficacy and subject baseline analyses will utilize an intent-to-treat population (i.e., all subjects who are randomized) unless otherwise stated. Subjects included in the efficacy analyses will be summarized according to their assigned treatment group regardless of whether or not they receive the assigned treatment.

Safety and PK analyses will include all subjects who received at least one administration of study treatment.

Endpoint Analyses

Primary Endpoint Analysis

The primary endpoint is the proportion of subjects achieving an ACR 20 response at Week 14.

Reduction in signs and symptoms of arthritis will be evaluated by comparing the proportion of subjects with an ACR 20 response at Week 14 between the treatment groups. A CMH test, stratified by baseline MTX use (yes, or no) will be performed for this analysis at a significance level of 0.05.

A last observation carried forward (LOCF) procedure will be used to impute the missing ACR components if the subjects have data for at least 1 ACR component at Week 14. If the subjects do not have data for all the ACR components at Week 14, the subjects will be considered non-responders. In addition, treatment failure rules will be applied.

Major Secondary Endpoint Analyses

The following major secondary analyses will be performed in order of importance as specified below:
1. The change from baseline in the HAQ-DI score at Week 14 will be summarized and compared between treatment groups.
2. The proportion of subjects with ACR 50 response at Week 14 will be summarized and compared between treatment groups.
3. The proportion of subjects (with baseline ≥3% body surface area psoriatic involvement) who achieve a PASI 75 response at Week 14 will be summarized and compared between treatment groups.
4. The change from baseline in total modified vdH-S score at Week 24 will be summarized and compared between treatment groups.

To maintain the Type I error among the primary and major secondary endpoints, the endpoints will be tested sequentially. The primary endpoint will be analyzed. If that is statistically significant, then the major secondary endpoints will be compared in the order noted above if the previous major secondary endpoint is statistically significant. If the previous major secondary endpoint is not statistically significant, no further comparisons will be made. Nominal p-values will be provided.

Safety Analysis Overview

Routine safety evaluations will be performed. The occurrences and type of AEs, SAEs, and reasonably related AEs including infusion reactions and infections including TB, will be summarized by treatment groups. The number of subjects with abnormal laboratory parameters (hematology and chemistry) based on NCI CTCAE toxicity grading will be summarized. In addition, the number of subjects with ANA and anti-dsDNA antibodies and the relationship of infusion reactions with antibodies to golimumab will be summarized.

All safety analyses will be performed using the population of all subjects who received at least 1 administration of study agent. Analyses will be performed using the treatment that the subjects actually received.

In addition, graphical data displays (eg, line plots) and subject listings may also be used to summarize/present data.

Abbreviations
  ACR American College of Rheumatology
  AE adverse event
  ALT alanine aminotransferase
  ANOVA analysis of variance
  AS ankylosing spondylitis
  AST aspartate aminotransferase
  BASDAI Bath Ankylosing Spondylitis Disease Activity Index
  BCG Bacille Calmette-Guérin
  BSA body surface area
  CASPAR ClASsification criteria for Psoriatic ARthritis
  CHF congestive heart failure
  CRP C-reactive protein
  DAS Disease Activity Index Score
  DBL database lock
  DIP distal interphalangeal
  DLQI Dermatology Life Quality Index
  DMARDs disease-modifying antirheumatic drugs
  DMC Data monitoring committee
  DNA deoxyribonucleic acid
  EC Ethics Committee
  ECG electrocardiogram
  eCRF electronic case report form
  eDC electronic data capture
  EQ-5D EuroQol-5D
  EQ-VAS EQ visual analogue scale
  EU European Union
  FACIT-F Functional Assessment of Chronic Illness Therapy-Fatigue
  GCP Good Clinical Practice
  GLM Golimumab
  HAQ Health Assessment Questionnaire
  HBV hepatitis B virus
  HCQ hydroxychloroquine
  HCV hepatitis C virus
  HIV human immunodeficiency virus
  IB Investigator's Brochure
  ICH International Conference on Harmonisation
  IgG1 Immunoglobulin G 1
  IJA independent joint assessor
  IL interleukin
  IMPACT Infliximab Multinational Psoriatic Arthritis Controlled Trial
  IRB Institutional Review Board
  IRC Imaging Research Center
  IV intravenous
  IWRS interactive web response system
  JSN joint space narrowing
  mAb Monoclonal antibody
  MCP metacarpophalangeal
  MCS mental Component Summary
  MDA minimal disease activity
  MMP-1 matrix metalloproteinase-1
  MMP-3 matrix metalloproteinase-3
  MTX Methotrexate
  NAPSI Nail Psoriasis Severity Index
  NCI-CTCAE National Cancer Institute-Common Terminology Criteria for Adverse Events
  NSAID nonsteroidal anti-inflammatory drug
  PASI Psoriatic Area and Severity Index
  PBO Placebo
  PCS physical Component Summary
  PD pharmacodynamics(s)
  PIP proximal interphalangeal
  PK pharmacokinetic(s)
  PRO patient reported outcome
  PsA
  psoriatic arthritis
  patients
  pts
  q8w every 8 weeks
  q12w Every 12 weeks
  RA rheumatoid arthritis
  RBC red blood cell
  RF rheumatoid factor
  SAE serious adverse event
  SAP Statistical Analysis Plan
  SC subcutaneous
  SDC smallest detectable change
  SF-36 36-item short form health survey
  SI International System of Units
  SSZ sulfasalazine
  TB tuberculosis
  TNF tumor necrosis factors
  TST tuberculin skin test
  VAS Visual Analogue Scale
  vdH-S van der Heijde-Sharp
  WBC white blood cell
  WLQ Work Limitations Questionnaire Introduction Chemical Name and Structure SIMPONI® (golimumab) is a human monoclonal antibody (mAb) with an immunoglobulin G (IgG) 1 heavy chain isotype (G1m [z] allotype) and a kappa light chain isotype. Golimumab has a heavy chain (HC) comprising SEQ ID NO:36 and a light chain (LC) comprising SEQ ID NO:37. The molecular weight of golimumab ranges from 149,802 to 151,064 daltons. Golimumab is classified according to the Anatomical Therapeutic Chemical (ATC) Classification System as a TNFα inhibitor (ATC code: L04AB06). Golimumab binds with high affinity to both soluble and transmembrane forms of tumor necrosis factor alpha (TNFα) and inhibits TNFα bioactivity. No binding to other TNF super-family ligands was observed; in particular, golimumab does not bind or neutralize human lymphotoxin. TNFα is synthesized primarily by activated monocytes, macrophages and T cells as a transmembrane protein that selfassociates to form the bioactive homotrimer and is rapidly released from the cell surface by proteolysis. The binding of TNFα to either the p55 or p75 TNF receptors leads to the clustering of the receptor cytoplasmic domains and initiates signaling. Tumor necrosis factor has been identified as a key sentinel cytokine that is produced in response to various stimuli and subsequently promotes the inflammatory response through activation of the caspase-dependent apoptosis pathway and the transcription factors nuclear factor (NF)-κB and activator protein-1 (AP-1). Tumor necrosis factor also modulates the immune response through its role in the organization of immune cells in germinal centers. Elevated expression of TNF has been linked to chronic inflammatory diseases such as rheumatoid arthritis (RA), as well as spondyloarthropathies such as psoriatic arthritis (PSA) and ankylosing spondylitis (AS), and is an important mediator of the articular inflammation and structural damage that are characteristic of these diseases.

Psoriatic Arthritis

Psoriatic arthritis is a chronic, inflammatory, usually rheumatoid factor (RF) negative arthritis that is associated with psoriasis. The prevalence of psoriasis in the general Caucasian population is approximately 2%. Approximately 6% to 39% of psoriasis patients develop PsA.

Psoriatic arthritis peaks between the ages of 30 and 55 years and affects men and women equally. Psoriatic arthritis involves peripheral joints, axial skeleton, sacroiliac joints, nails, and entheses, and is associated with psoriatic skin lesions. More than half of the patients with PsA may have evidence of erosions on x-rays, and up to 40% of the patients develop severe, erosive arthropathy. Psoriatic arthritis leads to functional impairment, reduced quality of life, and increased mortality.

Interactions between T-cells and monocytes/macrophages, the primary source of proinflammatory cytokines, play a role in the pathogenesis of PsA. Increased levels of TNFα have been detected in joint fluid and tissues, and in psoriatic skin lesions in patients with PsA.

Role of TNFα in Psoriatic Arthritis

TNFα is considered a key inflammatory mediator that exhibits a wide variety of functional activities.[2] Overproduction of TNFα leads to the disease processes associated with inflammation, as demonstrated in patients with RA and Crohn's disease. Interactions between Tcells and monocytes/macrophages, the primary source of proinflammatory cytokines, play a role in pathogenesis of PsA.[7,22] Increased levels of TNFα have been detected in joint fluid and tissues, and in psoriatic skin lesions in patients with PsA.[24,26] Treatment with infliximab, an anti-TNFα monoclonal antibody, was reported to result in a significant reduction in the number of T-cells in psoriatic epidermis and in the number of T-cells and macrophages in the synovial tissue in patients with active PsA within 48 hours.[17] Infliximab treatment also significantly reduced angiogenic growth factors in synovial tissue in patients with PsA in parallel with dramatic clinical skin and joint responses.[32]

Biologic treatments targeting TNF, including infliximab, SC golimumab, adalimumab, and certolizumab pegol, have been shown to induce rapid and significant improvement of arthritis and psoriasis in subjects with active PsA while maintaining an acceptable safety profile. Etanercept, adalimumab, and certolizumab pegol are administered twice weekly, weekly, or every 2 to 4 weeks by SC injection. Golimumab is administered monthly by SC injection. Infliximab is administered as an IV infusion in an office-based setting at Weeks 0, 2, 6, and every 8 weeks thereafter.

In a Phase 3 study of SC golimumab in PsA (C0524T08), 405 subjects with PsA despite current or previous DMARD or NSAID therapy were randomized to receive SC placebo, golimumab 50 mg q4w, or 100 mg q4w. Treatment with golimumab resulted in improvement in signs and symptoms as demonstrated by percent of patients achieving ACR 20 response at Week 14: 51% (golimumab 50 mg) compared with 9% (placebo). At Week 24, the golimumab 50 mg group had significantly less radiographic damage than placebo, as measured by the mean change from baseline in total vdH-S score modified for PsA. Golimumab 100 mg group demonstrated less radiographic damage compared with placebo at Week 24, however, the difference did not reach statistical significance. Clinical improvements in PsA subjects previously seen at Week 24 were maintained through Week 256. Through Week 24, 65% and 59% of all golimumab-treated and placebo-treated patients, respectively, had adverse events. The most frequently reported adverse events in the golimumab groups were nasopharyngitis and upper respiratory tract infection. Serious adverse events (SAE) were reported for 2% of all golimumab-treated patients versus 6% of placebo-treated patients.

While the precise role of TNFα in the pathophysiology of PsA is yet unclear, there is already a large and mounting body of evidence that TNFα inhibition is of major therapeutic benefit in this disease.

Overall Rationale for the Study

This study will evaluate the safety and efficacy of 2 mg/kg of golimumab administered via IV infusion over 30 minutes at Weeks 0 and 4, then every 8 weeks (q8w; with or without MTX) in the treatment of active PsA.

Given the safety and efficacy of SC golimumab, it was hypothesized that IV golimumab could prove efficacious with an acceptable safety profile consistent with other anti-TNFα agents. Intravenous (IV) golimumab has been definitively studied in a Phase 3 study in RA (CNTO148ART3001) that formed the basis of approval for golimumab IV for the treatment of RA. The CNTO148ART3001 study was a randomized, double-blind, placebo-controlled, multicenter, 2-arm study of the efficacy and safety of IV administration of golimumab 2 mg/kg infusions administered over a period of 30±10 minutes at Weeks 0, 4, and q8w thereafter in subjects with active RA despite concurrent MTX therapy. Subjects with active RA despite MTX were randomized to receive either placebo infusions (with MTX) or IV golimumab administered 2 mg/kg at Weeks 0, 4, and q8w (with MTX) through Week 24. Starting at Week 24, all subjects were dosed with IV golimumab though Week 100. It was demonstrated that IV golimumab provided substantial benefits in improving RA signs and symptoms, physical function, and health related quality of life, as well as inhibiting the progression of structural damage.

Golimumab administered intravenously in the treatment of RA (CNTO148ART3001) demonstrated robust efficacy and an acceptable safety profile with a low incidence of infusion reactions. This proposed Phase 3 study is designed to demonstrate the efficacy and safety of IV golimumab in the treatment of subjects with active PsA.

The IV route of administration in subjects with PsA is being evaluated since currently available IV anti-TNFα agents have limitations with respect to immunogenicity and infusion reactions, and have longer infusion times (60 to 120 minutes) compared with the proposed 30±10 minute infusions with IV golimumab.

Patients may also prefer the maintenance dosage schedule of q8w IV golimumab rather than more frequent SC administrations. Therefore, IV golimumab may be an important addition to the currently available treatment options for patients with PSA.

The dosing regimen for this study is 2 mg/kg of golimumab administered via IV infusion over 30±10 minutes at Weeks 0 and 4, then q8w (with or without MTX).

Objectives and Hypothesis
Objectives
Primary Objective

The primary objective of this study is to evaluate the efficacy of IV administration of golimumab 2 mg/kg in subjects with active PsA by assessing the reduction in signs and symptoms of PsA.

Secondary Objectives

The secondary objectives are to assess the following for IV golimumab:
Efficacy related to improving psoriatic skin lesions, physical function, health-related quality of life, and other health outcomes
Inhibition of progression of structural damage
Safety
Pharmacokinetics (PK), pharmacodynamics (PD), and immunogenicity Hypothesis To address the primary objective of the study, the statistical hypothesis (alternative hypothesis) is that golimumab 2 mg/kg is statistically superior to placebo in reducing the signs and symptoms of subjects with active PsA based on the primary efficacy endpoint. The primary endpoint of this study is the proportion of subjects who achieve a 20% improvement from baseline in the American College of Rheumatology criteria (called ACR 20) at Week 14. This endpoint was chosen because it is well-accepted by regulatory authorities and the clinical PsA community.

Study Design and Rationale
Overview of Study Design

This is a Phase 3 multicenter, randomized, double-blind, placebo-controlled study of the efficacy and safety of IV golimumab compared with placebo in subjects with active PsA. Approximately 440 subjects will be randomized at approximately 90 investigational sites. Subjects will be randomly assigned to receive golimumab 2 mg/kg or placebo IV infusions at Weeks 0, 4, 12, and 20. At Week 16, all subjects who qualify for early escape will be allowed one of the following concomitant medication interventions, as selected by the investigator: an increase in their corticosteroid dose (maximum total dose prednisone 10 mg/day, or equivalent), MTX dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit.

At Week 24, all subjects receiving placebo infusions will cross over and begin receiving golimumab IV infusions at Weeks 24, 28 and q8w thereafter through Week 52. Subjects in the golimumab IV treatment group will receive a placebo infusion at Week 24 to maintain the blind and continue to receive golimumab IV infusions at Weeks 28 and q8w thereafter through Week 52. Database locks (DBL) are scheduled for Weeks 24 and 60.

Subjects will be followed for AEs and SAEs at least 8 weeks following the last study treatment administration. The end of study is defined as the time the last subject completes the Week 60 visit.

Figure 18:
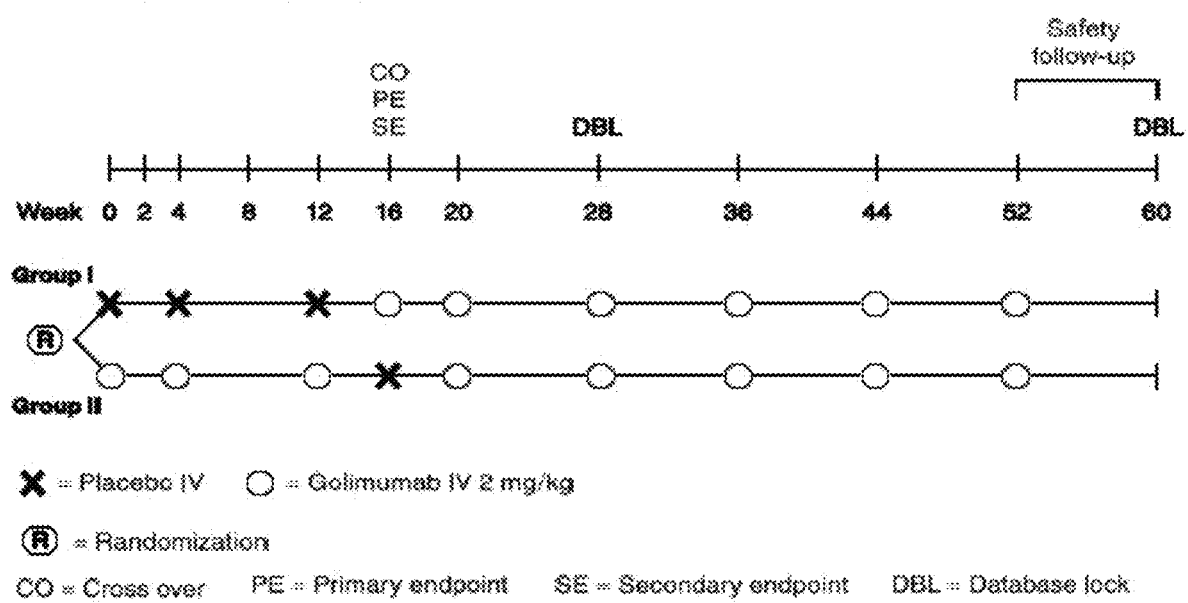
FIG. 18 shows diagram of the study design for trial of Simponi (golimumab), administered intravenously, in subjects with active Psoriatic Arthritis (PsA)

A diagram of the study design is provided in FIG. 18.
Study Design Rationale
Study Population The target study population is biologic-naïve subjects with active PsA for at least 6 months who meet ClASsification criteria for Psoriatic ARthritis (CASPAR)[27] criteria at screening.

Treatment Groups, Dosage, and Dose Administrations Interval

Subjects will be randomized at Week 0 to 1 of 2 treatment groups as follows:
Group 1 (n=220): IV placebo infusions
Group 2 (n=220): IV golimumab 2 mg/kg Subjects will be randomly assigned to receive golimumab 2 mg/kg or placebo IV infusions at Weeks 0, 4, 12, and 20. At Week 16, all subjects who qualify for early escape will be allowed one of the following concomitant medication interventions, as selected by the investigator: an increase in their corticosteroid dose (maximum total dose prednisone 10 mg/day, or equivalent), MTX dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit. At Week 24, all subjects receiving placebo infusions will cross over and begin receiving golimumab IV infusions at Weeks 24, 28 and q8w thereafter through Week 52. Subjects in the golimumab IV treatment group will receive a placebo infusion at Week 24 to maintain the blind and continue to receive golimumab IV infusions at Weeks 28 and q8w thereafter through Week 52.

Study Phases and Duration of Treatment

There will be 4 phases in this study: Screening, double-blind placebo-controlled, active treatment, and safety follow-up. The screening phase of up to 6 weeks will allow for sufficient time to perform screening study evaluations and determine study eligibility. The second phase of the study will be the double-blind, placebo-controlled phase from Week 0 to Week 24. The third phase of the study will be the active treatment phase from Week 24 through Week 52. The fourth phase of the study will be the safety follow-up phase and will be 8 weeks from the last administration of study agent. The safety follow-up allows for monitoring of the subject for a period equivalent to approximately 5 times the half-life of golimumab. Initial treatment assignment for each subject is blinded to sites and subjects throughout the 60 weeks of the trial. This duration will provide adequate time to demonstrate the efficacy and safety of IV golimumab as maintenance therapy for PsA.

The study will end when the last subject completes the last scheduled visit (Week 60 visit).

Study Control, Randomization, and Blinding

Randomization will be used to minimize bias in the assignment of subjects to treatment groups, to increase the likelihood that known and unknown subject attributes (eg, demographic and baseline characteristics) are evenly balanced across treatment groups, and to enhance the validity of statistical comparisons across treatment groups. In addition, the 2 arms of the study will be stratified based on geographic region and baseline MTX use (yes or no).

Individual subjects and investigators will remain blinded for the duration of the study. Blinded treatment will be used to reduce potential bias during data collection and evaluation of clinical endpoints. Two DBLs are planned for the study at Weeks 24 and 60. The first DBL will occur after all subjects complete the Week 24 visit or terminate their participation in the study. The second DBL will occur after all subjects have either completed the Week 60 visit or terminate their participation in the study. The database will be locked at Week 24 and thereafter summary level data will be unblinded to selected Sponsor personnel. Limited Sponsor personnel will be unblinded at this DBL for data analyses and data review. Identification of Sponsor personnel who will have access to the unblinded subject-level data for the Week 24 DBL will be documented prior to unblinding. All site personnel and subjects will remain blinded to the treatment assignments with the exception of the unblinded pharmacist, until the Week 60 DBL has occurred.

Efficacy Evaluations

Efficacy evaluations chosen for this study were established in previous trials of therapeutic biologic agents for the treatment of PsA. Patient reported outcomes (PROs) chosen for this are also consistent with clinically relevant measurements that are accepted in the medical literature for other studies in PsA and applicable US/EU regulatory guidance documents.

Psoriatic arthritis and psoriasis response evaluations include:
- Subject's Assessment of Pain
- Subject's Global Assessment of Disease
- Physician's Global Assessment of Disease
- Joint Assessments (swollen and tender joint counts)
- Disability Index of the Health Assessment Questionnaire (HAQ-DI)
- Psoriasis Area and Severity Index (PASI)
- Radiographs of hands and feet
- 36-item short form health survey (SF-36)
- Dactylitis Assessment
- Enthesitis Assessment
- Bath Ankylosing Spondylitis Disease Activity Index (BASDAI)
- Modified NAPSI
- Dermatology Life Quality Index (DLQI)
- Functional Assessment of Chronic Illness Therapy (FACIT)—Fatigue
- Work Limitations Questionnaire (WLQ)
- Productivity VAS
- EuroQol-5D (EQ-5D) Questionnaire Subject Population Subjects eligible for the study will be men or women 18 years of age or older with a diagnosis of PsA for at least 6 months prior to the first administration of study agent and meet CASPAR criteria at screening. Screening for eligible subjects will be performed within 6 weeks before administration of the study drug. The inclusion and exclusion criteria for enrolling subjects in this study are described in the following 2 subsections. If there is a question about the inclusion or exclusion criteria below, the investigator should consult with the appropriate Sponsor representative before enrolling a subject in the study.

Inclusion Criteria

Each potential subject must satisfy all of the following criteria to be enrolled in the study.

1. Subject must be a man or woman 18 years of age or older.
2. Subject must be medically stable on the basis of physical examination, medical history, vital signs, and 12-lead electrocardiogram (ECG) performed at screening. This determination must be recorded in the subject's source documents and initialed by the investigator.
3. Subject must be medically stable on the basis of clinical laboratory tests performed at screening. If the results of the serum chemistry panel including liver enzymes or hematology are outside the normal reference ranges, the subject may be included only if the investigator judges the abnormalities or deviations from normal to be not clinically significant or to be appropriate and reasonable for the population under study. This determination must be recorded in the subject's source documents and initialed by the investigator. For tests described in inclusion criteria #5b and #18, results MUST be within the eligibility ranges allowed in inclusion criteria #5b and #18.
4. Have had PsA for at least 6 months prior to the first administration of study agent and meet CASPAR criteria at screening.
5. Have a diagnosis of active PsA as defined by:
    a. 5 or more swollen joints and 5 or more tender joints at screening and at baseline
    AND
    b. C-reactive protein (CRP)≥0.6 mg/dL at screening.
6. Have at least 1 of the PsA subsets: DIP joint involvement, polyarticular arthritis with absence of rheumatoid nodules, arthritis mutilans, asymmetric peripheral arthritis, or spondylitis with peripheral arthritis.
7. Have active plaque psoriasis or a documented history of plaque psoriasis.
8. Have active PsA despite current or previous DMARD and/or NSAID therapy. DMARD therapy is defined as taking a DMARD for at least 3 months, or evidence of DMARD intolerance. NSAID therapy is defined as taking an NSAID for at least 4 weeks or evidence of NSAID intolerance.
9. Before randomization, a woman must be either
    Not of childbearing potential: premenarchal; postmenopausal (>45 years of age with amenorrhea for at least 12 months); permanently sterilized (eg, tubal occlusion, hysterectomy, bilateral salpingectomy); or otherwise be incapable of pregnancy.
    Of childbearing potential and practicing a highly effective method of birth control consistent with local regulations regarding the use of birth control methods for subjects participating in clinical studies: eg, established use of oral, injected or implanted hormonal methods of contraception; placement of an intrauterine device (IUD) or intrauterine system (IUS); barrier methods: Condom with spermicidal foam/gel/film/cream/suppository or occlusive cap (diaphragm or cervical/vault caps) with spermicidal foam/gel/film/cream/suppository; male partner sterilization (the vasectomized partner should be the sole partner for that subject); true abstinence (when this is in line with the preferred and usual lifestyle of the subject).
10. A woman of childbearing potential must have a negative serum pregnancy test (β-human chorionic gonadotropin [β-HCG]) at screening and a negative urine pregnancy test on Week 0 before randomization.
11. A woman must agree not to become pregnant or donate eggs (ova, oocytes) for the purposes of assisted reproduction during the study and for 4 months after receiving the last dose of study drug.
12. A man who is sexually active with a woman of childbearing potential and has not had a vasectomy must agree to use a barrier method of birth control eg, either condom with spermicidal foam/gel/film/cream/suppository or partner with occlusive cap (diaphragm or cervical/vault caps) with spermicidal foam/gel/film/cream/suppository during the study and for 4 months after the last dose of study agent. All men must also not donate sperm during the study and for 4 months after receiving the last dose of study agent.
13. Are considered eligible according to the following tuberculosis (TB) screening criteria:
   a. Have no history of latent or active TB prior to screening. An exception is made for subjects who have a history of latent TB and are currently receiving treatment for latent TB, will initiate treatment for latent TB prior to first administration of study agent, or have documentation of having completed appropriate treatment for latent TB within 5 years prior to the first administration of study agent.
   b. Have no signs or symptoms suggestive of active TB upon medical history and/or physical examination.
   c. Have had no recent close contact with a person with active TB or, if there has been such contact, will be referred to a physician specializing in TB to undergo additional evaluation and, if warranted, receive appropriate treatment for latent TB prior to the first administration of study agent.
   d. Within 6 weeks prior to the first administration of study agent, have a negative QuantiFERON®-TB Gold test result, or have a newly identified positive QuantiFERON®-TB Gold test result in which active TB has been ruled out and for which appropriate treatment for latent TB has been initiated prior to the first administration of study agent. Within 6 weeks prior to the first administration of study agent, a negative tuberculin skin test (TST), or a newly identified positive TST in which active TB has been ruled out and for which appropriate treatment for latent TB has been initiated prior to the first administration of study agent, is additionally required if the QuantiFERON®-TB Gold test is not approved/registered in that country or the TST is mandated by local health authorities.
      i. Subjects with persistently indeterminate QuantiFERON®-TB Gold test results may be enrolled without treatment for latent TB, if active TB is ruled out, their chest radiograph shows no abnormality suggestive of TB (active or old, inactive TB), and the subject has no additional risk factors for TB as determined by the investigator.
      ii. The QuantiFERON®-TB Gold test and the TST is/are not required at screening for subjects with a history of latent TB and ongoing treatment for latent TB or documentation of having completed adequate treatment as described above; Subjects with documentation of having completed adequate treatment as described above are not required to initiate additional treatment for latent TB.
   e. Have a chest radiograph (posterior-anterior view) taken within 3 months prior to the first administration of study agent and read by a qualified radiologist, with no evidence of current, active TB or old, inactive TB.
14. If using MTX, subjects should have started treatment at a dose not to exceed 25 mg/week at least 3 months prior to the first administration of study agent and should have no serious toxic side effects attributable to MTX. Methotrexate route of administration and doses should be stable for at least 4 weeks prior to the first administration of study agent. If currently not using MTX, must have not received MTX for at least 4 weeks prior to the first administration of the study agent.
15. If using NSAIDs or other analgesics for PsA, must be on a stable dose for at least 2 weeks prior to the first administration of study agent. If currently not using NSAIDs or other analgesics for PsA, must not have received NSAIDs or other analgesics for PsA for at least 2 weeks prior to the first administration of the study agent.
16. If using oral corticosteroids, the subject must be on a stable dose equivalent to ≤10 mg of prednisone/day for at least 2 weeks prior to the first administration of study agent. If currently not using oral corticosteroids, the subject must not have received oral corticosteroids for at least 2 weeks prior to the first administration of study agent.
17. Must avoid prolonged sun exposure and not use tanning booths or other ultraviolet light sources during study.
18. Have screening laboratory test results within the following parameters:
   a. Hemoglobin ≥8.5 g/dL
   b. White blood cells ≥3.5×10$^3$/μL
   c. Neutrophils ≥1.5×10$^3$/μL
   d. Platelets ≥100×10$^3$/μL
   e. Serum creatinine ≤1.5 mg/dl
   f. AST, ALT, and alkaline phosphatase levels must be within 1.5 times the ULN range for the laboratory conducting the test.
19. Subject must be willing and able to adhere to the prohibitions and restrictions specified in this protocol.
20. Each subject must sign an informed consent form (ICF) indicating that he or she understands the purpose of and procedures required for the study and are willing to participate in the study.
21. Each subject must sign a separate informed consent form if he or she agrees to provide an optional DNA sample for research (where local regulations permit). Refusal to give consent for the optional DNA research sample does not exclude a subject from participation in the study.
22. Are willing to refrain from the use of complementary therapies including ayurvedic medicine, traditional Chinese medication(s) and acupuncture within 2 weeks prior to the first study agent administration and throughout the duration of the study.

Exclusion Criteria

Any potential subject who meets any of the following criteria will be excluded from participating in the study.
1. Have other inflammatory diseases that might confound the evaluations of benefit of golimumab therapy, including but not limited to RA, AS, systemic lupus erythematosus, or Lyme disease.
2. Are pregnant, nursing, or planning a pregnancy or fathering a child while enrolled in the study or within 4 months after receiving the last administration of study agent.
3. Have used any biologic agents that are targeted for reducing TNFα, including but not limited to infliximab, etanercept, adalimumab, golimumab, and certolizumab pegol.
4. Have ever received tocilizumab.
5. Have ever used cytotoxic drugs, including chlorambucil, cyclophosphamide, nitrogen mustard, or other alkylating agents.

6. Have ever received natalizumab, efalizumab, or agents that deplete B or T cells (eg, rituximab, alemtuzumab, or visilizumab).
7. Have ever received alefacept.
8. Have ever received abatacept.
9. Have ever received tofacitinib or any other Janus kinase inhibitors (JAK) inhibitor.
10. Have ever received ustekinumab.
11. Have ever received anti-IL17 therapies (eg, brodalumab, ixekizumab, and secukinumab).
12. Known allergies, hypersensitivity, or intolerance to human immunoglobulins or to golimumab or its excipients.
13. Have received any systemic immunosuppressives or DMARDs other than MTX within 4 weeks prior to first administration of study agent. Medications in these categories include, but are not limited to sulfasalazine (SSZ), hydroxychloroquine (HCQ), azathioprine, cyclosporine, mycophenolate mofetil, gold, and penicillamine.
14. Have received leflunomide within 4 weeks prior to the first administration of study agent (irrespective of undergoing a drug elimination procedure), or have received leflunomide within 3 months prior to the first administration of study agent and have not undergone a drug elimination procedure.
15. Have received any systemic medications/treatments that could affect psoriasis or skin evaluation (including, but not limited to, injectable corticosteroids, retinoids, 1,25 dihydroxy vitamin D3 and analogues, psoralens, sulfasalazine, hydroxyurea, fumaric acid derivatives, or phototherapy) within 4 weeks of the first administration of study agent.
16. Has used topical medications/treatments that could affect psoriasis or skin evaluation (including, but not limited to, corticosteroids, anthralin, calcipotriene, topical vitamin D derivatives, retinoids, tazarotene, methoxsalen, trimethylpsoralens, pimecrolimus, and tacrolimus) within 2 weeks of the first administration of any study agent.
17. Have received epidural, intra-articular, IM, or IV corticosteroids, including adrenocorticotropic hormone during the 4 weeks prior to first administration of study agent.
18. Are currently receiving lithium or have received lithium within 4 weeks of the first administration of the study agent.
19. Have received, or are expected to receive, any live virus or bacterial vaccination within 3 months prior to the first administration of study agent, during the study, or within 3 months after the last administration of study agent.
20. Have a history of, or ongoing, chronic or recurrent infectious disease, including but not limited to, chronic renal infection, chronic chest infection (eg, bronchiectasis), sinusitis, recurrent urinary tract infection (eg, recurrent pyelonephritis), an open, draining, or infected skin wound, or an ulcer.
21. Have a history of an infected joint prosthesis, or have ever received antibiotics for a suspected infection of a joint prosthesis, if that prosthesis has not been removed or replaced.
22. Have had a serious infection (including but not limited to, hepatitis, pneumonia, sepsis, or pyelonephritis), or have been hospitalized for an infection, or have been treated with IV antibiotics for an infection within 2 months prior to first administration of study agent.
23. Have a history of active granulomatous infection, including histoplasmosis, or coccidioidomycosis, prior to screening. Refer to inclusion criteria for information regarding eligibility with a history of latent TB.
24. Have had a Bacille Calmette-Guerin (BCG) vaccination within 12 months of screening.
25. Have a chest radiograph within 3 months prior to the first administration of study agent that shows an abnormality suggestive of a malignancy or current active infection, including TB.
26. Have had a nontuberculous mycobacterial infection or opportunistic infection (eg, cytomegalovirus, pneumocystosis, aspergillosis) within 6 months prior to screening.
27. Have or have had a herpes zoster infection within 2 months of first administration of study agent.
28. Subject has a history of human immunodeficiency virus (HIV) antibody positive, or tests positive for HIV at Screening.
29. Has a hepatitis B infection. Subjects must undergo screening for hepatitis B virus (HBV). At a minimum, this includes testing for HBsAg (HBV surface antigen), anti-HBs (HBV surface antibody), and anti-HBc total (HBV core antibody total).
30. Subjects who are seropositive for antibodies to hepatitis C virus (HCV), unless they have 2 negative HCV RNA test results 6 months apart prior to screening and have a third negative HCV RNA test result at screening.
31. Have current signs or symptoms of severe, progressive, or uncontrolled renal, hepatic, hematological, gastrointestinal, endocrine, pulmonary, cardiac, neurologic, cerebral, or psychiatric disease.
32. Have a history of, or concurrent congestive heart failure (CHF), including medically controlled, asymptomatic CHF.
33. Have a transplanted organ (with exception of a corneal transplant >3 months prior to the first administration of study agent).
34. Have a known history of lymphoproliferative disease, including lymphoma, or signs and symptoms suggestive of possible lymphoproliferative disease, such as lymphadenopathy of unusual size or location, clinically significant splenomegaly, or monoclonal gammopathy of undetermined significance.
35. Have a history of known demyelinating diseases such as multiple sclerosis or optic neuritis.
36. Subject has a history of malignancy within 5 years before screening (exceptions are squamous and basal cell carcinomas of the skin that has been treated with no evidence of recurrence for at least 3 months before the first study agent administration and carcinoma in situ of the cervix that has been surgically cured).
37. Subject has taken any disallowed therapies, Concomitant Therapy before the planned first dose of study drug.
38. Subject has received an investigational drug (including investigational vaccines) within 5 half-lives or 3 months, whichever is longer, or used an invasive investigational medical device within 3 months before the planned first dose of study drug or is currently enrolled in an investigational study.
39. Subject has any condition for which, in the opinion of the investigator, participation would not be in the best interest of the subject (eg, compromise the well-being) or that could prevent, limit, or confound the protocol-specified assessments.

40. Subject has had major surgery, (eg, requiring general anesthesia) within 1 month before screening, or will not have fully recovered from surgery, or has surgery planned during the time the subject is expected to participate in the study or within 1 month after the last dose of study drug administration.
41. Are unable or unwilling to undergo multiple venipunctures because of poor tolerability or lack of easy access to veins.
42. Are known to have had a substance abuse (drug or alcohol) problem within the previous 3 years.
43. Subject is an employee of the investigator or study site, with direct involvement in the proposed study or other studies under the direction of that investigator or study site, as well as family members of the employees or the investigator.

Prohibitions and Restrictions

Potential subjects must be willing and able to adhere to the following prohibitions and restrictions during the course of the study to be eligible for participation:
1. Both heterosexually active women of childbearing potential and men capable of fathering a child must consent to use a highly effective method of contraception and continue to use contraception for the duration of the study and for 4 months after the last administration of study agent.
2. The use of the following drugs is not permitted concomitantly with IV study agent administration:
   Biologic agents targeted at reducing TNFα (including but not limited to infliximab, SC golimumab, certolizumab pegol, etanercept, visaipu, CT-P13 [Remsima®] and adalimumab)
   IL-1ra (anakinra)
   Tocilizumab or any other biologic targeting IL-6 or IL-6 receptor
   Tofacitinib or any other JAK inhibitor
   B-cell depleting agents (eg, rituximab)
   Cytotoxic drugs such as cyclophosphamide, chlorambucil, nitrogen mustard, or
   other alkylating agents
   Abatacept
   Ustekinumab
   Anti-IL-17 agents (eg, brodalumab, secukinumab, and ixekizumab)
   Investigational drugs
3. The use of the following drugs is not permitted:
   Systemic immunosuppressives or DMARDs (other than MTX) including SSZ, HCQ, azathioprine, oral cyclosporine A, tacrolimus, mycophenolate mofetil, leflunomide, oral or parenteral gold. The only exception is the use of SSZ, HCQ, or leflunomide for subjects who qualify for early escape at Week 16.
4. Must agree not to receive a live virus or live bacterial vaccination during the study. Subjects must also agree not to receive a live vaccine for 3 months after receiving the last administration of study agent. Must not have had a Bacille Calmette-Guérin (BCG) vaccination within 12 months of screening.
5. Must agree not to receive an investigational medical device or an investigational drug other than study agent for this study.
6. Subjects treated with NSAIDs, including aspirin and selective cyclooxygenase (COX)-2 inhibitors, and other analgesics should receive the usual marketed doses approved in the country in which the study is being conducted. Prescriptions of NSAIDs and other analgesics should not be adjusted for at least 2 weeks prior to the first administration of the study drug, and through Week 24, and may be changed only if the subject develops unacceptable side effects. After Week 24 through Week 52, a one-time dose decrease is allowed; otherwise, prescriptions of NSAIDs and other analgesics may be changed only if the subject develops unacceptable side effects. At Week 16, subjects who qualify for early escape may have a one-time initiation of an NSAID or an increase in their NSAID dose.
   The use of topical analgesics including capsaicin and diclofenac is allowed.
7. Subjects treated with oral corticosteroids should receive a stable dose equivalent to ≤10 mg prednisone per day for at least 2 weeks prior to their first administration of the study agent and continue to receive this dose through Week 24. After Week 24 and through Week 52, a one-time dose decrease in oral corticosteroids is allowed; otherwise the dose and type of oral corticosteroid may be changed at the discretion of the investigator only if the subject develops unacceptable side effects. At Week 16, subjects who qualify for early escape may have a one-time initiation or increase in their oral corticosteroid dose (maximum total dose of prednisone 10 mg/day or equivalent).
   Epidural, IM or IV administration of corticosteroids is not allowed within 4 weeks before the first administration of study agent and is not allowed for the treatment of PsA throughout the study. Every attempt should be made to avoid the use of epidural, IM, and IV corticosteroids during the study for indications other than PsA. Long-term (>2 weeks) oral or IV corticosteroids use for indications other than PsA are not allowed throughout the study. Short-term (≤2 weeks) oral, IV, IM, or epidural corticosteroid used for indications other than PsA should be limited to situations where, in the opinion of the treating physician, there are no adequate alternatives.
   Intra-articular steroids should not be administered within 4 weeks prior to the first administration of study agent. Attempts should be made to avoid intra-articular corticosteroid injections especially during the first 24 weeks of the study. However if necessary, subjects may receive up to 2 intra-articular, tendon sheath, or bursal corticosteroid injections in no more than 2 affected sites during the 60 weeks of the study.
8. The use of complementary therapies that may affect PsA disease activity or assessments, including but not limited to traditional medicine (eg, Chinese, acupuncture, ayurvedic medicine) is prohibited through Week 60.

Treatment Allocation and Blinding

Eligible subjects will be randomly assigned using an interactive web response system (IWRS) to receive a fixed dose of golimumab 2 mg/kg or placebo at Week 0 in a blinded fashion. Subject allocation to a treatment group will be done using a stratified block randomization method in a 1:1 ratio to 1 of 2 treatment groups. Stratification factors are geographic region and baseline MTX use (yes or no). This will ensure relative treatment balance for the number of subjects within each geographic region, and with baseline MTX use.

Subjects assigned to golimumab will receive 2 mg/kg through Week 52. At Week 16, all subjects who qualify for early escape will be allowed one of the following concomitant medication interventions, as selected by the investigator: an increase in their corticosteroid dose (maximum total dose prednisone 10 mg/day, or equivalent), MTX dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit.

Subjects assigned to placebo will be crossed over to golimumab 2 mg/kg at Week 24, and will receive golimumab 2 mg/kg at Weeks 24, 28 and q8w through Week 52. Subjects in the golimumab IV treatment group will continue to receive golimumab IV infusions at the same dose. In addition, subjects in the golimumab IV treatment group will receive IV placebo at Week 24 to maintain the blind. Subjects and investigational study sites will remain blinded to initial assigned treatment groups throughout the study.

Under normal circumstances, the blind should not be broken for individual subjects until the 60-Week DBL. Otherwise, the blind should be broken only if specific emergency treatment/course of action would be dictated by knowing the treatment status of the subject. In the event of an emergency, the investigator may determine the identity of the treatment from IWRS. It is recommended that the investigator contact the Sponsor or its designee if possible to discuss the particular situation. Telephone contact with the Sponsor or its designee will be available 24 hours per day, 7 days per week. In the event the blind is broken, the Sponsor must be informed as soon as possible. The date and reason for the unblinding must be documented by site personnel in the eCRF, and the source document. The investigator is also advised not to reveal the study treatment assignment to the study site or Sponsor personnel.

Subjects who have had their treatment assignment unblinded are expected to continue to return for scheduled evaluations. Further study agent administrations should be discussed with the study responsible physician. At the Week 24 DBL, the data will be unblinded for analysis to limited Sponsor personnel while subjects are still participating in the study. Identification of Sponsor personnel who will have access to the unblinded subject-level data will be documented prior to unblinding. Investigative study sites and subjects will remain blinded to initial treatment assignment until after the Week 60 database is locked.

Data that may potentially unblind the treatment assignment (i.e., study agent serum concentrations, antibodies to study agent, treatment allocation, and study agent preparation/accountability data) will be handled with special care so that, prior to unblinding, such data will only be available to data management staff for purposes of data cleaning and, if applicable, clinical pharmacology representatives for the purposes of performing pharmacokinetic and antibodies to golimumab analyses and quality assurance representatives for the purposes of conducting independent drug audits.

A given subject's treatment assignment may be unblinded to the Sponsor, IRB/EC, and site personnel to fulfill regulatory reporting requirements.

Dosage and Administration
Dosing Regimen and Blinding

Before the first infusion of study agent, subjects will be randomly assigned in a 1:1 ratio to 1 of the following 2 treatment groups:

Group I (n=220): Subjects will receive IV placebo infusions at Weeks 0, 4, 12, and 20. Subjects will cross over to IV golimumab 2 mg/kg at Week 24, and receive administrations at Weeks 24, 28, and q8w thereafter.

Group II (n=220): Subjects will receive IV golimumab 2 mg/kg at Weeks 0, 4, and q8w thereafter. Subjects will receive an IV placebo infusion at Week 24 to maintain the blind.

Note: All infusions will be completed over 30±10 minutes.

Early Escape

At Week 16, all subjects in Groups I and II with <5% improvement from baseline in both tender and swollen joint counts will enter early escape in a double-blinded fashion. At Week 16, all subjects who qualify for early escape will be allowed one of the following concomitant medication interventions, as selected by the investigator: an increase in their corticosteroid dose (maximum total dose prednisone 10 mg/day, or equivalent), MTX dose (maximum total dose 25 mg/week), or NSAID dose, or an initiation of NSAID, corticosteroids (maximum dose prednisone 10 mg/day or equivalent), MTX (maximum dose 25 mg/week), SSZ (maximum dose 3 g/day), HCQ (maximum dose 400 mg/day), or leflunomide (maximum dose 20 mg/day). Titration to a stable dose of those medications should be completed for subjects qualifying for early escape by the Week 24 visit.

Study Agent Administration and Timing

All postbaseline visits may occur at the indicated week±7 days throughout the study, with the exception of the Week 4, Week 12, Week 14, Week 16, and Week 24 visits, which may occur at the indicated week±4 days. If the recommended acceptable window cannot be observed, the Sponsor must be contacted before scheduling a visit.

Prestudy and Concomitant Therapy

Every effort should be made to keep subjects' concomitant medications stable through Week 24 or as specified in the following sections. The concomitant medication dose may be reduced or the medication temporarily discontinued because of abnormal laboratory values, side effects, concurrent illness, or the performance of a surgical procedure, but the change and reason for the change should be clearly documented in the subject's medical record.

Subjects should not initiate any new treatment for PsA during the study, except at Week 16 for subjects who qualify for early escape.

Concomitant medication review will occur at study visits identified in the Time and Events Schedule.

Methotrexate

Subjects are permitted to enter the study on stable doses of MTX.

If subjects are using MTX, treatment should have started at least 3 months prior to the first administration of study agent. MTX routes of administration and doses ≤25 mg/week should be stable for at least 4 weeks prior to the first administration of the study agent. It is recommended that all subjects taking MTX in this study receive at least 5 mg oral folate or 5 mg folinic acid weekly.

Subjects not on treatment with MTX must have discontinued the treatment for at least 4 weeks prior to the first administration of study agent, and must not receive MTX through Week 60. SIMPONI IV (golimumab) Clinical Protocol CNTO148PSA3001 Amendment 2 45 Approved. 29 Jun. 2016 An exception is made for subjects who qualify for early escape at Week 16. At Week 16, subjects who qualify for early escape may initiate or have a one-time increase in their MTX dose (maximum total dose 25 mg/week).

For subjects who initiate MTX, titration to a stable dose should be completed by the Week 24 visit. For subjects receiving MTX, every effort should be made to maintain stable doses and route of administration of this medication through Week 60 of the study. However, the dose of MTX may be decreased in the event of toxicity. Guidelines for dose adjustment in the event of MTX toxicity are included in the Trial Center File.

Corticosteroids

Subjects treated with oral corticosteroids for PsA should receive a stable dose equivalent to ≤10 mg prednisone per day for at least 2 weeks prior to first administration of study agent and continue to receive this dose through Week 60. Subjects not treated with oral corticosteroids at baseline must have discontinued oral corticosteroids at least 2 weeks prior to the first administration of study agent, and they must not receive oral corticosteroids for PsA through Week 60.

An exception is made for subjects who qualify for early escape at Week 16. At Week 16, subjects who qualify for early escape may initiate or have a one-time increase in their oral corticosteroid dose (maximum total dose of prednisone 10 mg/day or equivalent).

After Week 24 and through Week 60, a one-time dose decrease in oral corticosteroids is allowed; otherwise the dose and type of oral corticosteroid may be changed at the discretion of the investigator only if the subject develops unacceptable side effects.

Intravenous, intramuscular, or epidural administration of corticosteroids for the treatment of PsA is not allowed throughout the study.

Long-term (>2 weeks) oral or IV corticosteroids use for indications other than PsA are not allowed throughout the study. Short-term (≤2 weeks) oral, IV, IM, or epidural corticosteroid used for indications other than PsA should be limited to situations where, in the opinion of the treating physician, there are no adequate alternatives. Inhaled, otic, ophthalmic, intranasal, and other routes of mucosal delivery of corticosteroids are allowed throughout the course of the study.

Attempts should be made to avoid intra-articular corticosteroid injections, especially during the first 24 weeks of the study. However if necessary, subjects may receive up to 2 intra-articular, tendon sheath, or bursal corticosteroid injections in no more than 2 affected sites during the 60 weeks of the study. In the case of severe tenderness or swelling in a single joint, it is suggested that the subject be evaluated for infection prior to receiving an intra-articular corticosteroid injection.

Nonsteroidal Anti-Inflammatory Drugs and Other Analgesics

The use of stable doses of NSAIDs and other analgesics is allowed.

Subjects treated with NSAIDs, including aspirin and selective cyclooxygenase-2 inhibitors, and other analgesics should receive the usual marketed doses approved in the country in which the study is being conducted, and should have been on a stable dose at least 2 weeks prior to the first administration of the study agent. Through Week 24, the dose and type of NSAIDs and other analgesics may be changed only if the subject develops unacceptable side effects.

An exception is made for subjects who qualify for early escape at Week 16. At Week 16, subjects who qualify for early escape may initiate or have a one-time increase in their NSAID dose. For subjects who initiate NSAID, titration to a stable dose should be completed by the Week 24 visit.

After Week 24 and through Week 60, a one-time dose decrease is allowed; otherwise, prescriptions of NSAIDs and other analgesics may be changed only if the subject develops unacceptable side effects.

The use of topical analgesics including capsaicin and diclofenac is allowed.

In this trial, aspirin is considered an NSAID, except for low-dose aspirin prescribed for cardiovascular or cerebrovascular disease.

Disease-Modifying Antirheumatic Drugs/Systemic Immunosuppressive Drugs

Disease-modifying antirheumatic drugs/systemic immunosuppressive agents, with the exception of MTX, must be discontinued at least 4 weeks prior to the first administration of study agent and are prohibited through Week 60. These DMARDs include, but are not limited to SSZ, HCQ, gold preparations, penicillamine, and leflunomide. If a subject received leflunomide within 3 months prior to the first administration of study agent, the subject must have undergone a drug elimination procedure.

An exception is made for subjects who qualify for early escape. At Week 16, subjects who qualify for early escape may have a one-time initiation of SSZ (maximum dose 3 g/day), HCQ (maximum dose 400 mg/day), or leflunomide (maximum dose 20 mg/day For subjects who initiate SSQ, HCQ, or leflunomide, titration to a stable dose should be completed by the Week 24 visit.

Prohibited systemic immunosuppressive drugs through Week 60 include, but are not limited to, cyclosporine, tacrolimus, mycophenolate mofetil, and azathioprine. Systemic SIMPONI IV (golimumab) Clinical Protocol CNTO148PSA3001 Amendment 2 47 Approved. 29 Jun. 2016 immunosuppressives do not refer to corticosteroids.

Biologic Agents, Cytotoxic Drugs, or Investigational Agents

The use of biologic agents (eg, SC golimumab, anakinra, etanercept, adalimumab, infliximab, alefacept, efalizumab, rituximab, natalizumab), cytotoxic agents (eg, chlorambucil, cyclophosphamide, nitrogen mustard, other alkylating agents), or investigational drugs is not allowed during the 60 weeks of the study. If any of these medications are used, the subject will be discontinued from further study agent infusions.

Complementary Therapies

The use of complementary therapies including ayurvedic medicine, traditional Chinese medications or non-medicinal therapy such as acupuncture is not allowed during the 60 weeks of the study.

Topical Therapy and Ultraviolet B Light

Concurrent use of topical medications/treatments for psoriasis (eg, corticosteroids keratolytics [with the exception of salicylic acid shampoos, which are allowed throughout the study], coal tar [with the exception of coal tar shampoos, which are allowed throughout the study], anthralin, vitamin D3 analogues, or topical tacrolimus, and retinoids), are not permitted through Week 24.

Subjects should not use salicylic acid and tar containing shampoos during the morning prior to a study visit. Non-medicated shampoos may be used on the day of a visit.

After the Week 24 infusion, topical therapies including intralesional corticosteroids may be used with the exception of high and ultra-high potency corticosteroids (Class I and II). UVB or tanning beds are not permitted through Week 60. Subjects should be encouraged to avoid prolonged sun exposure during the study.

Systemic Therapy for Psoriasis

Concurrent use of systemic therapy for psoriasis (eg, psoralen with ultraviolet light A [PUVA], systemic retinoids, cyclosporine or tacrolimus) is not permitted through Week 60. Use of systemic antipsoriatic therapies must be discontinued at least 4 weeks prior to the first administration of study agent.

Study Evaluations
Study Procedures
Overview

For women of childbearing potential only, additional serum or urine pregnancy tests may be performed, as determined necessary by the investigator or required by local regulation, to establish the absence of pregnancy at any time during the subject's participation in the study. Also additional TB tests may be performed as determined necessary by the investigator or required by local regulation.

All visit-specific PRO assessments should be conducted before any tests, procedures, or other consultations for that visit to prevent influencing subjects' perceptions. For additional details, refer to the PRO user manual.

Every effort should be made to perform all other assessments in the order specified in the Time and Events Schedule unless logistically not feasible, and if possible, the same individual(s) should perform the assessments at each visit.

Serum for the analysis of pharmacodynamic markers and whole blood (for gene expression analysis) will be collected from all subjects. At Weeks 0 and 24, a whole blood sample for DNA analysis will be collected only from subjects who have consented to participate in the optional pharmacogenomics (DNA) component of the study. Blood samples for DNA analyses will only be collected if permitted by local regulations. Refer to the Laboratory Reference Manual for the Pharmacogenomics Sample Collection and Shipment Procedures for details on collecting and handling blood samples for pharmacogenomics research. In the event of DNA extraction failure, a replacement pharmacogenomics blood sample may be requested from the subject. Signed informed consent will be required to obtain a replacement sample.

The total blood volume to be collected in this study from each subject will be approximately 253 mL for the main study and 20 mL for optional DNA testing.

Repeat or unscheduled samples may be taken for safety reasons or for technical issues with the samples.

Screening Phase

After written informed consent has been obtained and within a period of 6 weeks before randomization, all screening evaluations will be performed. The screening visit may be divided into more than 1 visit. For example, after obtaining informed consent, the investigator will complete all laboratory tests at the first visit. The subject will then return for the remainder of the screening procedures only if the subject is eligible for the study as determined by the central laboratory test results. Subjects who meet all of the inclusion and none of the exclusion criteria will be enrolled in the study. Every effort should be made to adhere to the study Time and Events Schedule for each subject. Subjects must provide a separate written pharmacogenomics informed consent to participate in the optional pharmacogenomics research component of the study.

Women of childbearing potential must have a negative serum pregnancy test at screening and a negative urine pregnancy test before randomization. Women of childbearing potential and men capable of fathering a child must consent to use a highly effective method of contraception and continue to use contraception for the duration of the study and 4 months after. The method(s) of contraception used by each subject must be documented.

A 12-lead ECG will be performed locally at screening to ensure that should the subject require an ECG during the study for any reason, an ECG prior to first study agent administration is available for comparison to detect changes.

A chest radiograph (posterior-anterior [PA]) will be performed at screening to ensure that the subject does not have any abnormality suggestive of a malignancy or current active infection, including TB. Chest x-rays taken up to 3 months prior to the first administration of study agent may be used.

Subjects must undergo testing for TB and their medical history assessment must include specific questions about a history of TB or known occupational or other personal exposure to individuals with active TB. The subject should be asked about past testing for TB, including chest radiograph results and responses to tuberculin skin or other TB testing.

Subjects with a negative QuantiFERON®-TB Gold test result (and a negative TST result in countries in which the QuantiFERON®-TB Gold test is not approved/registered or the TST is mandated by local health authorities) are eligible to continue with prerandomization procedures. Subjects with a newly identified positive QuantiFERON®-TB Gold test (or TST) result must undergo an evaluation to rule out active TB and initiate appropriate treatment for latent TB prior to the administration of the first dose of study agent. An exception is made for subjects currently receiving treatment for latent TB with no evidence of active TB, or who have a history of latent TB and documentation of having completed appropriate treatment for latent TB within 5 years prior to the first administration of study agent. These subjects do not need to be retested with the QuantiFERON®-TB Gold test (or TST) during screening. Appropriate treatment for latent TB is defined according to local country guidelines for immunocompromised patients. If no local country guidelines for immunocompromised patients exist, US guidelines must be followed or the subject must be excluded from the study. It is the responsibility of the investigator to verify the adequacy of previous anti-TB treatment and provide appropriate documentation.

A subject whose first QuantiFERON®-TB Gold test result is indeterminate should have the test repeated. In the event that the second QuantiFERON®-TB Gold test result is also indeterminate, the subject may be enrolled without treatment for latent TB, if active TB is ruled out, their chest radiograph shows no abnormality suggestive of TB (active or old, inactive TB), and the subject has no additional risk factors for TB as determined by the investigator. This determination must be promptly reported to the Sponsor's medical monitor and recorded in the subject's source documents and initialed by the investigator.

Retesting

The re-testing of abnormal screening laboratory blood tests and CRP levels that lead to exclusion is allowed only once using an unscheduled visit during the screening period (to reassess eligibility).

Treatment Phase

Treatment phase includes the placebo-controlled and active treatment phases. At Week 0, eligible subjects will be randomly assigned to receive 1 of 2 treatments: golimumab IV 2 mg/kg, or placebo IV.

Efficacy
Psoriatic Arthritis Response Evaluations
Joint Assessments

Each of 68 joints will be evaluated for tenderness, and each of 66 joints will be evaluated for swelling (hips are excluded for swelling). All joints will be examined at visits as indicated in the Time and Events Schedules.

An independent joint assessor (IJA) with adequate training and experience in performing joint assessments will be designated at each study site to perform all joint assessments, as well as dactylitis and enthesitis assessments. It is strongly recommended that the same IJA who performs the baseline joint assessments for a subject should also perform the joint assessments for that subject at every subsequent visit through Week 52.

The Sponsor will provide training for each site's designated IJA prior to the screening of the first subject at each site. A back-up IJA must complete training before performing a joint assessment for a subject's study visit.

If an IJA was trained by the Sponsor in a previous clinical study within the last 3 years and there is adequate documentation of this training (certification), that training will be considered adequate for this study; however, repeat training prior to start of the trial is encouraged. Training documentation of each IJA should be maintained at the study site.

All IJA performing the joint evaluation at a site must be listed on the Delegation Log at the study site and should be documented in the source documents at each visit.

After Week 24, the joint assessor no longer needs to be independent. However it is recommended that the joint assessor should not be changed during the study.

Nonevaluable Joints

Joints should only be designated as "non-evaluable" by the IJA if it is physically impossible to assess the joint (i.e., joint inaccessible due to a cast, joint not present due to an amputation, joint deformed so as to make it impossible to assess). In all other cases, the IJA should assess each joint for tenderness and swelling (hips are excluded for swelling). This should be completed regardless of any visual indications of prior surgeries (eg, scars) or knowledge they may have of a subject's prior joint procedures/injections (eg, if the subject was the IJA's patient prior to study participation).

American College of Rheumatology Responses

American College of Rheumatology responses are presented as the numerical measurement of improvement in multiple disease assessment criteria. For example, an ACR 20 response[10] is defined as:

1. ≥20% improvement from baseline in both swollen joint count (66 joints) and tender joint count (68 joints), AND
2. ≥20% improvement from baseline in 3 of the following 5 assessments:
   Patient's assessment of pain (VAS)
   Patient's Global Assessment of Disease Activity (VAS)
   Physician's Global Assessment of Disease Activity (VAS)
   Patient's assessment of physical function as measured by HAQ-DI
   CRP ACR 50, ACR 70, and ACR 90 are similarly defined except improvement threshold from baseline is 50%, 70%, and 90%, respectively.

Dactylitis Assessment

Presence and severity of dactylitis will be assessed in both hands and feet using a scoring system from 0 to 3 (0—no dactylitis, 1—mild dactylitis, 2—moderate dactylitis, and 3—severe dactylitis).[15,16]

The IJA will perform all dactylitis assessments. The Sponsor will provide dactylitis assessment training. Documentation of this training will be maintained in the study site's training files.

Enthesitis Assessment

Enthesitis will be assessed using the Leeds Enthesitis Index (LEI). 18 The LEI was developed to assess enthesitis in subjects with PsA, and evaluates the presence or absence of pain by applying local pressure to the following entheses:

Lateral elbow epicondyle, left and right
Medial femoral condyle, left and right
Achilles tendon insertion, left and right The IJA will perform all enthesitis assessments. The Sponsor will provide enthesitis assessment training. Documentation of this training will be maintained in the study site's training files.

Imaging Evaluations

The total modified van der Heijde-Sharp (vdH-S) score is an original vdH-S score,[28] modified for the purpose of PsA radiological damage assessment, by addition of DIP joints of the hands and assessment of pencil in cup and gross osteolysis deformities. The joint erosion score is a summary of erosion severity in 40 joints of the hands and 12 joints in the feet. Each hand joint is scored, according to surface area involved, from 0 indicating no erosion through 5 indicating extensive loss of bone from more than one half of the articulating bone. Because each side of the foot joint is graded on this scale, the maximum erosion score for a foot joint is 10. Thus, the maximal erosion score is 320. The joint space narrowing (JSN) score summarizes the severity of JSN in 40 joints in the hands and 12 joints of the feet. Assessment of JSN is scored from 0 through 4, with 0 indicating no JSN and with 4 indicating complete loss of joint space, bony ankylosis, or complete luxation. Thus, the maximal JSN score is 208 and 528 is the worst possible total modified vdH-S score for PsA.

Single radiographs of the hands (posteroanterior) and feet (anteroposterior) will be performed at visits, to minimize unnecessary x-rays it is recommended that subjects have the baseline radiographs of hands and feet taken after the inclusion and exclusion criteria have been checked and the subject appears eligible to enter the study. Baseline radiographs must be taken prior to randomization. It is suggested that these radiographs be performed approximately 2 weeks prior to randomization to allow time to address any potential issues with radiograph quality. Subjects who qualify for EE will have radiographs collected at Week 16 and at Week 24. Subjects who do not qualify for EE will have radiographs taken at Week 24. All subjects will have radiographs taken at Week 52. All radiographs will be taken ±2 weeks of their scheduled visit.

For subjects who permanently discontinue study agent prior to Week 52, radiographs of hands and feet should be performed at the time of discontinuation of study agent. These radiographs of hands and feet do not need to be performed if another set of radiographs was obtained within the past 6 weeks.

The radiographs will be evaluated by central independent readers. There will be 2 reading campaigns: Read Campaign I will include Week 0, Week 16 (for subjects who entered early escape) and Week 24 (and/or study agent discontinuation visit prior to Week 24); Read Campaign 2 will include Week 0, Week 24, and Week 52, data or study agent discontinuation visit after Week 24 but prior to Week 52.

Detailed information on the acquisition of radiographs will be provided in an Imaging Manual.

Disability Index of the Health Assessment Questionnaire

The functional status of the subject will be assessed by the HAQ-DI.[13] This 20-question instrument assesses the degree of difficulty a person has in accomplishing tasks in 8 functional areas (dressing, arising, eating, walking, hygiene, reaching, gripping, and activities of daily living). Responses in each functional area are scored from 0, indicating no difficulty, to 3, indicating inability to perform a task in that area (i.e., lower scores are indicative of better functioning). Properties of the assessment have been evaluated and its validity in PsA has been determined.[19] It has also been shown to be responsive to changes in a subject's disease.[22] In PsA, a decrease in score of 0.30 has been determined to indicate a meaningful improvement.[21]

Minimal Disease Activity

The PsA minimal disease activity (MDA) criteria are a composite of 7 outcome measures used in PsA. Subjects are classified as achieving MDA if they fulfilled 5 of 7 outcome measures: tender joint count ≤1; swollen joint count ≤1; psoriasis activity and severity index ≤1 or body surface area ≤3; patient pain visual analog scale (VAS) score of ≤15; patient global disease activity VAS score of ≤20; Health Assessment Questionnaire (HAQ) score ≤0.5; and tender entheseal points ≤1.[6]

36-Item Short-Form Health Survey

The Medical Outcome Study health measure SF-36 questionnaire was developed as part of the Rand Health Insurance Experiment and consists of 8 multi-item scales:

limitations in physical functioning due to health problems;
limitations in usual role activities due to physical health problems;
bodily pain;
general mental health (psychological distress and well-being);
limitations in usual role activities due to personal or emotional problems;
limitations in social functioning due to physical or mental health problems;
vitality (energy and fatigue);
general health perception.

These scales are scored from 0 to 100 with higher scores indicating better health. Another algorithm yields 2 summary scores, the Physical Component Summary (PCS) and the Mental Component Summary (MCS). These summary scores are also scaled with higher scores indicating better health but are scored using a norm-based system where linear transformations are performed to transform scores to a mean of 50 and standard deviations of 10, based upon general US population norms.[34] The concepts measured by the SF-36 are not specific to any age, disease, or treatment group, allowing comparison of relative burden of different diseases and the relative benefit of different treatments. 3.3

Psoriasis Response Evaluations

Psoriasis Area and Severity Index

The PASI is a system used for assessing and grading the severity of psoriatic lesions and their response to therapy.[12] The PASI produces a numeric score that can range from 0 to 72. A PASI 50 response is defined as ≥50% improvement in PASI score from baseline; PASI 75 and PASI 90 are similarly defined.

Every effort should be made to ensure that the physician or designee who performed the PASI evaluations for a subject at baseline should also perform the PASI for that subject at all subsequent visits. The Sponsor will provide PASI training. Documentation of this training will be maintained in the site's training files.

Endpoints

Primary Endpoint

The primary endpoint of this study is the proportion of subjects who achieve an ACR 20 response at Week 14.

The study will be considered positive if the proportion of subjects with ACR 20 at Week 14 is demonstrated to be statistically significantly greater in the golimumab group compared with the placebo group.

Major Secondary Endpoints

The following major secondary endpoints are listed in order of importance as specified below:

1. The change from baseline in the HAQ-DI score at Week 14.
2. The proportion of subjects who achieve an ACR 50 response at Week 14.
3. The proportion of subjects (with baseline ≥3% BSA psoriatic involvement) who achieve a PASI 75 response at Week 14.
4. The change from baseline in total modified vdH-S score at Week 24.

Other Secondary Endpoints

Controlled Secondary Endpoints (with Control of Type I Error Rate for Multiplicity).

The following controlled secondary endpoints will be analyzed in addition to the primary and major secondary endpoints and are listed in the order of importance as specified below:

1. The change from baseline in enthesitis score at Week 14 in subjects with enthesitis at baseline.
2. The change from baseline in dactylitis scores at Week 14 in subjects with dactylitis at baseline.
3. The change from baseline in SF-36 PCS at Week 14.
4. The proportion of subjects who achieve an ACR 50 response at Week 24.
5. The proportion of subjects who achieve an ACR 70 response at Week 14.
6. The change from baseline in SF-36 MCS at Week 14.

To control for multiplicity, the above endpoints will be tested sequentially according to the above order only when the primary and all the major secondary endpoints achieved statistically significance. Otherwise, nominal p-values will be provided.

Other Secondary Endpoints Include

In addition to the primary, major secondary, and controlled secondary endpoints, the following endpoints will be evaluated:

Endpoints Related to Reduction of Signs and Symptoms and Physical Function

1. The proportion of subjects who achieve an ACR 20 response at Week 2.
2. The proportion of subjects who achieve an ACR 20, ACR 50, ACR 70, and ACR 90 responses over time.
3. The change from baseline in the components of the ACR response overtime.
4. The proportions of subjects who achieve a ≥20%, ≥50%, ≥70%, and ≥90% improvement in each component of the ACR response over time
5. The change from baseline in HAQ-DI score over time.
6. The proportion of subjects who achieve a clinically meaningful improvement for PsA subjects (a ≥0.3 improvement) in HAQ-DI score over time.
7. The change from baseline in the dactylitis score in subjects with dactylitis at baseline and the proportion of subjects with digits with dactylitis over time.
8. The change from baseline in the enthesitis score in subjects with enthesitis at baseline and the proportion of subjects with enthesitis over time.
9. The proportion of subjects who achieve an ACR 20 response at Week 52 in subjects who achieved an ACR response at Week 24. Similar endpoints for ACR 50, 70 and 90 responders will also be evaluations.
10. The proportion of subjects who achieve HAQ-DI response (subjects achieving a ≥0.3 improvement in HAQ-DI score) at Week 52 in subjects who achieved HAQ-DI response at Week 24.

11. The proportion of subjects who achieve MDA over time.

Endpoints Related to Skin Disease Include
1. For subjects with ≥3% BSA psoriasis skin involvement at baseline, the proportion of subjects who achieve ≥50%, ≥75%, ≥90%, and 100% improvement in PASI from baseline over time overall, and by baseline MTX use.
2. For subjects with ≥3% BSA psoriasis skin involvement at baseline, the improvement from baseline in PASI over time.
3. For subjects with ≥3% BSA psoriasis skin involvement at baseline, the proportion of subjects who achieve both PASI 75 and ACR 20 responses over time.
4. For subjects with ≥3% BSA psoriasis skin involvement at baseline, the proportion of subjects who achieve both PASI 50 and improvement in DLQI≥5 over time.
5. For subjects with ≥3% BSA psoriasis skin involvement at baseline, the proportion of subjects who achieve both PASI 75 and modified PsARC response over time.

Endpoints Related to Joint Structural Damage Include
For structural damage endpoints, there will be 2 Read Campaigns: Read Campaign I will contribute to analyses at Week 24 and Read Campaign 2 will contribute to analyses at Week 52.
1. The proportion of subjects who have a change from baseline in total modified vdH-S score ≤0 at Week 24.
2. The change from baseline in total modified vdH-S score at Week 24 and Week 52.
3. The change in total modified vdH-S score from Week 0 to Week 24, from Week 24 to Week 52. The change from baseline in total modified vdH-S score by region (hands, feet) at Week 24 and Week 52.
4. The change from baseline in modified vdH-S scores by type of damage (erosion and JSN) at Week 24 and Week 52.
5. Number of subjects with maintenance of joint damage-free state (total modified vdH-S score of 0, erosion score of 0, or JSN score of 0) at baseline, Week 24 and Week 52.
6. Number of subjects with change from baseline in the total modified vdH-S score ≤0 or ≤0.5 at Week 24 and Week 52.

Endpoints Related to Health Related Quality of Life Include
1. The change from baseline in the PCS score and the MCS score of the SF-36 over time.
2. The change from baseline in SF-36 scales over time.
3. The proportion of subjects who achieve an SF-36 PCS score improvement of ≥5 over time.
4. The proportion of subjects who achieve an SF-36 MCS score improvement of ≥5 over time.

Subject Completion/Withdrawal
Completion
A subject will be considered to have completed the study if he or she has completed assessments at Week 60 of the study. Subjects who prematurely discontinue study treatment for any reason will not be considered to have completed the study.

Discontinuation of Study Treatment
If a subject's study treatment must be discontinued before the end of the treatment regimen, this will not result in automatic withdrawal of the subject from the study.
If a subject discontinues study agent administrations at or before Week 52, he/she must return for specific efficacy and final safety visits.
Study agent administrations must be permanently discontinued if any of the following occur:

Pregnancy or pregnancy planned within the study period or within 4 months after the last study agent administration.
Reaction resulting in bronchospasm with wheezing and/or dyspnea requiring ventilator support, or symptomatic hypotension that occurs following a study agent administration.
Reaction resulting in myalgia and/or arthralgia with fever and/or rash (suggestive of serum sickness and not representative of signs and symptoms of other recognized clinical syndromes) occurring 1 to 14 days after an infusion of study agent. These may be accompanied by other events including pruritus, facial, hand, or lip edema, dysphagia, urticaria, sore throat, and/or headache.
Opportunistic infection.
Malignancy, excluding nonmelanoma skin cancer.
CHF.
Demyelinating disease.
Subject is deemed ineligible according to the following TB screening criteria:
 A diagnosis of active TB is made.
 A subject receiving treatment for latent TB discontinues this treatment prematurely or is noncompliant with the therapy.
 A subject has symptoms suggestive of active TB based on follow-up assessment questions and/or physical examination, or has had recent close contact with a person with active TB, and cannot or will not continue to undergo additional evaluation.
 A subject undergoing continued evaluation has a chest radiograph with evidence of current active TB and/or a positive QuantiFERON®-TB Gold test result (and/or a positive TST result in countries in which the QuantiFERON®-TB Gold test is not approved/registered or the TST is mandated by local health authorities), unless active TB can be ruled out and appropriate treatment for latent TB can be initiated prior to the next administration of study agent and continued to completion. Subjects with persistently indeterminate QuantiFERON®-TB Gold test results may continue without treatment for latent TB if active TB is ruled out, their chest radiograph shows no abnormality suggestive of TB (active or old, inactive TB) and the subject has no additional risk factors for TB as determined by the investigator. This determination must be promptly reported to the sponsor's medical monitor and recorded in the subject's source documents and initialed by the investigator.—A subject receiving treatment for latent TB discontinues this treatment prematurely or is non-compliant with the therapy.
The initiation of protocol-prohibited medications.
Investigator or Sponsor's medical monitor believes that for safety reasons it is in the subject's best interest.
Discontinuation of study agent administration must be considered for subjects who develop a serious infection.

Withdrawal from the Study
A subject will be withdrawn from the study for any of the following reasons:
 Lost to follow-up
 Withdrawal of consent
 Death
If a subject is lost to follow-up, every reasonable effort must be made by the study site personnel to contact the subject and determine the reason for discontinuation/withdrawal. The measures taken to follow up must be documented.

When a subject withdraws before completing the study, the reason for withdrawal is to be documented in the eCRF and in the source document. Study drug assigned to the withdrawn subject may not be assigned to another subject. Subjects who withdraw will not be replaced. If a subject discontinues from the study agent administrations before the end of treatment, posttreatment assessments should be obtained.

Withdrawal of Participation in the Collection of Optional Research Samples while Remaining in the Main Study The subject may withdraw consent for optional research samples while remaining in the study. In such a case, the optional research samples will be destroyed. The sample destruction process will proceed as described above.

Withdrawal from the Use of Samples in Future Research

The subject may withdraw consent for use of samples for research. In such a case, samples will be destroyed after they are no longer needed for the clinical study. Details of the sample retention for research are presented in the main ICF and in the separate ICF for optional research samples.

Statistical Methods

Simple descriptive summary statistics, such as n, mean, SD, median, IQ range, minimum, and maximum for continuous variables, and counts and percentages for discrete variables will be used to summarize most data.

The chi-squared test or Cochran-Mantel-Haenszel (CMH) test stratified by MTX use at baseline (yes/no) will be used to compare categorical variables such as the proportion of subjects responding to treatment, unless otherwise stated. In general, ANOVA with baseline use of MTX therapy as a factor will be used for analyzing continuous variables, unless otherwise stated. All statistical tests will be performed at $\alpha=0.05$ (2-sided). Van der Waerden normal scores will be utilized if endpoints are deemed non-Gaussian, eg, change from baseline in vdH-S. In addition to statistical analyses, graphical data displays (eg, line plots) and subject listings may also be used to summarize/present the data.

Efficacy and subject baseline analyses will utilize an intent-to-treat population (i.e., all subjects who are randomized) unless otherwise stated. Subjects included in the efficacy analyses will be summarized according to their assigned treatment group regardless of whether or not they receive the assigned treatment.

Safety and PK analyses will include all subjects who received at least one administration of study treatment.

Subject Information

Subjects' demographics data (eg, age, race, sex, height, weight) and baseline disease characteristics (eg, duration of disease, joint count, and CRP) will be summarized by treatment group.

Sample Size Determination

The sample size estimates are based on data from the Sponsor's most recent PsA study with the biologic, ustekinumab (an anti-IL12/23 monoclonal antibody developed by the Sponsor). The Phase 3 study of ustekinumab (CNTO1275PSA3001) in subjects with active PsA included a minimum CRP criterion and represents a more current PsA population. The ACR 20 response rates for the CNTO1275PSA3001 study were 22.8%, 42.4% and 49.5% at Week 24 for the placebo, ustekinumab 45 mg, and 90 mg treatment groups, respectively. A total of 440 subjects, 220 in each treatment group, will ensure 99% power to detect significant differences in the proportion of responders between treatment groups at Week 14, assuming a 40% ACR 20 response in the golimumab 2 mg/kg group and a 20% response in the placebo group at a 2-sided significance level of 0.05 using the chi-square test (Table 6).

TABLE 6

Results of Power Calculations - Proportion of Subjects with ACR 20 Responses

| Sample size per arm | Golimumab % ACR 20 responders | Placebo % ACR 20 responders | Delta | Power (%) |
|---|---|---|---|---|
| 220 | 0.25 | 0.10 | 0.15 | 98.7 |
| 220 | 0.30 | 0.10 | 0.20 | >99.9 |
| 220 | 0.35 | 0.10 | 0.25 | >99.9 |
| 220 | 0.40 | 0.10 | 0.30 | >99.9 |
| 220 | 0.35 | 0.20 | 0.15 | 94.3 |
| 220 | 0.40 | 0.20 | 0.20 | 99.6 |
| 220 | 0.45 | 0.20 | 0.25 | >99.9 |
| 220 | 0.50 | 0.20 | 0.30 | >99.9 |
| 220 | 0.45 | 0.30 | 0.15 | 90.4 |
| 220 | 0.50 | 0.30 | 0.20 | 99.1 |
| 220 | 0.55 | 0.30 | 0.25 | >99.9 |
| 220 | 0.60 | 0.30 | 0.30 | >99.9 |

Simulations were also performed for each scenario to calculate the power to detect significant differences in the change from baseline in total modified vdH-S scores at Week 24 (Table 7).

At Week 24, the mean (standard deviation) change from baseline in total modified vdH-S score excluding extreme outliers, were 0.92 (2.15), 0.28 (1.94) and 0.17 (1.446) in the placebo, ustekinumab 45 mg and 90 mg treatment groups, respectively, in the CNTO1275PSA3001 study. Assuming the mean change from baseline in total modified vdH-S score of 0.9 in the placebo group, 0.35 in the golimumab 2 mg/kg group and a standard deviation of 2 for each treatment group, respectively, 440 subjects (i.e., 220 per arm) would yield 90.7% power to detect a significant difference at a level of significance of 0.05 (2-sided).

TABLE 7

Results of Power Calculations - Change from baseline in total modified vdH-S score

| Delta | Placebo mean change | Golimumab mean change | Power (%) |
|---|---|---|---|
| 0.30 | 0.90 | 0.60 | 40.2 |
| 0.35 | 0.90 | 0.55 | 52.3 |
| 0.45 | 0.90 | 0.45 | 75.1 |
| 0.50 | 0.90 | 0.40 | 84.1 |
| 0.55 | 0.90 | 0.35 | 90.7 |
| 0.60 | 0.90 | 0.30 | 94.8 |
| 0.65 | 0.90 | 0.25 | 97.2 |
| 0.70 | 0.90 | 0.20 | 98.7 |
| 0.75 | 0.90 | 0.15 | 99.5 |
| 0.80 | 0.90 | 0.10 | 99.8 |
| 0.85 | 0.90 | 0.05 | 99.9 |
| 0.90 | 0.90 | 0.00 | >99.9 |
| 0.95 | 0.90 | -0.05 | >99.9 |
| 1.00 | 0.90 | -0.10 | >99.9 |

Interim Analysis

No interim analysis is planned. However, an independent data monitoring committee (DMC) will review safety data periodically to monitor subject safety.

Efficacy Analysis

Primary Endpoint Analyses

The primary endpoint is the proportion of subjects who achieve an ACR 20 response at Week 14.

Reduction in signs and symptoms of arthritis will be evaluated by comparing the proportion of subjects who achieve an ACR 20 response at Week 14 between the treatment groups. A Cochran-Mantel-Haenszel (CMH) test, stratified by baseline MTX use (yes, or no) will be performed for this analysis at a significance level of 0.05 (2-sided).

In this primary efficacy analysis, data from all randomized subjects will be analyzed according to their assigned treatment group regardless of their actual treatment received. A last observation carried forward (LOCF) procedure will be used to impute the missing ACR components if the subjects have data for at least 1 ACR component at Week 14. If the subjects do not have data for all the ACR components at Week 14, the subjects will be considered non-responders. In addition, treatment failure rules will be applied.

Sensitivity analyses with modified analysis sets and different rules may be conducted.

In addition, subgroup analysis will be performed to evaluate consistency in the primary efficacy endpoint by demographic characteristics, baseline disease characteristics, and baseline medications. Interaction test between the subgroups and treatment group will also be provided if appropriate.

Major Secondary Analyses

The following major secondary analyses will be performed in order of importance as specified below:
1. The change from baseline in the HAQ-DI score at Week 14 will be summarized and compared between treatment groups.
2. The proportion of subjects who achieve an ACR 50 response at Week 14 will be summarized and compared between treatment groups.
3. The proportion of subjects (with baseline ≥3% BSA psoriatic involvement) who achieve a PASI 75 response at Week 14 will be summarized and compared between treatment groups.
4. The change from baseline in total modified vdH-S score at Week 24 will be summarized and compared between treatment groups.

Since there are only 2 treatment groups (1 statistical comparison), there is no need to adjust for multiplicity within each efficacy endpoint.

To control the Type I error rate for multiplicity, the first major secondary endpoint will be tested only if the primary endpoint achieved statistical significance at a 0.05 level of significance (2-sided). The subsequent major secondary endpoints will be tested only if the primary endpoint and the preceding major secondary endpoint(s) are statistically significant at a 0.05 level of significance (2-sided).

For the major secondary endpoint of change from baseline in total modified vdH-S score at Week 24, a modified ITT population, which includes all randomized subjects who have a baseline total modified vdH-S score, will be included in the analyses. Multiple imputations method will be used to impute Week 24 radiograph scores for missing data A sensitivity analysis using Week 24 radiographic data regardless of whether a subject early escaped or discontinued prior to Week 24 will also be performed.

Other Planned Efficacy Analyses

Controlled Secondary Endpoints Analyses (with Control of Type I Error Rate for Multiplicity)

The following efficacy analyses will be performed in addition to the primary and major secondary analyses:
1. The change from baseline in enthesitis score at Week 14 in subjects with enthesitis at baseline will be summarized and compared between treatment groups.
2. The change from baseline in dactylitis scores at Week 14 in subjects with dactylitis at baseline will be summarized and compared between treatment groups.
3. The change from baseline in SF-36 PCS at Week 14 will be summarized and compared between treatment groups.
4. The proportion of subject with an ACR 50 response at Week 24 will be summarized and compared between treatment groups.
5. The proportion of subjects who achieve an ACR 70 response at Week 14 will be summarized and compared between treatment groups.
6. The change from baseline in SF-36 MCS at Week 14 will be summarized and compared between treatment groups.

To control for multiplicity, the above analyses will be performed sequentially according to the above order only when the primary and major secondary endpoints achieved statistically significance. Otherwise, nominal p-values will be provided.

Analyses for Other Secondary Endpoints Include

Analyses Related to Reduction of Signs and Symptoms and Physical Function

The following endpoints will be summarized by treatment groups. Summaries will be over time through Week 52 if the visit of the endpoint is not specified. Comparisons between treatment groups will be made at visits prior to and at Week 24.
1. The proportion of subjects who achieve an ACR 20 response at Week 2 will be summarized by treatment group and compared between groups.
2. The proportion of subjects who achieved an ACR 20, ACR 50, ACR 70 and ACR 90 responses at Week 24. Summary will be done by baseline MTX use and overall. In addition, these endpoints will also be summarized using observed data without imputation.
3. The percent change from baseline in the components of the ACR response will be compared at Week 14 and Week 24 between the treatment groups, and will be summarized overtime.
4. The change from baseline in HAQ-DI score will be summarized for each treatment group over time and will be compared between treatment groups at Week 24.
5. The proportion of HAQ-DI responders (subjects achieving a ≥0.3 improvement in HAQ-DI score) will be summarized for each treatment group over time and will be compared between the treatment groups at Weeks 14 and 24.
6. The percent change from baseline in the dactylitis score in subjects with dactylitis at baseline and the proportion of subjects with digits with dactylitis will be summarized for each treatment group over time and compared between the treatment groups at Week 24.
7. The percent change from baseline in the enthesitis score in subjects with enthesitis at baseline and the proportion of subjects with enthesitis will be summarized for each treatment group over time and compared between the treatment groups at Week 24.
8. The proportion of subjects who are ACR 20 responders at Week 52 in subjects who are responders at Week 24 will be summarized by treatment group. Similar summaries will be performed for ACR 50, 70 and 90 responders.
9. The proportion of subjects who are HAQ-DI responders (subjects achieving a ≥0.3 improvement in HAQ-DI score) at Week 52 in subjects who are responders at Week 24 will be summarized by treatment group.

10. The proportion of subjects achieving MDA will be summarized for each treatment group over time and compared between treatment groups at Weeks 14 and 24.

Analyses Related to Skin Disease Include

The following analyses will be performed:
1. For subjects with ≥3% BSA psoriasis skin involvement at baseline, the proportion of subjects achieving ≥50%, ≥75%, ≥90%, and 100% improvement in PASI from baseline will be summarized for each treatment group over time overall, and by baseline MTX use, and compared between the treatment groups at Weeks 14 and 24.
2. For subjects with ≥3% BSA psoriasis skin involvement at baseline, the percent improvement from baseline in PASI will be summarized for each treatment group over time and compared between the treatment groups at Weeks 14 and 24.
3. For subjects with ≥3% BSA psoriasis skin involvement at baseline, the proportion of subjects achieving both PASI 75 and ACR 20 responses will be summarized for each treatment group over time and compared between the treatment groups at Weeks 14 and 24.

Analyses Related to Joint Structural Damage Include

Analyses at Week 24 will be performed on data from Read Campaign 1 and analyses at Week 52 will be performed on data from Read Campaign 2.

The following analyses will be performed:
1. The proportion of subjects who had a change from baseline in total modified vdH-S score ≤0 at Week 24 will be summarized and compared between treatment groups.
2. The change from baseline in total modified vdH-S score at Week 24 and Week 52 will be summarized by treatment group and by early escape status.
3. The change from baseline in the total modified vdH-S score at Week 24 and Week 52 will be compared between treatment groups.
4. The change in total modified vdH-S score from Week 0 to Week 24, and from Week 24 to Week 52 will be summarized by treatment group and by early escape status
5. The change from baseline in total modified vdH-S score by region (hands, feet) will be summarized by treatment group will be compared between the treatment groups at Week 24 and Week 52.
6. The change from baseline in total modified vdH-S scores by type of damage (Erosion and JSN) will be summarized by treatment group and will be compared between the treatment groups at Week 24 and Week 52
7. Number of subjects with maintenance of joint damage-free state (total modified vdH-S score of 0, erosion score of 0, or JSN score of 0) will be summarized by treatment group and will be compared between the treatment groups at Week 24 and Week 52
8. Number of subjects with change from baseline in the total modified vdH-S score ≤0 or ≤0.5 will be summarized by treatment group and will be compared between the treatment groups at Week 24 and Week 52.
9. The empirical cumulative distribution function of the change from baseline in the total modified vdH-S score at Week 24 and Week 52 will be presented.
10. The change from baseline in total modified vdH-S score, erosion score and JSN score by reader at Week 24 and Week 52 will be summarized by treatment group.

Analyses Related to Health Related Quality of Life Include

The following analyses will be performed:
1. The change from baseline in the PCS score and the MCS score of the SF-36 at Week 24 will be compared between the treatment groups.
2. The change from baseline in the PCS score and the MCS score of the SF-36 will be summarized for each treatment group over time.
3. The change from baseline in SF-36 scales will be summarized by treatment group over time and compared between treatment groups at Weeks 14 and 24.
4. The proportion of subjects achieving an SF-36 PCS score improvement of ≥5 will be summarized over time and compared between the treatment groups at Weeks 14 and 24.
5. The proportion of subjects achieving an SF-36 MCS score improvement of ≥5 will be summarized over time and compared between treatment groups at Weeks 14 and 24.

Criteria for Endpoints

The study will be considered positive if the proportion of subjects with ACR 20 at Week 14 is demonstrated to be statistically significantly greater in the golimumab group compared with the placebo group.

Study Drug Information

Physical Description of Study Drug

Golimumab

The 50 mg Golimumab Final Vialed Product (FVP) for IV administration is supplied as a single use, sterile solution containing CNTO 148 IgG in a 4 mL, Type I glass vial. Each vial contains 4 mL solution of 12.5 mg/mL golimumab in an aqueous medium of histidine, sorbitol, and polysorbate 80 at pH 5.5. No preservatives are present.

Placebo

Normal saline will be supplied as a sterile liquid for IV infusion in single-use infusion bags. No preservatives are present.

Methotrexate

Methotrexate (oral or injectable) will not be supplied by the Sponsor but rather must be acquired from a commercial pharmacy.

Medications Prescribed for Early Escape

Methotrexate, NSAIDs, corticosteroids, sulfasalazine, hydroxychloroquine, and leflunomide will not be supplied by the Sponsor but rather must be acquired from a commercial pharmacy.

Preparation, Handling, and Storage

At the study site, vials of golimumab solution must be stored in a secured refrigerator at 2° C. to 8° C. (35.6° F. to 46.4° F.), not frozen and protected from light. Vigorous shaking of the product should be avoided. Prior to administration, the product should be inspected visually for particulate matter and discoloration. If discoloration, visible particles, or other foreign particles are observed in the solution, the product should not be used.

Study agent in glass vials will be ready for use. The study agent IV infusions will be prepared according to the subject's weight by the unblinded pharmacist or other appropriately licensed and authorized personnel. The pharmacist or other appropriately licensed and authorized personnel will prepare the required volume of study agent using appropriate number of vials.

Aseptic procedures must be used during the preparation and administration of study material. Exposure to direct sunlight should be avoided during preparation and administration.

Results and Conclusion

Efficacy and Safety Through Week 24 for Intravenous Golimumab in Adult Patients with Active Psoriatic Arthritis Introduction: The GO-VIBRANT study is a Phase 3, multicenter, randomized, double-blind, placebo-controlled trial that was designed to evaluate the safety and efficacy of intravenous (IV) golimumab in adult patients with active PsA (biological naïve). Biologic-naïve active PsA patients were randomized (1:1) to IV golimumab 2 mg/kg at weeks (wk) 0, 4, and every 8 wks thereafter or placebo at wks 0, 4, 12, and 20 with crossover to golimumab at wk24. The primary endpoint was ACR20 response at wk14. Multiplicity-controlled endpoints included ACR50, ACR70, PASI 75, change from baseline in HAQ-DI, enthesitis, dactylitis, SF-36 PCS/MCS scores at wk14; and ACR50 and change from baseline in total modified vdH-S (structural damage) score at wk24. The efficacy analyses were based on randomized treatment and adverse events (AE) through wk24 are reported. Investigators are blinded through wk60.

Results: 480 patients were randomized (placebo: 239; golimumab: 241). The study met its primary endpoint and all of the controlled secondary endpoints. At wk14, a significantly greater proportion of golimumab patients vs placebo achieved ACR20 (75.1% vs. 21.8%). In addition, the golimumab treatment resulted in a significant change from baseline HAQ-DI score (−0.60 vs. −0.12), ACR50 (43.6% vs. 6.3%), PASI 75 (59.2% vs. 13.6%), ACR70 (24.5% vs. 2.1%), a change from baseline in enthesitis and dactylitis scores (−1.8 vs. −0.8 and −7.8 vs. −2.8, respectively), and a change from baseline in SF-36 PCS and SF-36 MCS scores (8.65 vs. 2.69 and 5.33 vs. 0.97, respectively) (all p<0.001) at wk14. At wk24, a significantly greater proportion of golimumab patients vs. placebo patients achieved ACR 50 (53.5% vs. 6.3%, p<0.001). At wk24, there was significantly less progression of structural damage for golimumab patients vs placebo as measured by change from baseline in total modified vdH-S score (−0.36 vs. 1.95; p<0.001). ACR20 was significantly higher with golimumab than placebo as early as wk2 (45.6% vs. 7.5%; p<0.001) and 27.0% of golimumab patients (vs. 4.2% placebo) achieved Minimal Disease Activity by wk14. With the substantial difference in golimumab vs. placebo treated patients, the number needed to treat for ACR20 was 1.9 in a post-hoc analysis at wk14 (Table). Through wk24, 46.3% of golimumab patients and 40.6% of placebo patients had ≥1 AE; 2.9% vs. 3.3% of patients, respectively, had ≥1 serious AE. The most common treatment-emergent type of AE was infection (20.0% of golimumab patients vs. 13.8% of placebo patients); only 3 were serious. No opportunistic infections or cases of tuberculosis were reported through wk24. Two deaths, 2 malignancies, and 1 demyelinating event were reported. The rate of infusion reactions was low at <2%; none were serious or severe.

Conclusion: For patients with active PsA, IV golimumab demonstrated clinically meaningful and surprisingly significant improvements of disease activity and physical function, skin psoriasis clearance, reduction in dactylitis and enthesitis, HRQoL and inhibition of structural progression. Golimumab was also well-tolerated through wk24 and the safety profile was consistent with other anti-TNF therapies, including SC golimumab.

TABLE 8

| Clinical Response | Placebo | Golimumab 2 mg/kg | P-values |
|---|---|---|---|
| Patients randomized, n | 239 | 241 | |
| Clinical efficacy at wk14 | | | |
| ACR20, n (%) | 52 (21.8%) | 181 (75.1%)) | p < 0.001 |
| ACR50, n (%) | 15 (6.3%) | 105 (43.6%) | p < 0.001 |
| ACR70, n (%) | 5 (2.1%) | 59 (24.5%) | p < 0.001 |
| PASI 75, n (%)* | 27/198 (13.6%) | 116/196 (59.2%) | p < 0.001 |
| Change from baseline in HAQ-DI | | | |
| n | 222 | 233 | |
| Mean (SD) | −0.12 (0.47) | −0.60 (0.53) | p < 0.001 |
| Change from baseline in enthesitis** | | | |
| n | 173 | 182 | |
| Mean (SD) | −0.8 (1.98) | −1.87 (1.75) | p < 0.001 |
| Change from baseline in dactylitis** | | | |
| n | 115 | 130 | |
| Mean (SD) | −−2.8 (7.03) | −7.8 (8.57) | p < 0.001 |
| Minimal Disease Activity | | | |
| MDA n/N (%) | 10/239 (4.2%) | 65/241 (27.0%) | p < 0.001 |
| Number Needed to Treat | | | |
| NNT (95% CI) | | 1.9 (1.64, 2.18) | |
| Clinical efficacy at Week 24 | | | |
| ACR50, n (%) | 15 (6.3%) | 129 (53.5%) | |
| Imaging data at Week 24 | | | |
| Change from baseline in vdH-S score | | | |
| N | 237 | 237 | |
| Mean (SE) | 1.95 (0.264) | −0.36 (0.144) | p < 0.001 |
| HRQoL at wk14 | | | |
| Change from baseline in SF-36 PCS score | | | |
| n | 222 | 233 | |
| Mean (SD) | 2.69 (5.92) | 8.65 (7.60) | p < 0.001 |
| Change from baseline in SF-36 MCS score | | | |
| n | 222 | 233 | |
| Mean (SD) | 0.97 (7.64) | 5.33 (9.95) | p < 0.001 |

*Among patients with ≥3% BSA involvement
**Among patients with finding at baseline
ACR, American College of Rheumatology Criteria;
PASI, Psoriasis Area Severity Index;
HAQ-DI, Health assessment questionnaire disability index;
CI, confidence interval;
SD, standard deviation;
SE, standard error;
vdH-S, total modified van der Heijde-Sharp;
HRQoL, health related quality of life;
SF-36 PCS/MCS, 36-item Short-Form Health Survey Physical/Mental Component Summary

TABLE 9

Number of Subjects Who Achieved an ACR 20 Response at Week 14 Stratified by Baseline MTX Usage; Full Analysis Set

|  | Placebo | Golimumab 2 mg/kg |
|---|---|---|
| Subjects evaluable for ACR 20 response at Week 14[a] | 239 | 241 |
| Subjects with ACR 20 response | 52 (21.8%) | 181 (75.1%) |
| % Difference (95% CI)[b] |  | 53.4 (45.80, 60.90) |
| p-value[c] |  | <0.001 |
| Baseline MTX usage: Yes | 173 | 163 |
| Subjects with ACR 20 response | 38 (22.0%) | 126 (77.3%) |
| Baseline MTX usage: No | 66 | 78 |
| Subjects with ACR 20 response | 14 (21.2%) | 55 (70.5%) |

[a]ACR 20 response is based on imputed data using treatment failure, LOCF for partially missing data, and NRI for completely missing data.
[b]The confidence interval is based on Wald statistic controlling for baseline MTX usage (Yes, No).
[c]The p-value is based on CMH test controlling for baseline MTX usage (Yes, No).

Numerous modifications and variations of the present invention are possible in light of the above teachings and, therefore, are within the scope of the appended claims.

REFERENCES

1. Basra M K A, Fenech R, Gatt R M, Salek M S, Finlay A Y. The Dermatology Life Quality Index 1994-2007: a comprehensive review of validation data and clinical results. Br J Rheumatol. 2008; 159:997-1035.
2. Beutler B, Greenwald D, Hulmes J D, et al. Identity of tumour necrosis factor and the macrophage-secreted factor cachectin. Nature. 1985; 316(6028):552-554.
3. Cassell S E, Bieber J D, Rich P, Tutuncu Z N, Lee S J, Kalunian K C, Wu C W, Kavanaugh A. The modified Nail Psoriasis Severity Index: validation of an instrument to assess psoriatic nail involvement in patients with psoriatic arthritis. J Rheumatol. 2007; 34(1): 123-129.
4. Cella D, Yount S, Sorensen M, Chartash E, Sengupta N, Grober J. Validation of the Functional Assessment of Chronic Illness Therapy Fatigue Scale relative to other instrumentation in patients with rheumatoid arthritis. J Rheumatol. 2005; 32(5): 811-819.
5. Chandran V, Bhella S, Schentag C, Gladman D. Functional Assessment of Chronic Illness Therapy-Fatigue Scale is valid in patients with psoriatic arthritis. Ann Rheum Dis. 2007; 66:936-939.
6. Coates L C, Helliwell P S. Validation of minimal disease activity criteria for psoriatic arthritis using interventional trial data. Arthritis Care Res (Hoboken). 2010; 62(7): 965-969.
7. Costello P, FitzGerald O. Disease mechanisms in psoriasis and psoriatic arthritis. Curr Rheumatol Rep. 2001; 3(5): 419-427.
8. EuroQol Group. EuroQol—a new facility for the measurement of health-related quality of life. Health Policy. 1990; 16:199-208.
9. Feldman S R, Gordon K B, Bala M, et al. Infliximab treatment results in significant improvement in the quality of life of patients with severe psoriasis: a double-blind placebo-controlled trial. British Journal of Dermatology. 2005; 152:954-960.
10. Felson D T, Anderson J J, Boers M, et al. American College of Rheumatology. Preliminary definition of improvement in rheumatoid arthritis. Arthritis Rheum. 1995; 38(6): 727-735.
11. Finlay A Y, Khan G K. Dermatology Life Quality Index (DLQI)—a simple practical measure for routine clinical use. Clin Exp Dermatol. 1994; 19(3):210-216.
12. Fredriksson T, Pettersson U. Severe psoriasis—oral therapy with a new retinoid. Dermatologica. 1978; 157 (4):238-244.
13. Fries J F, Spitz P, Kraines R G, Holman H R. Measurement of patient outcomes in arthritis. Arthritis Rheum. 1980; 23(2):137-145.
14. Garrett S, Jenkinson T, Kennedy L G, Whitelock H, Gaisford P, Calin A. A new approach to defining disease status in ankylosing spondylitis: the Bath Ankylosing Spondylitis Disease Activity Index. J Rheumatol. 1994; 21(12): 2286-2291.
15. Gladman D D, Inman R D, Cook R J, et al. International spondyloarthritis interobserver reliability exercise—the INSPIRE study: II. Assessment of peripheral joints, enthesitis, and dactylitis. J Rheumatol. 2007; 34(8): 1740-1745.
16. Gladman D D, Ziouzina O, Thavaneswaran A, Chandran V. Dactylitis in psoriatic arthritis: prevalence and response to therapy in the biologic era. J Rheumatol. 2013; 40(8): 1357-1359.
17. Goedkoop A Y, Kraan M C, Teunissen M B, et al. Early effects of tumour necrosis factor alpha blockade on skin and synovial tissue in patients with active psoriasis and psoriatic arthritis. Ann Rheum Dis. 2004; 63(7): 769-773.
18. Healy P J, Helliwell P S. Measuring clinical enthesitis in psoriatic arthritis: assessment of existing measures and development of an instrument specific to psoriatic arthritis. Arthritis Rheum. 2008; 59(5):686-691
19. Husted J A, Gladman D D, Cook R J, Farewell V T. Responsiveness of health status instruments to changes in articular status and perceived health in patients with psoriatic arthritis. J Rheumatol. 1998; 25(11):2146-2155.
20. Khilji F A, Gonzalez M, Finlay A Y. Clinical meaning of change in dermatology life quality index scores. Br J Dermatol. 2002; 147(suppl 62): 25-54. SIMPONI IV (golimumab) Clinical Protocol CNTO148PSA3001 Amendment 2 98 Approved, 29 Jun. 2016
21. Mease P J, Antoni C E, Gladman D D, Taylor W J. Psoriatic arthritis assessment tools in clinical trials. Ann Rheum Dis. 2005; 64(Suppl II):ii49-ii54.
22. Mease P J, Kivitz A J, Burch F X, et al. Etanercept treatment of psoriatic arthritis: safety, efficacy, and effect on disease progression. Arthritis Rheum. 2004; 50(7): 2264-2272
23. Mease P J. Measures of psoriatic arthritis: Tender and Swollen Joint Assessment, Psoriasis Area and Severity Index (PASI), Nail Psoriasis Severity Index (NAPSI), Modified Nail Psoriasis Severity Index (mNAPSI), Mander/Newcastle Enthesitis Index (MEI), Leeds Enthesitis Index (LEI), Spondyloarthritis Research Consortium of Canada (SPARCC), Maastricht Ankylosing Spondylitis Enthesis Score (MASES), Leeds Dactylitis Index (LDI), Patient Global for Psoriatic Arthritis, Dermatology Life Quality Index (DLQI), Psoriatic Arthritis Quality of Life (PsAQOL), Functional Assessment of Chronic Illness Therapy-Fatigue (FACIT-F), Psoriatic Arthritis Response Criteria (PsARC), Psoriatic Arthritis Joint Activity Index (PsAJAI), Disease Activity in Psoriatic Arthritis (DAPSA), and Composite Psoriatic Disease Activity Index (CPDAI). Arthritis Care Res (Hoboken). 2011; 63 Suppl 11:S64-S85.
24. Partsch G, Steiner G, Leeb B F, Dunky A, Broll H, Smolen J S. Highly increased levels of tumor necrosis factor-alpha and other proinflammatory cytokines in psoriatic arthritis synovial fluid. J Rheumatol. 1997; 24(3): 518-523.

25. Pham T, Guillemin F, Claudepierre P, et al. TNF a antagonist therapy in ankylosing spondylitis and psoriatic arthritis: recommendations of the French Society for Rheumatology. Joint Bone Spine. 2006; 73:547-553.
26. Ritchlin C, Haas-Smith S A, Hicks D, Cappuccio J, Osterland C K, Looney R J. Patterns of cytokine production in psoriatic synovium. J Rheumatol. 1998; 25(8): 1544-1552.
27. Taylor W, Gladman D, Helliwell P, Marchesoni A, Mease P, Mielants H; CASPAR Study Group. Classification criteria for psoriatic arthritis: development of new criteria from a large international study. Arthritis Rheum. 2006; 54(8):2665-2673.
28. van der Heijde D M, van Leeuwen M A, van Riel P L, et al. Biannual radiographic assessments of hands and feet in a three-year prospective followup of patients with early rheumatoid arthritis. Arthritis Rheum. 1992; 35(1): 26-34.
29. van der Linden M A. Disease Activity Scores using C-reactive protein. Apr. 5, 2004. Available at: www.umcn.nl/scientist/afdelingen/reumatologie/the_das/the_das_crp. Accessed 19 Aug. 2005
30. van Riel P, Fransen J, Scott D L. EULAR handbook of clinical assessments in rheumatoid arthritis. Third ed. Alphen Aan Den Rijn, The Netherlands: Van Zuiden Communications B.V. 2004. Available Upon Request.
31. van Riel P L, van Gestel A M, Scott D L, for the EULAR Standing Committee for International Clinical Studies Including Therapeutic Trials—ESCISIT. EULAR Handbook of Clinical Assessments in Rheumatoid Arthritis. Alphen Aan Den Rijn, The Netherlands: Van Zuiden Communications B.V.; 2000; 40.
32. Veale D J, Markham T, Fearon U, et al. St Vincents University Hospital, Dublin, Ireland. Therapy in psoriasis and psoriatic arthritis: anti-TNF-alpha clinical and angiogenic responses. Arthritis Rheum. 2003; 48(suppl):S168-S169.
33. Ware J E Jr, Sherbourne C D. The MOS 36-item short-form health survey (SF-36), I: conceptual framework and item selection. Med Care. 1992; 30(6):473-483.
34. Ware J E, Kosinski M, Keller S D. Interpretation: Norm-Based. In: SF-36 Physical and Mental Health Summary Scales: A User's Manual. Boston, MA: The Health Institute; 1994; 8:1-8:42.
35. Zochling J, van der Heijde D, Burgos-Vargas R, et al. ASAS/EULAR recommendations for the management of ankylosing spondylitis. Ann Rheum Dis. 2006; 65(4):442-452.

What is claimed is:

1. A method for treating a tumor necrosis factor alpha (TNF-α) related condition, wherein the TNF-α related condition is active psoriatic arthritis, the method comprising: administering to a subject having active psoriatic arthritis a composition comprising a safe and effective amount of at least one isolated mammalian anti-TNF-α antibody comprising:
   a. a heavy chain (HC) complementary determining region (CDR) 1 comprising an amino acid sequence of SEQ ID NO: 1;
   b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
   c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
   d. a light chain (LC) CDR1 comprising an amino acid sequence of SEQ ID NO: 4; wherein position 7 of SEQ ID NO: 4 is tyrosine;
   e. a LC CDR2 comprising an amino acid sequence of SEQ ID NO: 5; and
   f. a LC CDR3 comprising an amino acid sequence of SEQ ID NO: 6, and at least one pharmaceutically acceptable carrier or diluent, wherein said composition is administered via intravenous (IV) infusion, wherein said anti-TNF-α antibody is administered at a dose of 2 mg/kg, over 30±10 minutes, at Weeks 0 and 4, then every 8 weeks (q8w) thereafter, and wherein at week 14 of treatment patients treated with the anti-TNF-α antibody achieve a mean change from baseline in one or more criteria selected from the group consisting of: Health Assessment Questionnaire Disability Index score (HAQ-DI)=−0.60±0.53 SD, enthesitis=−1.87±1.75 SD, dactylitis=−7.8±8.57 SD, Short-Form Health Survey Physical Summary score (SF-36 PCS)=8.65±7.60 SD, and Short-Form Health Survey Mental Component Summary score (SF-36 MCS)=5.33±9.95 SD.

2. The method according to claim 1, further comprising administering said composition with or without methotrexate (MTX).

3. A method for treating a TNF-α related condition, wherein the TNF-α related condition is active psoriatic arthritis, the method comprising: administering to a subject having active psoriatic arthritis a composition comprising a safe and effective amount of at least one isolated mammalian anti-TNF-α antibody comprising:
   a. a heavy chain (HC) complementary determining region (CDR) 1 comprising an amino acid sequence of SEQ ID NO: 1;
   b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
   c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
   d. a light chain (LC) CDR1 comprising an amino acid sequence of SEQ ID NO: 4; wherein position 7 of SEQ ID NO: 4 is tyrosine;
   e. a LC CDR2 comprising an amino acid sequence of SEQ ID NO: 5; and
   f. a LC CDR3 comprising an amino acid sequence of SEQ ID NO: 6, and at least one pharmaceutically acceptable carrier or diluent, wherein said composition is administered via IV infusion, wherein said anti-TNF-α antibody is administered at a dose of 2 mg/kg, over 30±10 minutes, at Weeks 0 and 4, then every 8 weeks (q8w) thereafter, and wherein at week 24 of treatment patients treated with the anti-TNF-α antibody achieve a mean change from baseline in total modified van der Heijde-Sharp score (vdH-S)=−0.36±0.144 SE.

4. The method according to claim 3, further comprising administering said composition with or without methotrexate (MTX).

5. A method for treating a TNF-α related condition, wherein the TNF-α related condition is active psoriatic arthritis, the method comprising: administering to a subject having active psoriatic arthritis a composition comprising a safe and effective amount of at least one isolated mammalian anti-TNF-α antibody comprising:
   a. a heavy chain (HC) complementary determining region (CDR) 1 comprising an amino acid sequence of SEQ ID NO: 1;
   b. a HC CDR2 comprising an amino acid sequence of SEQ ID NO: 2; wherein position 1 of SEQ ID NO: 2 is phenylalanine, position 2 of SEQ ID NO: 2 is methionine, position 3 of SEQ ID NO: 2 is serine, position 4 of SEQ ID NO: 2 is tyrosine, position 10 of SEQ ID NO: 2 is lysine, position 11 of SEQ ID NO: 2 is tyrosine, and position 17 of SEQ ID NO: 2 is glycine;
   c. a HC CDR3 comprising an amino acid sequence of SEQ ID NO: 3; wherein position 4 of SEQ ID NO: 3 is isoleucine, position 5 of SEQ ID NO: 3 is alanine, and position 9 of SEQ ID NO: 3 is asparagine;
   d. a light chain (LC) CDR1 comprising an amino acid sequence of SEQ ID NO: 4; wherein position 7 of SEQ ID NO: 4 is tyrosine;
   e. a LC CDR2 comprising an amino acid sequence of SEQ ID NO: 5; and
   f. a LC CDR3 comprising an amino acid sequence of SEQ ID NO: 6, wherein said anti-TNF-α antibody is administered via intravenous (IV) infusion, wherein said antibody is administered at a dose of 2 mg/kg, over 30±10 minutes, at Weeks 0 and 4, and then every 8 weeks (q8w) thereafter, and wherein ≥65% of patients receiving the treatment achieve ACR20 at week 14 of treatment.

6. The method according to claim 5, wherein said ≥65% of patients that achieve ACR20 at week 14 of treatment with a treatment difference (improvement compared to placebo) of about 50%.

7. The method according to claim 5, wherein said antibody is administered with or without methotrexate (MTX).

\* \* \* \* \*